US009580413B2

(12) United States Patent
Hori et al.

(10) Patent No.: US 9,580,413 B2
(45) Date of Patent: Feb. 28, 2017

(54) SUBSTITUTED PYRROLIDINES AS ROS TYROSINE KINASE INHIBITORS

(71) Applicant: NIPPON SHINYAKU CO., LTD., Kyoto-shi, Kyoto (JP)

(72) Inventors: Katsutoshi Hori, Kusatsu (JP); Hiroki Hayase, Toyonaka (JP); Tomohiro Terada, Ohtsu (JP)

(73) Assignee: NIPPON SHINYAKU CO., LTD., Kyoto (JP)

( * ) Notice: Subject to any disclaimer, the term of this patent is extended or adjusted under 35 U.S.C. 154(b) by 0 days.

(21) Appl. No.: 14/402,198

(22) PCT Filed: May 29, 2013

(86) PCT No.: PCT/JP2013/064933
§ 371 (c)(1),
(2) Date: Nov. 19, 2014

(87) PCT Pub. No.: WO2013/180183
PCT Pub. Date: Dec. 5, 2013

(65) Prior Publication Data
US 2015/0152095 A1 Jun. 4, 2015

(30) Foreign Application Priority Data
May 30, 2012 (JP) ................................ 2012-122715

(51) Int. Cl.
*A61K 31/4025* (2006.01)
*C07D 295/02* (2006.01)
*C07D 417/14* (2006.01)
*C07D 471/04* (2006.01)

(52) U.S. Cl.
CPC ......... *C07D 417/14* (2013.01); *C07D 471/04* (2013.01)

(58) Field of Classification Search
CPC .......................... A61K 31/4025; C07D 295/02
USPC ......... 514/429; 544/324, 405; 546/118, 307; 548/128, 202, 235, 364.1, 577; 549/505
See application file for complete search history.

(56) References Cited

U.S. PATENT DOCUMENTS

| 2003/0064996 A1 | 4/2003 | Bilodeau et al. |
| 2009/0306116 A1 | 12/2009 | Thomas et al. |
| 2012/0015969 A1 | 1/2012 | Binch et al. |
| 2015/0051190 A1 | 2/2015 | Takeda et al. |

FOREIGN PATENT DOCUMENTS

| CA | 2872645 | * | 12/2013 |
| WO | 01/17995 A1 | | 3/2001 |
| WO | 2007/031745 A1 | | 3/2007 |
| WO | 2010/093928 A2 | | 8/2010 |
| WO | 2010/111056 A1 | | 9/2010 |
| WO | 2012/005299 A1 | | 1/2012 |
| WO | 2013/017989 A1 | | 2/2013 |

OTHER PUBLICATIONS

Jordan, V. C. Nature Reviews: Drug Discovery, 2, 2003, 205.*
Hackam, et al. JAMA, 296(14), 2006, 1731-1732.*
Jaime Acquaviva et al., "The multifaceted roles of the receptor tyrosine kinase ROS in development and cancer," Biochimica et Biophysica Acta, 1795, pp. 37-52 (2009), Elsevier B.V.
Ashley H. Birch et al., "Chromosome 3 Anomalies Investigated by Genome Wide SNP Analysis of Benign, Low Malignant Potential and Low Grade Ovarian Serous Tumours," PLoS ONE, vol. 6, Issue 12, e28250, pp. 1-20 (Dec. 2011).
Emma Bowden, et al., "A survey of thousands of tumor exomes and transcriptomes to expand clinical opportunities for crizotinib," Journal of Clinical Oncology, 2013 ASCO Annual Meeting, vol. 31, No. 15_suppl (May 20 Supplement), 11017, 2013 American Society of Clinical Oncology.
Alain Charest, et al., "Fusion of FIG to the Receptor Tyrosine Kinase ROS in a Glioblastoma with an Interstitial del (6)(q21q21)," Genes, Chromosomes & Cancer, 37, pp. 58-71 (2003), Wiley-Liss, Inc.
Alan Charest et al., "Oncogenic Targeting of an Activated Tyrosine Kinase to the Golgi Apparatus in a Glioblastoma," PNAS, vol. 100, No. 3, pp. 916-921 (Feb. 4, 2003).
Daniela Cilloni et al., "Identification of the Involvement of the Tyrosine Kinase C-Ros in the Pathogenesis of Chronic Myelomonocytic Leukemia (CMML)," Blood, 112: Abstract 687 (2008), American Society of Hematology.
Minseob Eom et al., "ROS1 Expression in Invasive Ductal Carcinoma of the Breast Related to Proliferation Activity," Yonsei Med J, vol. 54, No. 3, pp. 650-657 (May 2013).
Craig P. Giacomini et al., "Breakpoint Analysis of Transcriptional and Genomic Profiles Uncovers Novel Gene Fusions Spanning Multiple Human Cancer Types," PLOS Genetics, vol. 9, Issue 4, e1003464, pp. 1-19 (Apr. 2013).
Ramaswamy Govindan et al., "Genomic Landscape of Non-Small Cell Lung Cancer in Smokers and Never-Smokers," Cell, vol. 150 (6), pp. 1121-1134 (Sep. 2012), Elsevier Inc.
Ting-Lei Gu et al., "Survey of Tyrosine Kinase Signaling Reveals ROS Kinase Fusions in Human Cholangiocarcinoma," PLoS One, vol. 6, Issue 1, e15640, pp. 1-9 (Jan. 2011).

(Continued)

*Primary Examiner* — Douglas M Willis

(57) ABSTRACT

The main purpose of the invention is to provide a novel aromatic heterocyclic derivative or a pharmaceutically acceptable salt thereof. Examples of the invention include aromatic heterocyclic derivatives represented by general formula [1] and pharmaceutically acceptable salts thereof.

[1]

In formula [1]: $R^1$ represents phenyl optionally substituted with one or two groups selected from the group consisting of halogens, as well as alkyls and alkoxys optionally substituted by halogens; $R^2$ represents hydrogen, an alkyl, cycloalkyl, or alkoxy optionally substituted by a halogen, or a heteroaryl optionally substituted by an alkyl; X represents $CR^3$, and Y represents N or $CR^4$, or X represents N, and Y represents $CR^4$; and Z represents $CR^5$ or N.

23 Claims, No Drawings

(56) References Cited

OTHER PUBLICATIONS

Kousuke Hamal et al., "Expression of ROS1 in interstitial pneumonia," Abstract, Nihon Kokyuuki Gakkai Zasshi 2, 158 (2013).
Takefumi Komiyama et al., "Response to Crizotinib in ROS1-Rearranged Non-Small-Cell Lung Cancer," Journal of Clinical Oncology, pp. 3425-3426 (2012), American Society of Clinical Oncology.
Jeeyun Lee et al., "Identification of ROS1 rearrangement in gastric adenocarcinoma," Cancer, pp. 1627-1635 (May 1, 2013).
Christine Marie Lovly et al., "Potentially Actionable Kinase Fusions in Inflammatory Myofibroblastic Tumors," Journal of Clinical Oncology, 2013 ASCO Annual Meeting Abstracts, vol. 31, No. 15_suppl (May 20 Supplement), 10513, 2013 American Society of Clinical Oncology.
Hitoshi Matsushime et al., "Human c-ros-1 Gene Homologous to the v-ros Sequence of UR2 Sarcoma Virus Encodes for a Transmembrane Receptorlike Molecule," Molecular and Cellular Biology, vol. 6, No. 8, pp. 3000-3004 (Aug. 1986).
Eva Sonnenberg-Riethmacher et al., "The c-ros tyrosine kinase receptor controls regionalization and differentiation of epithelial cells in the epididymis," Genes & Development, 10, pp. 1184-1193 (1996), Cold Spring Harbor Laboratory Press.
Klarisa Rikova et al., "Global Survey of Phosphotyrosine Signaling Identifies Oncogenic Kinases in Lung Cancer," Cell, 131, pp. 1190-1203 (Dec. 14, 2007), Elsevier Inc.
Jeong-Sun Seo, "The transcriptional landscape and mutational profile of lung adenocarcinoma," Genome Research, pp. 2109-2119 (2012), Cold Spring Harbor Laboratory Press.
Phil Stephens et al., "Next-generation sequencing of genomic and cDNA to identify a high frequency of kinase fusions involving ROS1, ALK, RET, NTRK1, and BRAF in Spitz tumors," Journal of Clinical Oncology, 2013 ASCO Annual Meeting Abstracts, vol. 31, No. 15_suppl (May 20 Supplement), 9002, 2013 American Society of Clinical Oncology.
Yoshiyuki Suehara et al., "Identification of KIF5B-RET and GOPC-ROS1 Fusions in Lung Adenocarcinomas Through a Comprehensive mRNA-based Screen for Tyrosine Kinase Fusions," Clinical Cancer Research, 18 (24), pp. 6599-6608 (Dec. 2012), American Association for Cancer Research.
Kengo Takeuchi et al., "RET, ROS1 and ALK fusions in lung cancer," Nature Medicine, vol. 18, No. 3, pp. 378-381 (Mar. 2012), Advance Online Publication.
David Watkins, et al., "Analysis of Oncogene Expression in Primary Human Gliomas: Evidence for Increased Expression of the ros Oncogene," Cancer Genetics and Cytogenetics, vol. 72, pp. 130-136 (1994), Elsevier Science Inc.
Andrew James Weickhardt et al., "ALK and ROS1 gene rearrangements detected in colorectal cancer (CRC) by fluorescence in situ hybridization (FISH)," Journal of Clinical Oncology, 2013 ASCO Annual Meeting Abstracts, vol. 31, No. 15_Suppl (May 20 Supplement), 3545, 2013 American Society of Clinical Oncology.
Ching-Hei Yeung et al., "The Cause of Infertility of Male c-ros Tyrosine Kinase Receptor Knockout Mice," Biology of Reproduction, vol. 63, pp. 612-618 (2000), the Science for the Study of Reproduction, Inc.
Jing-Feng Zhao et al., "Expression of the ROS1 Oncogene for Tyrosine Receptor Kinase in Adult Human Meningiomas," Cancer Genet Cytogenet, vol. 83, pp. 148-154 (1995), Elsevier Science Inc.

\* cited by examiner

SUBSTITUTED PYRROLIDINES AS ROS TYROSINE KINASE INHIBITORS

CROSS REFERENCE TO RELATED APPLICATIONS

This patent application is a U.S. national stage application under 35 U.S.C. §371 of International Patent Application No. PCT/JP2013/064933 filed on May 29, 2013, which claims the benefit of foreign priority to Japanese Patent Application No. JP 2012-122715 filed on May 30, 2012, the disclosures of all of which are hereby incorporated by reference in their entireties. The International Application was published in Japanese on Dec. 5, 2013, as International Publication No. WO 2013/180183 A1 under PCT Article 21(2).

FIELD OF THE INVENTION

The present invention relates to a novel aromatic heterocyclic derivative and a pharmaceutical composition containing the same as an active ingredient.

BACKGROUND OF THE INVENTION

ROS tyrosine kinase is a receptor-type protein tyrosine kinase similar to the EGF receptor, and it is considered that the ROS tyrosine kinase participates in signal transduction relative to proliferation and differentiation of cells (see, for example, Non-Patent Document 1).

Up to date, changes in the gene expression level of the ROS tyrosine kinase in some malignant tumors have been reported. For example, overexpression of the ROS tyrosine kinase is reported in glioma, meningioma, infiltrating ductal carcinoma, and so on (see, for example, Non-Patent Documents 2, 3 and 4), and chronic myelomonocytic leukemia (see, for example, Non-Patent Document 5).

In addition, there are found: FIG-ROS fusion gene in a glioblastoma cell line (see, for example, Non-Patent Document 6); SLC34A2-ROS fusion gene in a non-small cell lung cancer cell line (see, for example, Non-Patent Document 7); CD74-ROS fusion gene, FIG-ROS fusion gene, TPM3-ROS fusion gene, SDC4-ROS fusion gene, EZR-ROS fusion gene, LRIG3-ROS fusion gene, CCDC6-ROS fusion gene, and KDELR2-ROS fusion gene in non-small cell lung cancer clinical specimens (see, for example, Patent Documents 7, 8, 9, 10 and 11); FIG-ROS fusion gene in cholangiocarcinoma clinical specimens (see, for example, Non-Patent Document 12); FIG-ROS fusion gene in ovarian cancer clinical specimens (see, for example, Non-Patent Document 13); SLC34A2-ROS fusion gene in gastric cancer clinical specimens (see, for example, Non-Patent Document 14); CEP85L-ROS fusion gene in angiosarcoma clinical specimens (see, for example, Non-Patent Document 15); and YWHAE-ROS fusion gene and TFG-ROS1 fusion gene in inflammatory myofibroblastic tumor clinical specimens (see, for example, Non-Patent Document 16). It is reported that these fusion genes are oncogenes (see, for example, Non-Patent Documents 9 and 17). In addition, the ROS tyrosine kinase is a homologue of the transforming gene v-ros of the avian sarcoma virus (see, for example, Non-Patent Document 18), and it is considered that activation of the ROS tyrosine kinase is associated with oncogenesis.

Furthermore, even in liver cancer, kidney cancer, pancreatic cancer, testicular cancer (see, for example, Non-Patent Document 1), epithelioid hemangioendothelioma (see, for example, Non-Patent Document 15), colorectal cancer (see, for example, Non-Patent Document 19), liposarcoma, breast cancer (see, for example, Non-Patent Document 20), and Spitzoid neoplasms (see, for example, Non-Patent Document 21), a possibility of the presence of ROS fusion genes or occurrence of abnormality in the ROS tyrosine kinase is suggested.

Recently, it has been reported that crizotinib, which is a medicine having ROS inhibitory activity, is effective for patients of non-small cell lung cancer with ROS fusion gene positive in the clinical application (see, for example, Non-Patent Document 22).

From the foregoing, it is considered that the ROS tyrosine kinase inhibitor is effective as a treating agent for the malignant tumors as described previously.

In addition, overexpression of an ROS tyrosine kinase is seen in interstitial pneumonia, and a possibility that the ROS tyrosine kinase plays an important role for the onset of interstitial pneumonia is suggested (see, for example, Non-Patent Document 23); and a possibility that the ROS tyrosine kinase inhibitor is effective for the interstitial pneumonia is considered. Furthermore, in view of the fact that ROS tyrosine kinase knockout male mice are male infertile, a possibility that the ROS tyrosine kinase inhibitor is effective as a male contraceptive is considered (see, for example, Non-Patent Documents 24 and 25).

PRIOR ART REFERENCES

Patent Documents

Patent document 1: WO2010/093928 A2

Non-Patent Documents

Non-patent document 1: Jamie Acquaviva, et al., 2009, Biochimicaet Biophysica Acta, 1795, 37-52
Non-patent document 2: David Watkins, et al., 1994, Cancer Genet Cytogenet, 72, 130-136
Non-patent document 3: Jing-FengZhao, et al., 1995, Cancer Genet Cytogenet, 83, 148-154
Non-patent document 4: Minseob Eom, et al., 2013, Yonsei Medical Journal, 54, 650-657
Non-patent document 5: Daniela Cilloni, et al., 2008, Annual meeting of American Society of Hematology Abstract, 112, 687
Non-patent document 6: Alain Charest, et al., 2003, Genes, Chromosomes & Cancer, 37, 58-71
Non-patent document 7: Klarisa Rikova, et al., 2007, Cell, 131, 1190-1203
Non-patent document 8: Yoshiyuki Suehara, et al., 2012, Clinical Cancer Research,
Non-patent document 9: Kengo Takeuchi, et al., 2012, Nature Medicine, 18, 378-381
Non-patent document 10: Jeong-Sun Seo, et al., 2012, Genome Research, 22, 2109-2119
Non-patent document 11: Ramaswamy Govindan, et al., 2012, Cell, 150, 1121-1134
Non-patent document 12: Gu Ting-Lei, et al., 2011, PLoSONE, 6, e15640
Non-patent document 13: Ashley H. Birch, et al., 2011, PLoSONE, 6, e28250
Non-patent document 14: Jeeyun Lee, et al., 2013, Cancer, 119, 1627-1635
Non-patent document 15: Craig P Giacomini, et al., 2013, PLOS Genetics, 9, e1003464
Non-patent document 16: Christine Marie Lovly, et al., 2013, Journal of Clinical Oncology, Abstract, 31, 10513

Non-patent document 17: Alain Charest, et al., 2003, Proceedings of the National Academy of Sciences, 100, 916-921

Non-patent document 18: Hitoshi Matsushime, et al., 1986, Molecular and Cellular Biology, 6, 3000-3004

Non-patent document 19: ANDREW James Weickhardt, et al., 2013, Journal of Clinical Oncology, Abstract, 31, 3545

Non-patent document 20: Emma Bowden, et al., 2013, Journal of Clinical Oncology, Abstract, 31, 11017

Non-patent document 21: Phil Stephens, et al., 2013, Journal of Clinical Oncology, Abstract, 31, 9002

Non-patent document 22: Takefumi Komiya, et al., 2012, Journal of Clinical Oncology, 30, 3425-3426

Non-patent document 23: Kousuke Hamai, et al., 2013, Nihon Kokyuuki Gakkai Zasshi, 2, 158

Non-patent document 24: Eva Sonnenberg-Riethmacher, et al., 1996, Gene Development, 10, 1184-1193

Non-patent document 25: Ching-Hei Yeung, et al., 2000, Biology of Reproduction, 63, 612-618

BRIEF SUMMARY OF THE INVENTION

Problem to be Solved by the Invention

A primary object of the present invention is to provide a novel aromatic heterocyclic derivative or a pharmaceutically acceptable salt thereof. In addition, another primary object of the present invention is to provide a pharmaceutical composition containing such an aromatic heterocyclic derivative or its pharmaceutically acceptable salt as an active ingredient.

Means for Solving the Problems

The present invention is directed to an aromatic heterocyclic derivative that is a compound represented by the following general formula [1] (hereinafter referred to as "compound of the present invention") or a pharmaceutically acceptable salt thereof.

[Chemical formula 1]

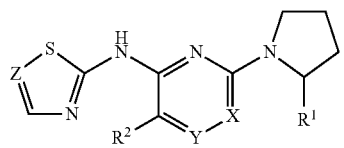

[1]

In the formula:

$R^1$ represents phenyl which may be substituted with one or two groups selected from the group consisting of halogen, alkyl optionally substituted by halogen, and alkoxy.

$R^2$ represents hydrogen, alkyl optionally substituted by halogen, cycloalkyl, alkoxy, halogen, or heteroaryl optionally substituted by alkyl.

X represents $CR^3$, and Y represents N or $CR^4$, or X represents N, and Y represents $CR^4$.

$R^3$ represents hydrogen or alkyl.

$R^4$ represents
1) hydrogen,
2) alkyl which may be substituted with 1 to 3 groups selected from the group consisting of alkoxy and halogen,
3) cycloalkyl,
4) phenyl which may be substituted with one group selected from the group consisting of carbamoyl and alkylsulfonyl,
5) heteroaryl which may be substituted with one group selected from alkyl optionally substituted by hydroxyl or alkoxy, halogen, hydroxyl, and alkoxy,
6) carboxyl,
7) alkyloxycarbonyl, or
8) carbamoyl which may be substituted with one or two groups selected from the group consisting of alkyl optionally substituted by hydroxyl or alkoxy, alkylsulfonyl, saturated heterocyclic group optionally substituted by alkyl, and cycloalkyl optionally substituted by hydroxyl or carboxyl. In addition, in the case where X is N, and Y is $CR^4$, $R^2$ and $R^4$ may be taken jointly to form a group represented by the following general formula, together with the carbon atom to which $R^2$ bonds as well as the carbon atom to which $R^1$ bonds.

[Chemical formula 2]

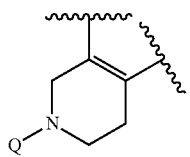

(In the formula, Q represents alkylcarbonyl or alkylsulfonyl.)

Z represents $CR^5$ or N, and $R^5$ represents alkyl, alkoxycarbonyl, halogen, or cyano.

Above all, the compound of the present invention, wherein Z is $CR^5$, and such $R^5$ is cyano, or a pharmaceutically acceptable salt thereof is preferable.

In addition, the compound of the present invention, wherein $R^1$ is phenyl substituted with alkyl, or a pharmaceutically acceptable salt thereof is preferable.

In addition, the compound of the present invention, wherein Y is $CR^4$, or a pharmaceutically acceptable salt thereof is preferable.

In addition, the compound of the present invention, wherein X is N, or a pharmaceutically acceptable salt thereof is preferable.

In addition, the compound of the present invention, wherein X is N, and Y is $CR^4$, and (1) $R^2$ is alkyl or alkoxy, or (2) $R^2$ and $R^4$ are taken jointly to form a group represented by the following general formula, together with the carbon atom to which $R^2$ bonds as well as the carbon atom to which $R^4$ bonds, or a pharmaceutically acceptable salt thereof is preferable.

[Chemical formula 3]

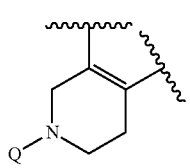

(In the formula, Q is synonymous with that described above.)

A specific example of the compound of the present invention includes the following (1)-(72).

(1) 2-({6-[2-(4-methylphenyl)pyrrolidin-1-yl]pyrazin-2-yl}amino)-1,3-thiazole-5-carbonitrile,
(2) 2-({5-methyl-2-[2-(4-methylphenyl)pyrrolidin-1-yl]pyrimidin-4-yl}amino)-1,3-thiazole-5-carbonitrile,
(3) 2-({5-methoxy-2-[2-(4-methylphenyl)pyrrolidin-1-yl]-4,5'-bipyrimidin-6-yl}amino)-1,3-thiazole-5-carbonitrile,
(4) 4-{6-[(5-cyano-1,3-thiazol-2-yl)amino]-5-methoxy-2-[2-(4-methylphenyl)pyrrolidin-1-yl]pyrimidin-4-yl}benzamide,
(5) 2-({5-methoxy-2-[2-(4-methylphenyl)pyrrolidin-1-yl]-6-(pyridin-3-yl)pyrimidin-4-yl}amino)-1,3-thiazole-5-carbonitrile,
(6) methyl 6-[(5-cyano-1,3-thiazol-2-yl)amino]-2-[2-(4-methylphenyl) pyrrolidin-1-yl]pyrimidine-4-carboxylate,
(7) 6-[(5-cyano-1,3-thiazol-2-yl)amino]-2-[2-(4-methylphenyl) pyrrolidin-1-yl]pyrimidine-4-carboxylic acid,
(8) 2-({5-methyl-2-[2-(4-methylphenyl)pyrrolidin-1-yl]-6-(1-n ethyl-1H-pyrazol-4-yl)pyrimidin-4-yl}amino)-1,3-thiazole-5-carbonitrile,
(9) 2-({5-methoxy-6-methyl-2-[2-(4-methylphenyl)pyrrolidin-1-yl]pyrimidin-4-yl}amino)-1,3-thiazole-5-carbonitrile,
(10) 2-({5-methoxy-2-[2-(4-methylphenyl)pyrrolidin-1-yl]-6-(1-methyl-1H-pyrazol-4-yl)pyrimidin-4-yl}amino)-1,3-thiazole-5-carbonitrile,
(11) 2-({5-methoxy-2-[(2-(4-methylphenyl)pyrrolidin-1-yl]-6-(1,3-oxazol-5-yl)pyrimidin-4-yl}amino)-1,3-thiazole-5-carbonitrile,
(12) 6-[(5-cyano-1,3-thiazol-2-yl)amino]-N-[(2R)-1-hydroxypropan-2-yl]-2-[2-(4-methylphenyl)pyrrolidin-1-yl]pyrimidine-4-carboxamide,
(13) 2-({5-methoxy-2-[(2-(4-methylphenyl)pyrrolidin-1-yl]-6-[4-(methylsulfonyl)phenyl]pyrimidin-4-yl}amino)-1,3-thiazole-5-carbonitrile,
(14) 2-({5-methoxy-2-[2-(2-methoxy-4-methylphenyl)pyrrolidin-1-yl]pyrimidin-4-yl}amino)-1,3-thiazole-5-carbonitrile,
(15) 2-({6-(6-methoxypyridin-3-yl)-5-methyl-2-[2-(4-methylphenyl)pyrrolidin-1-yl]pyrimidin-4-yl}amino)-1,3-thiazole-5-carbonitrile,
(16) 2-({6-(6-hydroxypyridin-3-yl)-5-methyl-2-[2-(4-methylphenyl)pyrrolidin-1-yl]pyrimidin-4-yl}amino)-1,3-thiazole-5-carbonitrile,
(17) 2-({5-bromo-6-methyl-2-[2-(4-methylphenyl)pyrrolidin-1-yl]pyrimidin-4-yl}amino)-1,3-thiazole-5-carbonitrile,
(18) 2-({6-cyclopropyl-5-methoxy-2-[(2-(4-methylphenyl) pyrrolidin-1-yl]pyrimidin-4-yl}amino)-1,3-thiazole-5-carbonitrile,
(19) 2-({5-methoxy-2-[2-(4-methylphenyl)pyrrolidin-1-yl] pyrimidin-4-yl}amino)-1,3-thiazole-5-carbonitrile,
(20) 2-({3-methyl-6-[2-(4-methylphenyl)pyrrolidin-1-yl] pyrazin-2-yl}amino)-1,3-thiazole-5-carbonitrile,
(21) 2-({6-[2-(4-fluorophenyl)pyrrolidin-1-yl]-3-(1,3-oxazol-5-yl)pyrazin-2-yl}amino)-1,3-thiazole-5-carbonitrile,
(22) 2-({6-[2-(4-fluorophenyl)pyrrolidin-1-yl]-3-(pyrimidin-5-yl)pyrazin-2-yl}amino)-1,3-thiazole-5-carbonitrile,
(23) 2-({3-cyclopropyl-6-[2-(2-methoxy-4-methylphenyl) pyrrolidin-1-yl]pyrazin-2-yl}amino)-1,3-thiazole-5-carbonitrile,
(24) 2-({3-cyclopropyl-6-[2-(2-methoxyphenyl)pyrrolidin-1-yl]pyrazin-2-yl}amino)-1,3-thiazole-5-carbonitrile,
(25) 2-({6-[2-(4-fluorophenyl)pyrrolidin-1-yl]-3-(furan-3-yl)pyrazin-2-yl}amino)-1,3-thiazole-5-carbonitrile,
(26) 2-({6-[2-(4-fluorophenyl)pyrrolidin-1-yl]-3-(pyridin-4-yl)pyrazin-2-yl}amino)-1,3-thiazole-5-carbonitrile,
(27) 2-({6-[2-(4-methylphenyl)pyrrolidin-1-yl]-4-(trifluoromethyl)pyridin-2-yl}amino)-1,3-thiazole-5-carbonitrile,
(28) 2-({6-[2-(4-fluorophenyl)pyrrolidin-1-yl]-3-(1-methyl-1H-pyrazol-4-yl)pyrazin-2-yl}amino)-1,3-thiazole-5-carbonitrile,
(29) 3-methyl-6-[2-(4-methylphenyl)pyrrolidin-1-yl]-N-(5-methyl-1,3-thiazol-2-yl) pyrazine-2-amine,
(30) 2-({6-[2-(2-methoxy-4-methylphenyl)pyrrolidin-1-yl] pyrazin-2-yl}amino)-1,3-thiazole-5-carbonitrile,
(31) 6-[2-(4-chiorophenyl)pyrrolidin-1-yl]-3-cyclopropyl-N-(5-methyl-1,3-thiazol-2-yl)pyrazine-2-amine,
(32) 2-({6-[2-(3,5-dimethoxyphenyl)pyrrolidin-1-yl] pyrazin-2-yl}amino)-1,3-thiazol-5-carbonitrile,
(33) 2-({6-[2-(3-methoxy-4-methylphenyl)pyrrolidin-1-yl] pyrazin-2-yl}amino)-1,3-thiazole-5-carbonitrile,
(34) 3-cyclopropyl-6-[2-(4-methylphenyl)pyrrolidin-1-yl]-N-(5-methyl-1,3-thiazol-2-yl) pyrazine-2-amine,
(35) 2-({3-cyclopropyl-6-[2-(4-methylphenyl)pyrrolidin-1-yl]pyrazin-2-yl}amino)-1,3-thiazole-5-carbonitrile,
(36) 2-({6-[2-(4-chlorophenyl)pyrrolidin-1-yl]-3-cyclopropylpyrazin-2-yl}amino)-1,3-thiazole-5-carbonitrile,
(37) 2-({6-[2-(4-methoxyphenyl)pyrrolidin-1-yl]pyrazin-2-yl}amino)-1,3-thiazole-5-carbonitrile,
(38) 2-({6-[2-(3-methoxyphenyl)pyrrolidin-1-yl]pyrazin-2-yl}amino)-1,3-thiazole-5-carbonitrile,
(39) 2-[(6-{2-[4-(trifluoromethyl)phenyl]pyrrolidin-1-yl}pyrazin-2-yl)amino]-1,3-thiazole-5-carbonitrile,
(40) 2-({3-cyclopropyl-6-[2-(4-fluorophenyl)pyrrolidin-1-yl]pyrazin-2-yl}amino)-1,3-thiazole-5-carbonitrile,
(41) 2-({6-[2-(4-fluorophenyl)pyrrolidin-1-yl]-3-methylpyrazin-2-yl}amino)-1,3-thiazole-5-carbonitrile,
(42) 2-({6-[2-(4-chlorophenyl)pyrrolidin-1-yl]-3-methylpyrazin-2-yl}amino)-1,3-thiazole-5-carbonitrile,
(43) 2-({3,5-dimethyl-6-[2-(4-methylphenyl)pyrrolidin-1-yl]pyrazin-2-yl}amino)-1,3-thiazole-5-carbonitrile,
(44) 2-({6-[2-(4-chlorophenyl)pyrrolidin-1-yl]-3-cyclopropyl-5-methylpyrazin-2-yl}amino)-1,3-thiazole-5-carbonitrile,
(45) N-(5-ethyl-1,3-thiazol-2-yl)-6-[2-(4-methylphenyl)pyrrolidin-1-yl]pyrazine-2-amine,
(46) 2-({6-[2-(3-methylphenyl)pyrrolidin-1-yl]pyrazin-2-yl}amino)-1,3-thiazole-5-carbonitrile,
(47) 2-({6-[2-(2-methylphenyl)pyrrolidin-1-yl]pyrazin-2-yl}amino)-1,3-thiazole-5-carbonitrile,
(48) 2-({6-[2-(4-chlorophenyl)pyrrolidin-1-yl]pyrazin-2-yl}amino)-1,3-thiazole-5-carbonitrile,
(49) 2-({6-(2-fluoropyridin-3-yl)-5-methoxy-2-[2-(4-methylphenyl)pyrrolidin-1-yl]pyrimidin-4-yl}amino)-1,3-thiazole-5-carbonitrile,
(50) 2-({6-(6-fluoropyridin-3-yl)-5-methoxy-2-[2-(4-methylphenyl)pyrrolidin-1-yl]pyrimidin-4-yl})amino)-1,3-thiazole-5- carbonitrile,
(51) ethyl 2-({6-[2-(4-methylphenyl)pyrrolidin-1-yl] pyrazin-2-yl}amino)-1,3-thiazole-5-carboxylate,
(52) 2-({5,6-dimethyl-2-[2-(4-methylphenyl)pyrrolidin-1-yl]pyrimidin-4-yl}amino)-1,3-thiazole-5-carbonitrile,
(53) 2-({6-[2-(4-fluorophenyl)pyrrolidin-1-yl]-3-(2-methylpyridin-4-yl)pyrazin-2-yl}amino)-1,3-thiazole-5-carbonitrile,
(54) 6-[(5-cyano-1,3-thiazol-2-yl)amino]-5-methyl-2-[2-(4-methylphenyl)pyrrolidin-1-yl]-N-(1-methylpiperidin-4-yl)pyrimidine-4-carboxamide,

(55) 2-[(5-cyano-1,3-thiazol-2-yl)amino]-N,3-dimethyl-6-[2-(4-methylphenyl)pyrrolidin-1-yl]pyridine-4-carboxamide,

(56) N-(5-fluoro-1,3-thiazol-2-yl)-5-methoxy-6-methyl-2-[2-(4-methylphenyl)pyrrolidin-1-yl]pyrimidine-4-amine,

(57) 2-({5-ethyl-6-(methoxymethyl)-2-[2-(4-methylphenyl)pyrrolidin-1-yl]pyrimidin-4-yl}amino)-1,3-thiazole-5-carbonitrile,

(58) 2-({5-methoxy-6-[1-(2-methoxyethyl)-1H-pyrazol-4-yl]-2-[2-(4-methylphenyl)pyrrolidin-1-yl]pyrimidin-4-yl}amino)-1,3-thiazole-5-carbonitrile,

(59) 2-({6-[1-(2-hydroxyethyl)-1H-pyrazol-4-yl]-5-methoxy-2-[2-(4-methylphenyl)pyrrolidin-1-yl]pyrimidin-4-yl}amino)-1,3-thiazole-5-carbonitrile,

(60) 2-({5-methoxy-2'-methyl-2-[2-(4-methylphenyl)pyrrolidin-1-yl]-4,5'-bipyrimidin-6-yl}amino)-1,3-thiazole-5-carbonitrile,

(61) 2-(4-{5-methoxy-2-[2-(4-methylphenyl)pyrrolidin-1-yl]-6-(1,2,4-thiadiazol-5-ylamino)pyrimidin-4-yl}-1H-pyrazol-1-yl)ethanol,

(62) 6-[(5-cyano-1,3-thiazol-2-yl)amino]-N-(trans-4-hydroxycyclohexyl)-5-methoxy-2-[2-(4-methylphenyl)pyrrolidin-1-yl]pyrimidine-4-carboxamide,

(63) trans-4-[({6-[(5-cyano-1,3-thiazol-2-yl)amino]-5-methoxy-2-[2-(4-methylphenyl)pyrrolidin-1-yl]pyrimidin-4-yl}carbonyl)amino]cyclohexanecarboxylic acid,

(64) 6-[(5-cyano-1,3-thiazol-2-yl)amino]-5-methoxy-N-(2-methoxyethyl)-2-[2-(4-methylphenyl)pyrrolidin-1-yl]pyrimidine-4-carboxamide,

(65) 2-({6-(6-hydroxypyridin-3-yl)-5-methoxy-2-[2-(4-methylphenyl)pyrrolidin-1-yl]pyrimidin-4-yl}amino)-1,3-thiazole-5-carbonitrile,

(66) 2-[(5-cyano-1,3-thiazol-2-yl)amino]-3-cyclopropyl-6-[2-(4-methylphenyl)pyrrolidin-1-yl]pyridine-4-carboxamide,

(67) 6-[(5-cyano-1,3-thiazol-2-yl)amino]-5-ethyl-2-[2-(4-methylphenyl)pyrrolidin-1-yl]-N-(methylsulfonyl)pyrimidine-4-carboxamide,

(68) 2-[(5-cyano-1,3-thiazol-2-yl)amino]-N-(4-hydroxycyclohexyl)-3-methyl-6-[2-(4-methylphenyl)pyrrolidin-1-yl]pyridine-4-carboxamide,

(69) 6-[2-(4-methylphenyl)pyrrolidin-1-yl]-4-(1-methyl-1H-pyrazol-4-yl)-N-(1,2,4-thiadiazol-5-yl)pyridine-2-amine,

(70) 2-({5-ethyl-6-methyl-2-[2-(4-methylphenyl)pyrrolidin-1-yl]pyrimidin-4-yl}amino)-1,3-thiazole-5-carbonitrile,

(71) 2-({6-acetyl-2-[2-(4-methylphenyl)pyrrolidin-1-yl]-5,6,7,8-tetrahydropyrido[4,3-d]pyrimidin-4-yl}amino)-1,3-thiazole-5-carbonitrile, and

(72) 2-({2-[2-(4-methylphenyl)pyrrolidin-1-yl]-6-(methylsulfonyl)-5,6,7,8-tetrahydropyrid[4,3-d]pyrimidin-4-yl}amino)-1,3-thiazole-5-carbonitrile.

The compound of the present invention, wherein the carbon atom to which $R^1$ bonds is of an S-configuration, is preferable.

The following will describe in detail each term concerned in the invention.

"Alkyl" means, for example, a straight or branched chain alkyl having 1 to 8 carbons, specifically including methyl, ethyl, n-propyl, isopropyl, n-butyl, isobutyl, sec-butyl, tert-butyl, n-pentyl, isopentyl, n-hexyl, isohexyl, n-heptyl, isoheptyl, and n-octyl. In particular, those having 1 to 6 carbons are preferred, and those having 1 to 3 carbons more preferred.

The alkyl moiety of "alkylcarbonyl", "monoalkylaminocarbonyl", "dialkylaminocarbonyl", "alkylsulfonyl" and "alkyloxycarbonyl" can be exemplified by the same ones as the above-described "alkyl".

"Alkoxy" means, for example, a straight or branched chain alkoxy having 1 to 8 carbons, specifically including methoxy, ethoxy, n-propoxy, isopropoxy, n-butoxy, isobutoxy, sec-butoxy, t-butoxy, n-pentyloxy, n-hexyloxy, n-heptyloxy, and n-octyloxy.

The alkoxy moiety of "alkoxycarbonyl" is exemplified by the same ones as the above "alkoxy".

"Cycloalkyl" means, for example, those having 3 to 8 carbons, specifically including cyclopropyl, cyclobutyl, cyclopentyl, cyclohexyl, cycloheptyl, and cyclooctyl.

"Halogen" includes, for example, fluorine, chlorine, bromine and iodine.

"Heteroaryl" means, for example, 5- or 6-membered heteroaryl containing 1 to 4 of N, O and S as ring-constituting atom(s), specifically including, for example, furyl (e.g. 2-furyl, 3-furyl), thienyl (e.g. 2-thienyl, 3-thienyl), pyrrolyl (e.g. 1-pyrrolyl, 2-pyrrolyl, 3-pyrrolyl), imidazolyl (e.g. 1-imidazolyl, 2-imidazolyl, 4-imidazolyl), pyrazolyl (e.g. 1-pyrazolyl, 3-pyrazolyl, 4-pyrazolyl), triazolyl (e.g. 1,2,4-triazol-1-yl, 1,2,4-triazol-3-yl, 1,2,4-triazolyl-4-yl), tetrazolyl (e.g. 1-tetrazolyl, 2-tetrazolyl, 5-tetrazolyl), oxazolyl (e.g. 2-oxazolyl, 4-oxazolyl, 5-oxazolyl), isoxazolyl (e.g. 3-isoxazolyl, 4-isoxazolyl, 5-isoxazolyl), oxadiazolyl (e.g. 1,3,4-oxadiazol-2-yl), thiazolyl (e.g. 2-thiazolyl, 4-thiazolyl, 5-thiazolyl), thiadiazolyl, isothiazolyl (e.g. 3-isothiazolyl, 4-isothiazolyl, 5-isothiazolyl), pyridyl (e.g. 2-pyridyl, 3-pyridyl, 4-pyridyl), pyridazinyl (e.g. 3-pyridazinyl, 4-pyridazinyl), pyrimidinyl (e.g. 2-pyrimidinyl, 4-pyrimidinyl, 5-pyrimidinyl), and pyrazinyl (e.g. 2-pyrazinyl). In particular, pyridyl, pyrimidinyl, furyl, pyrazolyl and oxazolyl are preferred, and 3-pyridyl, 4-pyridyl, 4-pyrimidinyl, 3-furyl, 4-pyrazolyl and 5-oxazolyl are more preferred.

"Saturated heterocyclic group" means, for example, a 5- or 6-membered saturated heterocyclic group containing 1 or 2 of N, O and S as ring-constituting atom(s), specifically including, for example, 2-pyrrolidinyl, 3-pyrrolidinyl, 2-piperidinyl, 3-piperidinyl, 4-piperidinyl, tetrahydropyranyl, and tetrahydrothiopyranyl.

DETAILED DESCRIPTION OF THE INVENTION

The compound of the present invention can be, for example, produced from a known compound or an easily synthesizable intermediate according to the following method. In the production of the compound of the present invention, in the case where a raw material has a substituent which influences the reaction, it is general to perform the reaction after protecting the raw material with a suitable protective group in advance by a known method. The protective group can be removed after the reaction by a known method.

Production Method 1

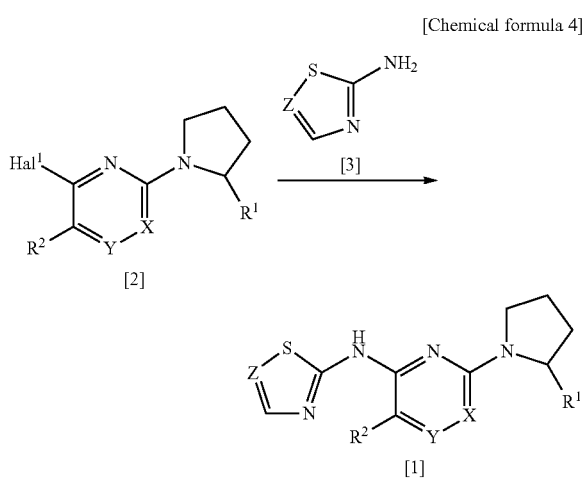

($R^1$, $R^2$, X, Y, and Z are synonymous with those described above; and $Hal^1$ represents halogen.)

The compound of the present invention can be produced by subjecting a compound represented by the foregoing general formula [2] (hereinafter referred to as "compound [2]") and a compound represented by the foregoing general formula [3](hereinafter referred to as "compound [3]") to a condensation reaction by using a palladium catalyst and a ligand. The present reaction is performed in the presence of a base at a temperature in the range of from 20° C. to 200° C. by using microwaves as necessary. An amount of the compound [3] which may be used is suitably in the range of from 1.0 mole to 5.0 moles per mole of the compound [2]. Although a solvent which may be used is not particularly limited so long as it does not participate in the reaction, for example, there can be exemplified hydrocarbons such as toluene, xylene, etc., ethers such as 1,4-dioxane, tetrahydrofuran (hereinafter referred to as "THF"), and amides such as N,N-dimethylformamide (hereinafter referred to as "DMF"), N,N-dimethylacetamide (hereinafter referred to as "DMA"), N-methyl-2-pyrrolidone (hereinafter referred to as "NMP"), etc., or mixed solvents thereof. As the palladium catalyst which may be used, for example, there are exemplified tris(dibenzylideneacetone) (chloroform)dipalladium (hereinafter referred to as "$Pd_2(dba)_3 \cdot CHCl_3$"), tris(dibenzylideneacetone)dipalladium (hereinafter referred to as "$Pd_2(dba)_3$"), and palladium(II) acetate. An amount of such a palladium catalyst is suitably in the range of from 0.001 moles to 0.3 moles per mole of the compound [2]. As the ligand which may be used, for example, there can be exemplified 1,1'-bis(diphenylphosphino)ferrocene (hereinafter referred to as "dppf"), 4,5-bis(diphenylphosphino)-9,9'-dimethylxanthene (hereinafter referred to as "Xantphos"), 2-dicyclohexylphosphino-2',4',6'-triisopropylbiphenyl (hereinafter referred to as "XPhos"), (±)-2,2'-bis(diphenylphosphino)-1,1'-binaphthyl (hereinafter referred to as "(±)-BINAP"), 2-(di-tert-butylphosphino)biphenyl, bis[2-(diphenylphosphino)phenyl]ether (hereinafter referred to as "DPEphos"), tri-tert-butylphosphine, and 2-di-tert-butylphosphino-2',4',6'-triisopropylbiphenyl (hereinafter referred to as "t-Butyl XPhos"). An amount of such a ligand suitably in the range of from 1.0 mole to 5.0 moles per mole of the palladium catalyst. As the base which may be used, for example, there can be exemplified sodium tert-butoxide, tripotassium phosphate, and cesium carbonate. An amount of such a base is suitably in the range of from 1.0 mole to 3.0 moles per mole of the compound [2]. Although reaction time is variable with the kind of the raw materials to be used, reaction temperature, or the like, in general, it is suitably in the range of from 10 minutes to 24 hours.

The compound [2] that is the raw material compound can be, for example, produced according to a method described in any of the following Production Methods A to J.

Production Method A (production method of a compound represented by the following general formula [2Aa](hereinafter referred to as "compound [2Aa]"), which is the compound [2], wherein $R^2$ is H, and X is CH)

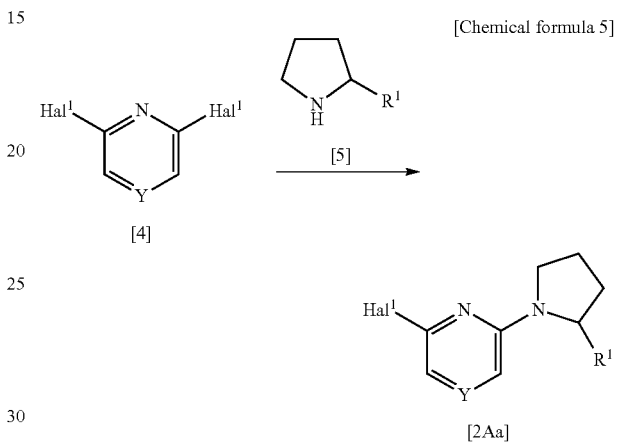

($R^1$, $Hal^1$, and Y are synonymous with those described above.)

The compound [2Aa] can be produced by a reaction of a compound represented by the foregoing general formula [4], which is commercially available or can be produced by a known method (hereinafter referred to as "compound [4]"), and a compound represented by the foregoing general formula [5](hereinafter referred to as "compound [5]") in a suitable solvent in the presence of a base at a temperature from 20° C. to 200° C. by using microwaves as necessary. As the base which may be used, for example, there can be exemplified pyridine, triethylamine, N,N-diisopropylethylamine (hereinafter referred to as "DIPEA"), sodium carbonate, and sodium bicarbonate. Although the solvent which may be used is not particularly limited so long as it does not participate in the reaction, there can be exemplified alcohols such as 1-butanol, 2-methoxyethanol, etc., ethers such as THF, 1,4-dioxane, etc., amides such as DMF, DMA, etc., hydrocarbons such as benzene, toluene, etc., and acetonitrile, or mixed solvents thereof. Although reaction time is variable with the kind of the raw materials to be used or reaction temperature, in general, it is suitably in the range of from 1 to 24 hours.

It is to be noted that in the compound [4], as the compound wherein Y is N or CH, those which are commercially available can be used.

In addition, in the compound [4], a compound represented by the following general formula [4A] (hereinafter referred to as "compound [4A]"), wherein Y is $CR^{4a}$ ($R^{4a}$ represents 1) alkoxy or alkyl optionally substituted by halogen, 2) cycloalkyl, 3) carbamoyl or phenyl optionally substituted by alkylsulfonyl, or 4) alkyl optionally substituted by hydroxyl or alkoxy, halogen, or heteroaryl optionally substituted by hydroxyl or alkoxy), can be, for example, produced by the following method.

[Chemical formula 6] [Chemical formula 7]

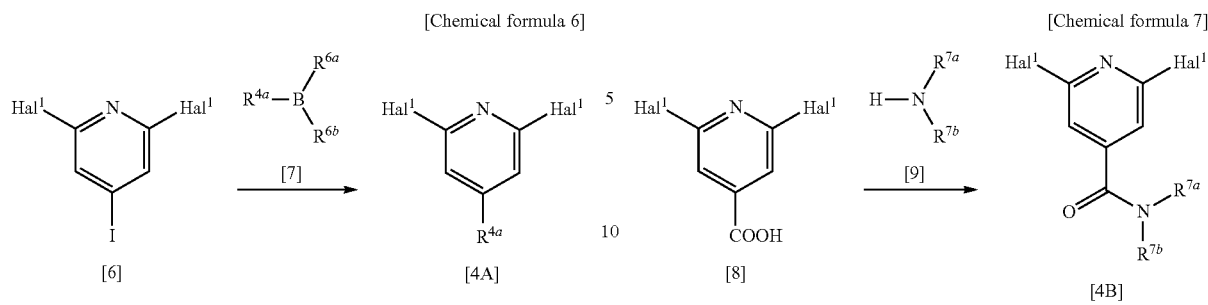

($Hal^1$ and $R^{4a}$ are synonymous with those described above; and each of $R^{6a}$ and $R^{6b}$ represents hydroxyl, or $R^{6a}$ and $R^{6b}$ are taken jointly to represent —O—C($CH_3$)$_2$—C($CH_3$)$_2$—O—, —O—($CH_2$)$_3$—O—, or —O—$CH_2$—C($CH_3$)$_2$—$CH_2$—O—.)

The compound [4A] can be produced by a cross-coupling reaction of a compound represented by the foregoing general formula [6], which is commercially available (hereinafter referred to as "compound [6]"), and a compound represented by the foregoing general formula [7] which is commercially available or can be produced by a known method (hereinafter referred to as "compound [7]"). The present reaction can be, for example, performed in the presence of a palladium catalyst in a suitable solvent at a temperature in the range of from 20 to 200° C. by adding a base or an inorganic salt as necessary. As the palladium catalyst which may be used, for example, there can be exemplified tetrakis(triphenylphosphine)palladium (hereinafter referred to as "Pd(PPh$_3$)$_4$"), dichlorobis(triphenylphosphine)palladium (hereinafter referred to as "PdCl$_2$(PPh$_3$)$_2$"), and a 1,1'-bis(diphenylphosphino)ferrocene-palladium(II) dichloride-dichloromethane complex (hereinafter referred to as "[PdCl$_2$(dppf)$_2$]CH$_2$Cl$_2$"). An amount of the palladium catalyst which is used is suitably in the range of from 0.001 to 0.3 moles per mole of the compound [6]. Although the reaction solvent which may be used is not particularly limited so long as it does not participate in the reaction, for example, there can be exemplified ethers such as THF, 1,4-dioxane, 1,2-dimethoxyethane, etc., alcohols such as methanol, ethanol, etc., amides such as DMF, DMA, etc., hydrocarbons such as benzene, toluene, etc., and water, or mixed solvents thereof. As the base which may be used, for example, there can be exemplified sodium hydroxide, potassium carbonate, sodium carbonate, and the like. As the inorganic salt which may be used, for example, there can be exemplified lithium chloride, cesium fluoride, and the like. Although reaction time is variable with the kind of the raw materials to be used or reaction temperature, in general, it is suitably in the range of from 30 minutes to 24 hours.

In addition, in the compound [4], a compound represented by the following general formula [4B] (hereinafter referred to as "compound [4B]"), wherein Y is CCONR$^{7a}$R$^{7b}$ (R$^{7a}$ and R$^{7b}$ may be the same as or different from each other, and each represents H, alkyl optionally substituted by hydroxyl or alkoxy, alkylsulfonyl, saturated heterocyclic group optionally substituted by alkyl, or cycloalkyl optionally substituted by hydroxyl or carboxyl), can be produced by the following method.

($Hal^1$, $R^{7a}$, and $R^{7b}$ are synonymous with those described above.)

The compound [4B] can be produced by a condensation reaction of a compound represented by the foregoing general formula [8], which is commercially available (hereinafter referred to as "compound [8]"), and a compound represented by the foregoing general formula [9] which is commercially available or can be produced by a known method (hereinafter referred to as "compound [9]"). In the present reaction, a derivative of the compound [8] can also be used in place of the compound [8] as necessary. As the derivative of the compound [8], for example, there can be exemplified those which are generally used for an amide bond formation reaction, such as acid halides (for example, acid chlorides or acid bromides), mixed acid anhydrides, imidazolides, active amides, etc. In the case of using the compound [8], the reaction can be performed at a temperature from −20° C. to 100° C. in the presence or absence of a base by using a condensing agent. As the condensing agent which may be used for the present reaction, for example, there can be exemplified 1,1'-oxalyldiimidazole, 1-ethyl-3-(3-dimethylaminopropyl)carbodiimide, dicyclohexylcarbodiimide, diethyl cyanophosphonate, O-(benzotriazol-1-yl)-N,N,N',N'-tetramethyluronium hexafluorophosphate (hereinafter referred to as "HBTU"), and 1H-benzotriazol-1-yl-oxytripyrrolidinophosphonium hexafluorophosphate (hereinafter referred to as "PyBOP (registered trademark)"). As the base which may be used for the present reaction, for example, there can be exemplified organic bases such as triethylamine, DIPEA, N,N-dimethylaniline, pyridine, and 1,8-diazabicyclo[5.4.0]-7-undecene. Although a solvent which may be used is not particularly limited so long as it does not participate in the reaction, for example, there can be exemplified ethers such as THF, 1,4-dioxane, diethyl ether, etc., amides such as DMF, DMA, etc., nitriles such as acetonitrile, propionitrile, etc., hydrocarbons such as benzene, toluene, etc., and halogenated hydrocarbons such as chloroform, dichloromethane, etc., or mixed solvents thereof. In addition, an additive can be used as necessary. As the additive which may be used, for example, there can be exemplified 1-hydroxybenzotriazole (hereinafter referred to as "HOBt") and 1-hydroxy-7-azabenzotriazole (hereinafter referred to as "HOAt"). Although reaction time is variable with the kind of the raw materials to be used, reaction temperature, or the like, in general, it is suitably in the range of from 10 minutes to 24 hours. An amount of each of the compound [9] and the condensing agent to be used is, for example, suitably in the range of from 1 molar time to 3 molar times per mole of the compound [8].

In addition, in the compound [4], a compound represented by the following general formula [4C] (hereinafter referred to as "compound [4C]"), wherein $Y^1$ is CCO$_2$R$^8$ (R$^8$ represents alkyl), can be produced by the following method.

[Chemical formula 8]

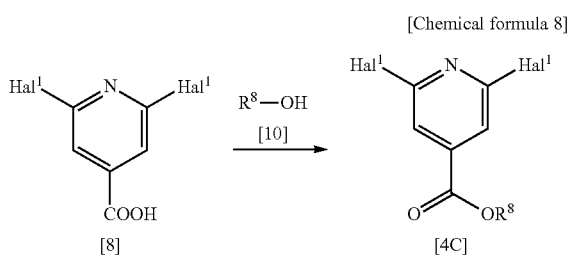

($Hal^1$ and $R^8$ are synonymous with those described above.)

The compound [4C] can be produced by a condensation reaction of the compound [8] which is commercially available and a compound represented by the foregoing general formula [10] (hereinafter referred to as "compound [10]"). The present reaction can be, for example, performed according to a method of a known esterification reaction. As the compound [10] which may be used, there can be exemplified alcohols such as methanol, ethanol, etc.

Production Method A (another method) (production method of a compound represented by the following general formula [2Aa](hereinafter referred to as "compound [2Aa]"), which is the compound [2], wherein $R^2$ is H, and X is CH)

[Chemical formula 9]

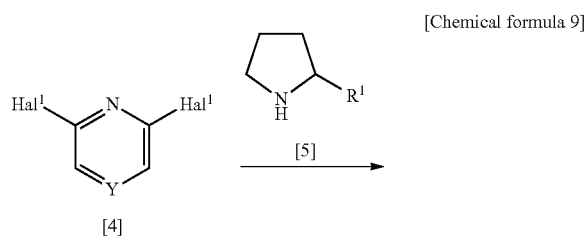

($Hal^1$, $R^1$, and Y are synonymous with those described above.)

The compound [2Aa] can be produced by a condensation reaction of the compound [4] and the compound [5] by using a palladium catalyst according to the method described in the foregoing Production Method 1.

Production Method B (production method of a compound represented by the following general formula [2Ab](hereinafter referred to as "compound [2Ab]"), which is the compound 2, wherein X is CH, and $R^1$ is halogen)

[Chemical formula 10]

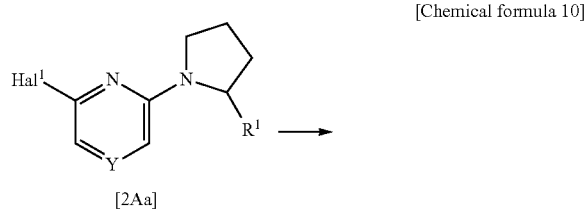

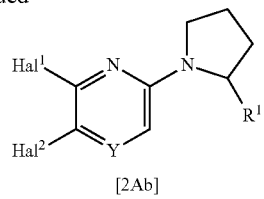

($Hal^1$, $R^1$, and Y are synonymous with those described above; and Hal represents halogen.)

The compound [2Ab] can be produced by halogenation of the compound [2Aa]. As a halogenating agent which may be used, there can be exemplified N-bromosuccinimide (hereinafter referred to as "NBS"), N-iodosuccinimide (hereinafter referred to as "NIS"), bromine, iodine, and the like. In general, the halogenation can be performed at a temperature in the range of from 0 to 200° C. Although a solvent which may be used is not particularly limited so long as it does not participate in the reaction, for example, there can be exemplified hydrocarbons such as toluene, xylene, etc., ethers such as 1,4-dioxane, THF, etc., amides such as DMF, DMA, etc., halogenated hydrocarbons such as chloroform, dichloromethane, etc., and acetonitrile, or mixed solvents thereof. In addition, a suitable base may be added as necessary, and as the base which may be used, for example, there can be exemplified pyridine, DIPEA, and the like.

Production Method C (production method of a compound represented by the following general formula [2Ac](hereinafter referred to as "compound [2Ac]"), which is the compound 2, wherein X is CH, and $R^2$ is alkyl optionally substituted by halogen, cycloalkyl, or heteroaryl optionally substituted by alkyl)

[Chemical formula 11]

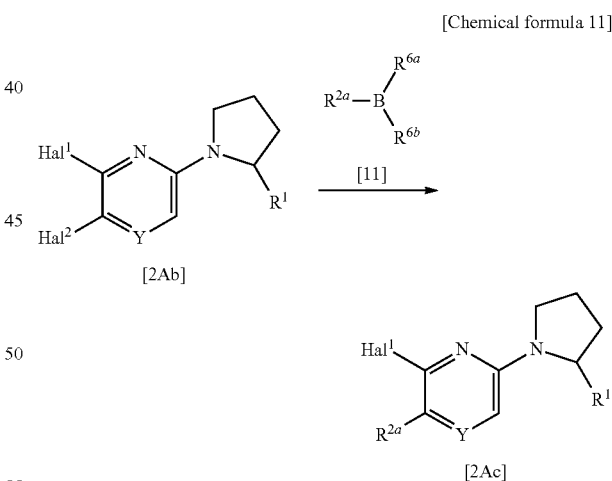

($Hal^1$, $Hal^2$, $R^1$, $R^{6a}$, $R^{6b}$, and Y are synonymous with those described above; and $R^{2a}$ represents alkyl optionally substituted by halogen, cycloalkyl, or heteroaryl optionally substituted by alkyl.)

The compound [2Ac] can be produced by a cross-coupling reaction of the compound [2Ab] and a compound represented by the foregoing general formula [11] (hereinafter referred to as "compound [11]"). The present reaction can be, for example, performed in the presence of a palladium catalyst in a suitable solvent at a temperature in the range of from 20 to 200° C. by adding a base or an inorganic salt as necessary. As the palladium catalyst which may be used, for example, there can be exemplified Pd(PPh$_3$)$_4$, PdCl$_2$(PPh$_3$)$_2$, and [PdCl$_2$(dppf)$_2$]CH$_2$Cl$_2$. An amount of the palladium catalyst which is used is suitably in the range of from 0.001 to 0.3 moles per mole of the compound [2Ab]. Although the reaction solvent which may be used is not particularly limited so long as it does not participate in the reaction, for example, there can be exemplified ethers such as THF, 1,4-dioxane, 1,2-dimethoxyethane, etc., alcohols such as methanol, ethanol, etc., amides such as DMF, DMA, etc., hydrocarbons such as benzene, toluene, etc., and water, or mixed solvents thereof. As the base which may be used, for example, there can be exemplified sodium hydroxide, potassium carbonate, sodium carbonate, and the like. As the inorganic salt which may be used, for example, there can be exemplified lithium chloride, cesium fluoride, and the like. Although reaction time is variable with the kind of the raw materials to be used or reaction temperature, in general, it is suitably in the range of from 30 minutes to 24 hours.

Production Method D (production method of a compound represented by the following general formula [2Ad](hereinafter referred to as "compound [2Ad]"), which is the compound 2, wherein X is CH, and R$^2$ is alkoxy)

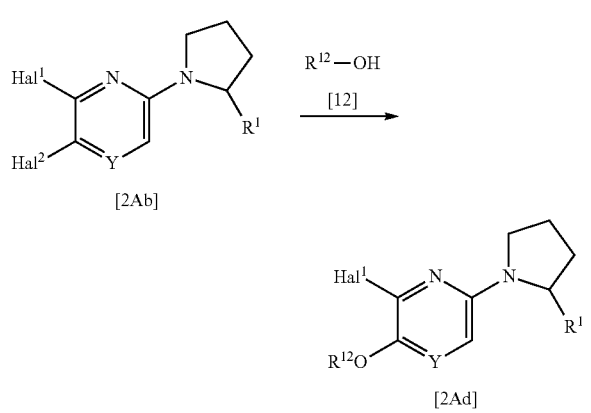

[Chemical formula 12]

(Hal$^1$, Hal$^2$, R$^1$, and Y are synonymous with those described above; and R$^{12}$ represents alkyl.)

The compound [2Ad] can be produced by a cross-coupling reaction of the compound [2Ab] and a compound represented by the foregoing general formula [12] (hereinafter referred to as "compound [12]"). The present reaction can be, for example, performed in the presence of a palladium catalyst and a ligand in a suitable solvent at a temperature in the range of from 20 to 200° C. by adding a base as necessary. As the palladium catalyst which may be used, for example, there can be exemplified Pd$_2$(dba)$_3$.CHCl$_3$, Pd$_2$(dba)$_3$, and palladium(II) acetate. An amount of such a palladium catalyst is suitably in the range of from 0.001 to 0.3 moles per mole of the compound [2Ab]. As the ligand which may be used, for example, there can be exemplified dppf, Xantphos, XPhos, (±)-BINAP, 2-(di-tert-butylphosphino)biphenyl, DPEphos, and tri-tert-butylphosphine. An amount of such a ligand is suitably in the range of from 1.0 mole to 5.0 moles per mole of the palladium catalyst. Although the solvent which may be used is not particularly limited so long as it does not participate in the reaction, for example, there can be exemplified hydrocarbons such as toluene, xylene, etc., ethers such as 1,4-dioxane, THF, etc., and amides such as DMF, DMA, NMP, etc., or mixed solvents thereof. As the base which may be used, for example, there can be exemplified sodium tert-butoxide, tripotassium phosphate, and the like. Although reaction time is variable with the kind of the raw materials to be used or reaction temperature, in general, it is suitably in the range of from 30 minutes to 24 hours.

Production Method E (production method of a compound represented by the following general formula [2Af](hereinafter referred to as "compound [2Af]"), which is the compound 2, wherein X is CR$^{3a}$ (R$^{3a}$ represents alkyl))

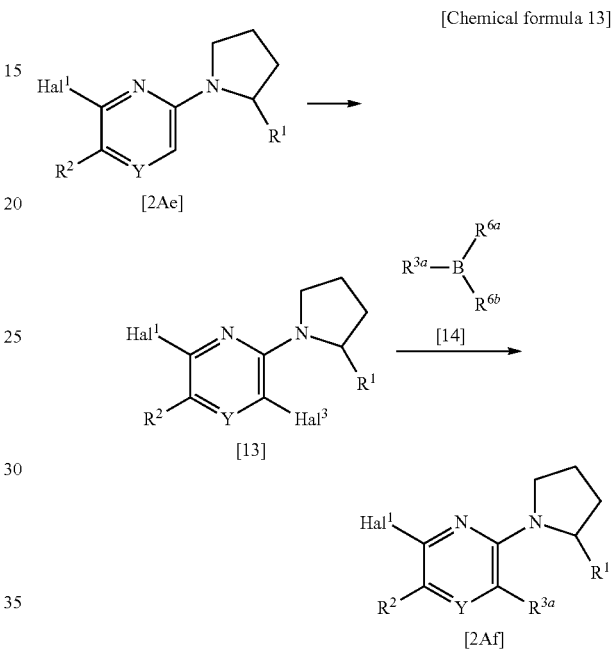

[Chemical formula 13]

(Hal$^1$, R$^1$, R$^2$, R$^{3a}$, R$^{6b}$, R$^{6b}$, and Y are synonymous with those described above; and Hal$^3$ represents halogen.)

Step 1

The compound [13] can be produced by halogenation of a compound represented by the foregoing general formula [2Ae](hereinafter referred to as "compound [2Ae]"). As a halogenating agent which may be used, there can be exemplified NBS, NIS, bromine, iodine, and the like. In general, the halogenation can be performed at a temperature in the range of from 0 to 200° C. Although a solvent which may be used is not particularly limited so long as it does not participate in the reaction, for example, there can be exemplified hydrocarbons such as toluene, xylene, etc., ethers such as 1,4-dioxane, THF, etc., amides such as DMF, DMA, etc., halogenated hydrocarbons such as chloroform, dichloromethane, etc., and acetonitrile, or mixed solvents thereof. In addition, a suitable base may be added as necessary, and as the base which may be used, for example, there can be exemplified pyridine, DIPEA, and the like.

Step 2

The compound [2Af] can be produced by a cross-coupling reaction of the compound [13] and a compound represented by the foregoing general formula [14] (hereinafter referred to as "compound [14]") by using a palladium catalyst according to the method described in the foregoing Production Method C.

Production Method F (production method of a compound represented by the following general formula [2Ba](hereinafter referred to as "compound [2Ba]"), which is the compound [2], wherein: R² is hydrogen, alkyl optionally substituted by halogen, cycloalkyl, alkoxy, or heteroaryl optionally substituted by alkyl; X is N; and Y is $CR^{4a}$ ($R^{4a}$ is synonymous with that described above))

[Chemical formula 14]

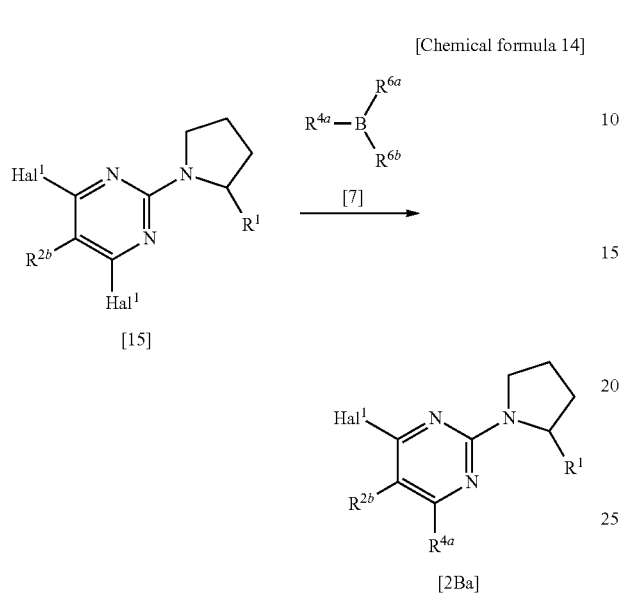

[15]

[2Ba]

($Hal^1$, $R^1$, $R^{4a}$, $R^{6a}$, and $R^{6b}$ are synonymous with those described above; and $R^{2b}$ is hydrogen, alkyl optionally substituted by halogen, cycloalkyl, alkoxy, or heteroaryl optionally substituted by alkyl.)

The compound [2Ba] can be produced by a cross-coupling reaction of a compound represented by the foregoing general formula [15] (hereinafter referred to as "compound [15]") and the compound [7] by using a palladium catalyst according to the method described in the foregoing Production Method C.

It is to be noted that the compound [15] that is the raw material can be, for example, produced by the following method.

[Chemical formula 15]

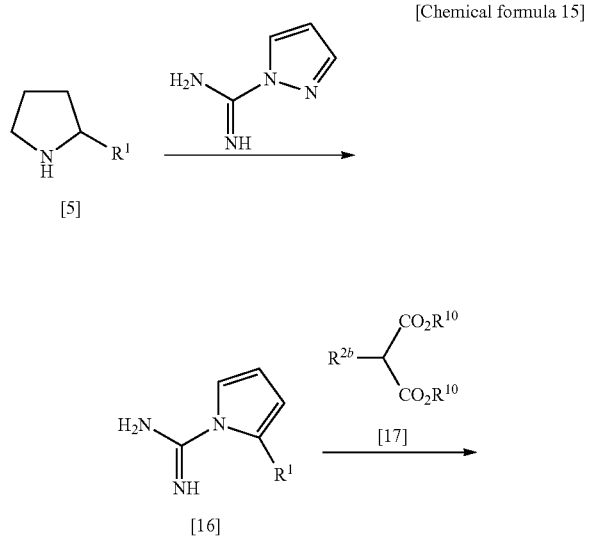

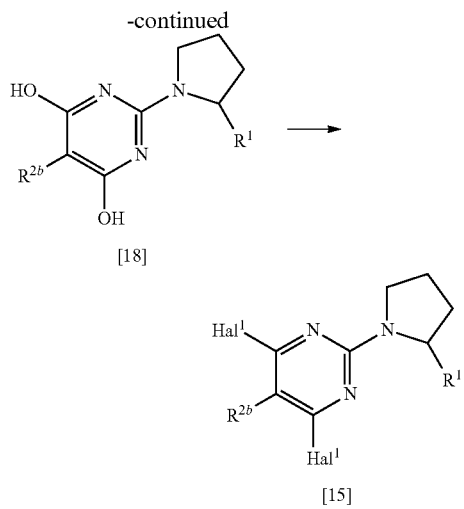

[18]

[15]

($Hal^1$, $R^1$, and $R^{2b}$ are synonymous with those described above; and $R^{10}$ is alkyl.)

Step 1

A compound represented by the foregoing general formula [16] (hereinafter referred to as "compound [16]") can be produced by a reaction of the compound [5], which is commercially available or can be produced by a known method, and 1H-pyrazole-1-carboximidamide. The present reaction is generally performed at a temperature from 20° C. to 200° C. in the presence of a base in a suitable solvent. As the base which may be used, for example, there can be exemplified pyridine, triethylamine, DIPEA, potassium carbonate, sodium bicarbonate, and the like. Although the solvent which may be used is not particularly limited so long as it does not participate in the reaction, for example, there can be exemplified alcohols such as methanol, ethanol, etc., ethers such as 1,4-dioxane, THF, etc., amides such as DMF, DMA, etc., acetonitrile, and water, or mixed solvents thereof. Although reaction time is variable with the kind of the raw materials to be used or reaction temperature, in general, it is suitably in the range of from 30 minutes to 24 hours.

Step 2

A compound represented by the foregoing general formula [18] (hereinafter referred to as "compound [18]") can be produced by a reaction of the compound [16] and a compound represented by the foregoing general formula [17] which is commercially available or can be produced by a known method (hereinafter referred to as "compound [17]"). The present reaction is generally performed at a temperature from 20° C. to 200° C. in the presence of a base in a suitable solvent. As the base which may be used, for example, there can be exemplified sodium methoxide, sodium ethoxide, sodium tert-butoxide, and the like. Although the solvent which may be used is not particularly limited so long as it does not participate in the reaction, for example, there can be exemplified alcohols such as methanol, ethanol, etc., ethers such as 1,4-dioxane, THF, etc., and amides such as DMF, DMA, NMP, etc., or mixed solvents thereof. Although reaction time is variable with the kind of the raw materials to be used or reaction temperature, in general, it is suitably in the range of from 30 minutes to 24 hours.

Step 3

The compound [15] can be produced by halogenation of the compound [18]. The present reaction is generally performed at a temperature from room temperature to 150° C. by using phosphorus oxychloride, phosphorus oxybromide, phosphorus pentachloride, phosphorus pentabromide, or the like and in the presence of a suitable solvent as necessary. Although the solvent which may be used is not particularly limited so long as it does not participate in the reaction, for example, there can be exemplified hydrocarbons such as toluene, xylene, etc., ethers such as 1,4-dioxane, THF, etc., amides such as DMF, DMA, etc., and halogenated hydrocarbons such as chloroform, dichloromethane, etc., or mixed solvents thereof. In addition, a suitable base may be added as necessary, and as the base which may be used, for example, there can be exemplified N,N-diethylaniline, DIPEA, and the like.

Production Method G (production method of a compound represented by the following general formula [2Bb](hereinafter referred to as "compound [2Bb]"), which is the compound [2], wherein: $R^2$ is hydrogen, alkyl optionally substituted by halogen, cycloalkyl, alkoxy, or heteroaryl optionally substituted by alkyl; X is N; and Y is $CCO_2R^{11}$ ($R^{11}$ represents alkyl))

[Chemical formula 16]

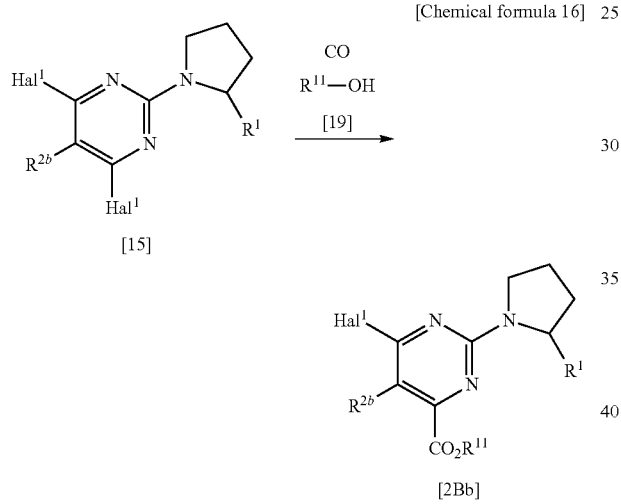

(Hal$^1$, R$^1$, R$^{2b}$, and R$^{11}$ are synonymous with those described above.)

The compound [2Bb] can be produced by a reaction of the compound [15], carbon monoxide, and a compound represented by the foregoing general formula [19] (hereinafter referred to as "compound [19]"). The present reaction can be performed by adapting a method which is known as a carbon monoxide insertion reaction using a palladium catalyst. In the present reaction, a base can also be added as necessary. As the palladium catalyst which may be used, for example, there can be exemplified Pd(PPh$_3$)$_4$, PdCl$_2$(PPh$_3$)$_2$, and [PdCl$_2$(dppf)$_2$]CH$_2$Cl$_2$. An amount of the palladium catalyst which is used is suitably in the range of from 0.001 to 0.3 moles per mole of the compound [15]. As the compound [19] which may be used, there can be exemplified alcohols such as methanol, ethanol, etc. As the base which may be used, for example, there can be exemplified triethylamine and DIPEA. The reaction is performed at a temperature of from 20 to 200° C., and though reaction time is variable with the kind of the raw materials to be used or reaction temperature, in general, it is suitably in the range of from 30 minutes to 24 hours.

Production Method H (production method of a compound represented by the following general formula [2Bc](hereinafter referred to as "compound [2Bc]"), which is the compound [2], wherein: $R^2$ is hydrogen, alkyl optionally substituted by halogen, cycloalkyl, alkoxy, or heteroaryl optionally substituted by alkyl; X is N; and Y is $CCO_2H$)

[Chemical formula 17]

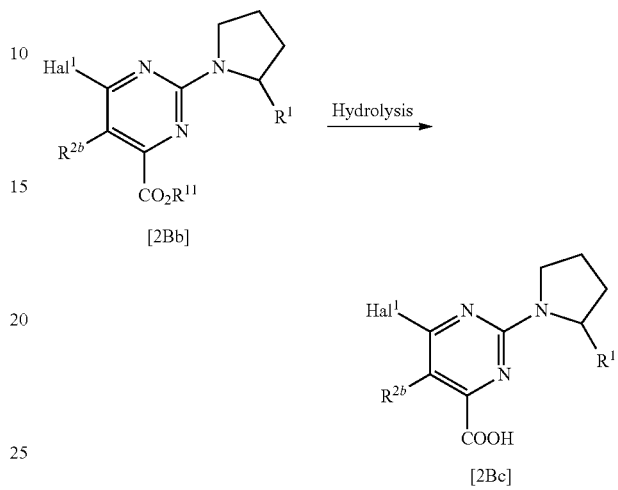

(Hal$^1$, R$^1$, R$^{2b}$, and R$^{11}$ are synonymous with those described above.)

The compound [2Bc] can be produced by hydrolysis of the compound [2Bb]. The present reaction is generally performed in the presence of an acid or a base in a suitable solvent. As the acid which is used for the hydrolysis reaction, there can be exemplified inorganic acids such as hydrochloric acid and sulfuric acid, and organic acids such as methanesulfonic acid and trifluoroacetic acid; and as the base, there can be exemplified inorganic bases such as sodium hydroxide, potassium hydroxide, lithium hydroxide, etc. As the reaction solvent, for example, there can be exemplified alcohols such as methanol, ethanol, etc., ethers such as THF, 1,4-dioxane, etc., and water, or mixed solvents thereof. The reaction is performed at a temperature of from 0 to 100° C., and reaction time is generally from 30 minutes to 24 hours.

Production Method I (production method of a compound represented by the following general formula [2Bd](hereinafter referred to as "compound [2Bd]"), which is the compound [2], wherein: $R^2$ is hydrogen, alkyl optionally substituted by halogen, cycloalkyl, alkoxy, or heteroaryl optionally substituted by alkyl; X is N; and Y is $CCONR^{7a}R^{7b}$ ($R^{7a}$ and $R^{7b}$ are synonymous with those described above))

[Chemical formula 18]

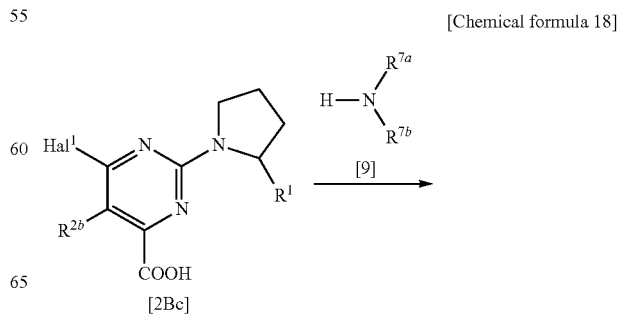

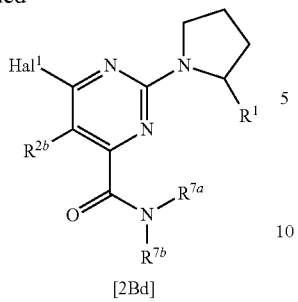

[2Bd]

(Hal$^1$, R$^1$, R$^{2b}$, R$^{7a}$, and R$^{7b}$ are synonymous with those described above.)

The compound [2Bd] can be produced by a condensation reaction of the compound [2Bc] and the compound [9]. In addition, in the present reaction, a derivative of the compound [2Bc] can also be used in place of the compound [2Bc] as necessary. As the derivative of the compound [2Bc], for example, there can be exemplified those which are generally used for an amide condensation formation reaction, such as acid halides (for example, acid chlorides or acid bromides), mixed acid anhydrides, imidazolides, active amides, etc. In the case of using the compound [2Bc], the reaction can be performed at a temperature from −20° C. to 100° C. in the presence or absence of a base by using a condensing agent. As the condensing agent which may be used for the present reaction, for example, there can be exemplified 1,1'-oxalyldiimidazole, 1-ethyl-3-(3-dimethylaminopropyl)carbodiimide, dicyclohexylcarbodiimide, diethyl cyanophosphonate, HBTU, and PyBOP (registered trademark). As the base which may be used for the present reaction, for example, there can be exemplified organic bases such as triethylamine, DIPEA, N,N-dimethylaniline, pyridine, and 1,8-diazabicyclo[5.4.0]-7-undecene. Although a solvent which may be used is not particularly limited so long as it does not participate in the reaction, for example, there can be exemplified ethers such as THF, 1,4-dioxane, diethyl ether, etc., amides such as DMF, DMA, etc., nitriles such as acetonitrile, propionitrile, etc., hydrocarbons such as benzene, toluene, etc., and halogenated hydrocarbons such as chloroform, dichloromethane, etc., or mixed solvents thereof. In addition, an additive can be used as necessary. As the additive which may be used, for example, there can be exemplified HOBt and HOAt. Although reaction time is variable with the kind of the raw materials to be used, reaction temperature, or the like, in general, it is suitably in the range of from 10 minutes to 24 hours. An amount of each of the compound [9] and the condensing agent to be used is, for example, suitably in the range of from 1 mole to 3 moles per mole of the compound [2Bc].

Production Method J (production method of a compound represented by the following general formula [2Be](hereinafter referred to as "compound [2Be]"), which is the compound [2], wherein in the case where X is N, and Y is CR$^4$, R$^2$ and R$^4$ are taken jointly to form a group represented by the following general formula, together with the carbon atom to which R bonds as well as the carbon atom to which R$^4$ bonds:

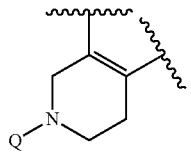

[Chemical formula 19]

(Q is synonymous with that described above))

[Chemical formula 20]

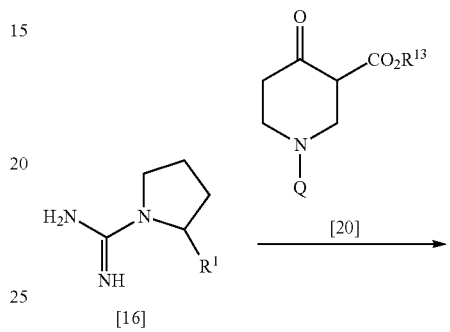

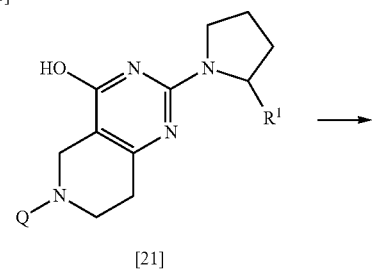

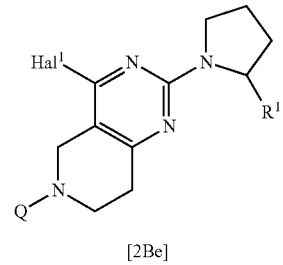

[2Be]

(Hal$^1$, Q, and R$^1$ are synonymous with those described above; and R$^{13}$ represents alkyl.)

Step 1

The compound [21] can be produced by a reaction of a compound [20], which is commercially available or can be produced by a known method, and the compound [16]. The present reaction is generally performed at a temperature from 20° C. to 200° C. in the presence of a base in a suitable solvent. As the base which may be used, for example, there can be exemplified sodium methoxide, sodium ethoxide, sodium tert-butoxide, and the like. Although the solvent which may be used is not particularly limited so long as it does not participate in the reaction, for example, there can be exemplified alcohols such as methanol, ethanol, etc., ethers such as 1,4-dioxane, THF, etc., and amides such as DMF, DMA, NMP, etc., or mixed solvents thereof. Although reaction time is variable with the kind of the raw materials to be used or reaction temperature, in general, it is suitably in the range of from 30 minutes to 24 hours.

Step 2

The compound [2Be] can be produced by halogenation of the compound [21]. The present reaction is generally performed at a temperature from room temperature to 150° C. by using phosphorus oxychloride, phosphorus oxybromide, phosphorus pentachloride, phosphorus pentabromide, or the like and in the presence of a suitable solvent as necessary. Although the solvent which may be used is not particularly limited so long as it does not participate in the reaction, for example, there can be exemplified hydrocarbons such as toluene, xylene, etc., ethers such as 1,4-dioxane, THF, etc., amides such as DMF, DMA, etc., and halogenated hydrocarbons such as chloroform, dichloromethane, etc., or mixed solvents thereof. In addition, a suitable base may be added as necessary, and as the base which may be used, for example, there can be exemplified N,N-diethylaniline, DIPEA, and the like.

Production Method 2 (production method of a compound represented by the following general formula [1A](hereinafter referred to as "compound [1A]"), which is the compound of the present invention, wherein: $R^2$ is hydrogen, alkyl optionally substituted by halogen, cycloalkyl, alkoxy, or heteroaryl optionally substituted by alkyl; X is N; and Y is CH)

[Chemical formula 21]

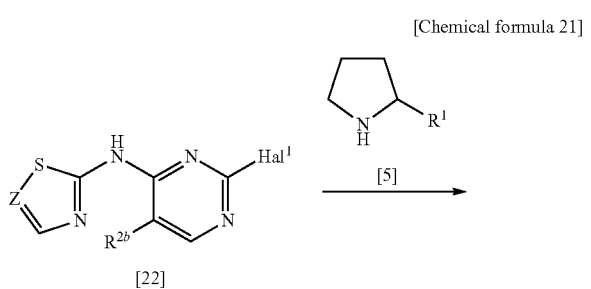

[22]

[1A]

($Hal^1$, $R^1$, $R^{2b}$, and Z are synonymous with those described above.)

The compound [1A] can be produced by a reaction of a compound represented by the foregoing general formula [22](hereinafter referred to as "compound [22]") and the compound [5] in a suitable solvent in the presence of a base at a temperature from 20° C. to 200° C. by using microwaves as necessary. As the base which may be used, for example, there can be exemplified pyridine, triethylamine, DIPEA, potassium carbonate, and sodium bicarbonate. Although the solvent which may be used is not particularly limited so long as it does not participate in the reaction, there can be exemplified alcohols such as 1-butanol, 2-methoxyethanol, etc., ethers such as THF, 1,4-dioxane, etc., amides such as DMF, DMA, etc., hydrocarbons such as benzene, toluene, etc., and acetonitrile, or mixed solvents thereof. Although reaction time is variable with the kind of the raw materials to be used or reaction temperature, in general, it is suitably in the range of from 1 to 24 hours.

It is to be noted that the compound [22] that is the raw material can be, for example, produced by the following method.

[Chemical formula 22]

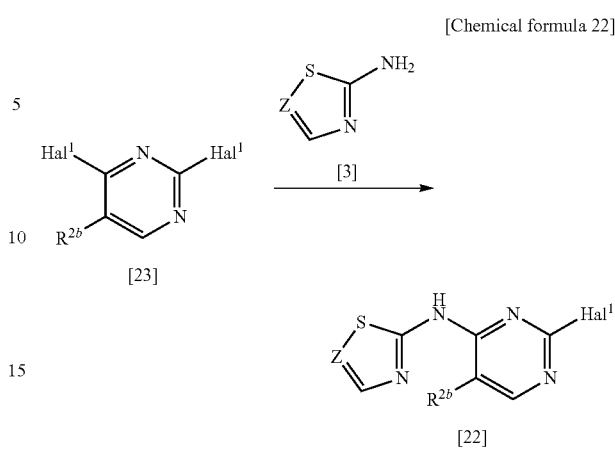

[22]

($Hal^1$, $R^{2b}$, and Z are synonymous with those described above.)

The compound [22] can be produced by a condensation reaction of the compound [3] and a compound represented by the foregoing general formula [23] which is commercially available or can be produced by a known method (hereinafter referred to as "compound [23]") by using a palladium catalyst and a ligand according to the method described in the foregoing Production Method 1.

Production Method 3 (production method of a compound represented by the following general formula [1C](hereinafter referred to as "compound [1C]"), which is the compound of the present invention, wherein: R is halogen; X is N; and Y is $CR^4$ ($R^4$ is synonymous with that described above))

[Chemical formula 23]

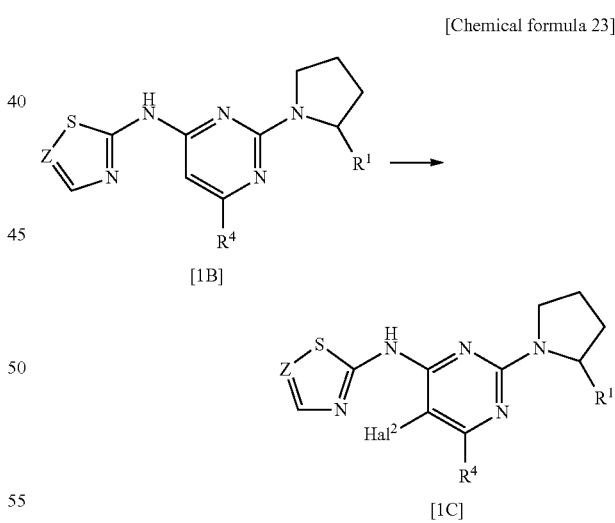

[1B]

[1C]

($Hal^2$, $R^1$, $R^4$, and Z are synonymous with those described above.)

The compound [1C] can be produced by halogenation of a compound represented by the foregoing general formula [1B](hereinafter referred to as "compound [1B]"). As a halogenating agent which may be used, there can be exemplified NBS, NIS, bromine, iodine, and the like. In general, the halogenation can be performed at a temperature in the range of from 0 to 200° C. Although a solvent which may be used is not particularly limited so long as it does not participate in the reaction, for example, there can be exemplified hydrocarbons such as toluene, xylene, etc., ethers such as 1,4-dioxane, THF, etc., amides such as DMF, DMA, etc., halogenated hydrocarbons such as chloroform, dichloromethane, etc., and acetonitrile, or mixed solvents thereof.

Although the compound of the present invention can be used as a medicine as it is, a pharmaceutically acceptable salt thereof can also be formed by a known method using an acid or a base and used as a medicine. As an acid addition salt, for example, there can be exemplified: salts with a mineral acid such as hydrochloric acid, hydrobromic acid, sulfuric acid, phosphoric acid, etc.; and salts with an organic acid such as acetic acid, citric acid, tartaric acid, maleic acid, succinic acid, fumaric acid, p-toluenesulfonic acid, benzenesulfonic acid, methanesulfonic acid, etc. As a base addition salt, for example, there can be exemplified: alkali metal salts such as sodium salts, lithium salts, potassium salts, etc.; alkaline earth metal salts such as aluminum salts, calcium salts, magnesium salts, etc.; and ammonium salts.

For example, a hydrochloride of the compound of the present invention can be obtained by dissolving the compound of the present invention in a solution of hydrogen chloride in an alcohol, ethyl acetate, or diethyl ether.

Although the compound of the present invention may have asymmetrical carbon, all of respective optical isomers and mixtures thereof fall within the scope of the present invention. The optical isomer can be, for example, produced by means of optical resolution from the above-obtained racemate by utilizing basicity thereof according to a known method using an optically active acid (e.g., tartaric acid, dibenzoyltartaric acid, mandelic acid, 10-camphor sulfonic acid, etc.), or by the use of a previously prepared optically active compound as a raw material. Besides, such an optical isomer can also be produced by means of optical resolution using a chiral column or asymmetric synthesis.

In addition, among the compounds of the present invention, all compounds which may form a tautomer fall within the scope of the present invention. As one example, there is exemplified Example 16 or the like.

As shown in the Test Examples as described later, the compound of the present invention or its pharmaceutically acceptable salt has high ROS tyrosine kinase inhibitory activity and can be used as a preventing agent or a treating agent for diseases in which an ROS tyrosine kinase participates, for example, interstitial pneumonia, glioma, meningioma, infiltrating ductal carcinoma, non-small cell lung cancer, glioblastoma, chronic myelomonocytic leukemia, angiosarcoma, inflammatory myofibroblastic tumor, cholangiocarcinoma, gastric cancer, liver cancer, kidney cancer, pancreatic cancer, epithelioid hemangioendothelioma, colorectal cancer, liposarcoma, breast cancer, Spitzoid neoplasms, or testicular cancer.

The compound of the present invention or its pharmaceutically acceptable salt can be, for example, used as a preventing agent or a treating agent for diseases in which the ROS tyrosine kinase overexpresses. As the diseases in which the ROS tyrosine kinase overexpresses, for example, there can be exemplified glioma, meningioma, infiltrating ductal carcinoma, chronic myelomonocytic leukemia, or interstitial pneumonia.

The compound of the present invention or its pharmaceutically acceptable salt can be, for example, used as a preventing agent or a treating agent for malignant tumors which are positive against ROS fusion genes (for example, FIG-ROS fusion gene, SLC34A2-ROS fusion gene, CD74-ROS, TPM3-ROS fusion gene, SDC4-ROS fusion gene, EZR-ROS fusion gene, LRIG3-ROS fusion gene, CCDC6-ROS fusion gene, KDELR2-ROS fusion gene, CEP85L-ROS fusion gene, YWHAE-ROS fusion gene, or TFG-ROS1 fusion gene). As the ROS fusion gene-positive malignant tumor, for example, there can be exemplified glioblastoma (for example, FIG-ROS fusion gene), non-small cell lung cancer (for example, SLC34A2-ROS fusion gene, CDR74-ROS, FIG-ROS fusion gene, TPM3-ROS fusion gene, SDC4-ROS fusion gene, EZR-ROS fusion gene, LRIG3-ROS fusion gene, CCDC6-ROS fusion gene, or KDELR2-ROS fusion gene), cholangiocarcinoma (for example, FIG-ROS fusion gene), ovarian cancer (for example, FIG-ROS fusion gene), gastric cancer (for example, SLC34A2-ROS fusion gene), angiosarcoma (for example, CEP85L-ROS fusion gene), inflammatory myofibroblastic tumor (for example, YWHAE-ROS fusion gene or TFG-ROS1 fusion gene), epithelioid hemangioendothelioma, colorectal cancer, liposarcoma, and Spitzoid neoplasms.

The compound of the present invention or its pharmaceutically acceptable salt can be, for example, used as a preventing agent for malignant tumors which may possibly appear by activation of an ROS tyrosine kinase.

The compound of the present invention or its pharmaceutically acceptable salt can be, for example, used as a preventing agent or a treating agent for malignant tumors in which abnormality in an ROS tyrosine kinase is seen. As the malignant tumor in which abnormality in an ROS tyrosine kinase is seen, for example, there can be exemplified liver cancer, kidney cancer, pancreatic cancer, testicular cancer, and breast cancer.

In the case of administering the compound of the present invention or its pharmaceutically acceptable salt as a medicine, the compound of the present invention or its pharmaceutically acceptable salt can be administered on mammalians including humans as it is or as a pharmaceutical composition prepared by containing it in an amount of, for example, from 0.001% to 99.5%, and preferably from 0.1% to 90% in a pharmaceutically acceptable, nontoxic and inactive carrier.

As the carrier, one or more kinds of a solid, semi-solid or liquid diluent, a filler, and other auxiliary agents for a formulation are used. It is desirable to administer the pharmaceutical composition according to the present invention in a unit dosage form. The pharmaceutical composition can be administered by intra-tissue administration, oral administration, intravenous administration, local administration (e.g., transdermal administration, instillation administration, intraperitoneal administration, intrathoracic administration, etc.), or transrectal administration. As a matter of course, the pharmaceutical composition is administered in a dosage form suitable for any of these administration methods.

Although it is desirable that the dose as a medicine is adjusted taking into consideration conditions of a patient, such as age, body weight, and kind and degree of a disease, as well as an administration route, in general, it is suitable that a daily dose as an active ingredient of the compound of the present invention or its pharmaceutically acceptable salt in an adult is in the range of from 0.01 mg to 5 g per adult, and preferably in the range of from 1 mg to 500 mg per adult in the case of oral administration. In some cases, a lower dose may be sufficient, or conversely, a higher dose may be required. In general, the dose is given once daily or several times daily as divided portions, or in the case of intravenous administration, the medicine can be quickly administered or continuously administered within 24 hours.

EXAMPLE

The present invention is described in more detail by way of Reference examples, Examples, Test Examples and Formulation Examples of the compound of the present invention, to which, however, the present invention is not limited.

Reference Example 1

2-(4-Methylphenyl)pyrrolidine-1-carboximidamide hydrochloride

To 15 mL of acetonitrile, 2.7 g of 2-(4-methylphenyl)pyrrolidine, 2.4 g of 1H-pyrazole-1-carboxamidine hydrochloride and 2.2 mL of DIPEA were added, and then the reaction solution was stirred at 85° C. for 12 hours. After cooling the reaction solution, a precipitation was generated from the reaction solution and then was filtered to obtain 3.2 g of the objective compound as a white powder.

Reference Example 2

5-Methoxy-2-[2-(4-methylphenyl)pyrrolidin-1-yl]pyrimidine-4,6-diol

Under an argon atmosphere, 368 mg of metallic sodium was added to 18 mL of ethanol, and then the mixture was stirred at room temperature until metallic sodium was dissolved. Subsequently, 1.6 g of 2-(4-methylphenyl)pyrrolidine-1-carboximidamide hydrochloride and 0.97 mL of dimethyl methoxymalonate were added to the reaction mixture, and the mixture was stirred at 90° C. for 4 hours. After cooling the reaction mixture, the mixture was concentrated under reduced pressure, and then 18 mL of water was added to the obtained residue, and 10% HCl aqueous solution was added to the mixture to make the mixture acidic and then the mixture was stirred for 30 minutes. A precipitated solid was generated from the reaction solution and then was filtered to obtain 1.71 g of the objective compound as a white powder.

Reference Example 3

4,6-Dichloro-5-methoxy-2-[2-(4-methylphenyl)pyrrolidin-1-yl]pyrimidine 3 mL of phosphorus oxychloride was added to 1.71 g of 5-methoxy-2-[2-(4-methylphenyl)pyrrolidin-1-yl]pyrimidine-4,6-diol, and then the mixture was stirred at 100° C. for 4 hours. After cooling the reaction mixture, the mixture was poured into ice water. The reaction solution was subjected to an extraction with ethyl acetate. The organic layer was washed with saturated sodium bicarbonate aqueous solution and then dried over magnesium sulfate. The solvent was distilled off under reduced pressure, and then the obtained residue was purified by silica gel column chromatography to obtain 1.7 g of the objective compound as a pale yellow solid.

Reference Example 4

5-Methyl-2-[2-(4-methylphenyl)pyrrolidin-1-yl]pyrimidine-4,6-diol

The objective compound was obtained as a white powder by the same process as in Reference example 2 using dimethyl methylmalonate instead of dimethyl methoxymalonate.

Reference Example 5

4,6-Dichloro-5-methyl-2-[2-(4-methylphenyl)pyrrolidin-1-yl]pyrimidine

The objective compound was obtained as a white powder by the same process as in Reference example 3 using 5-methyl-2-[2-(4-methylphenyl)pyrrolidin-1-yl]pyrimidine-4,6-diol instead of 5-methoxy-2-[2-(4-methylphenyl)pyrrolidin-1-yl]pyrimidine-4,6-diol.

Reference Example 6

(2S)-2-(4-Methylphenyl)pyrrolidine-1-carboximidamide hydrochloride

The objective compound was obtained as a white powder by the same process as in Reference example 1 using (S)-2-(4-methylphenyl)pyrrolidine instead of 2-(4-methylphenyl)pyrrolidine.

Reference Example 7

5-Methoxy-2-[(2S)-2-(4-methylphenyl)pyrrolidin-1-yl]pyrimidine-4,6-diol

The objective compound was obtained as a white powder by the same process as in Reference example 2 using (S)-2-(4-methylphenyl)pyrrolidine-1-carboximidamide hydrochloride instead of 2-(4-methylphenyl)pyrrolidine-1-carboximidamide hydrochloride.

Reference Example 8

5-Methoxy-2-[(2S)-2-(4-methylphenyl)pyrrolidin-1-yl]pyrimidine-4,6-diyl bis(trifluoromethanesulfonate)

435 mg of 5-methoxy-2-[(2S)-2-(4-methylphenyl)pyrrolidin-1-yl]pyrimidin-4,6-diol was dissolved in 8 mL of dichloromethane, and 0.48 mL of triethylamine and 0.53 mL of trifluoromethanesulfonic anhydride were added dropwise at 0° C., and the mixture was stirred for 30 minutes. Ice water was added to the reaction solution, subsequently the mixture was subjected to an extraction with dichloromethane, and the organic layer was washed with water, and was dried over magnesium sulfate. The solvent was distilled off under reduced pressure, and then the obtained residue was purified by silica gel column chromatography to obtain 690 mg of the objective compound as pale yellow oil.

Reference Example 9

2-(2-Methoxyphenyl)pyrrolidine

Step 1

Production of tert-butyl [4-(2-methoxyphenyl)-4-oxobutyl]carbamate 493 mg of tert-butyl {4-[methoxy(methyl)amino]-4-oxobutyl}carbamate (synthesized according to the method described in J. Med. Chem., 2009, 52, 7432) was added to 5 mL of THF, and 6 mL of 1.0 M 2-methoxyphenyl magnesium bromide/THF solution was added at 0° C. under an argon atmosphere, and then the mixture stirred for 2 hours, and further was stirred at room temperature overnight. Saturated aqueous ammonium chloride solution was added to the reaction mixture under ice-water cooling, and subsequently the mixture was subjected to an extraction with ethyl acetate, and the organic layer was washed with water and brine sequentially, and was dried over magnesium sulfate. The solvent was distilled off under reduced pressure, and then the obtained residue was purified by silica gel column chromatography to obtain 427 mg of the objective compound.

Step 2

Production of 5-(2-methoxyphenyl)-3,4-dihydro-2H-pyrrole 0.78 mL of trifluoroacetic acid was added to 404 mg of tert-butyl [4-(2-methoxyphenyl)-4-oxobutyl]carbamate at 0° C., and the mixture was stirred for one hour. The reaction mixture was made alkaline with 5 N sodium hydroxide aqueous solution, and then the mixture was subjected to an extraction with ethyl acetate. The obtained organic layer was washed with water and brine sequentially, and was dried over magnesium sulfate. The solvent was distilled off under reduced pressure, and then the obtained residue was purified by silica gel column chromatography to obtain 250 mg of the objective compound.

Step 3

Production of 2-(2-methoxyphenyl)pyrrolidine 285 mg of 5-(2-methoxyphenyl)-3,4-dihydro-2H-pyrrole was dissolved in methanol, and the solution was added with 123 mg of sodium borohydride at 0° C., and stirred for one hour. The reaction mixture was added with 6 N hydrochloric acid aqueous solution, and then stirred for one hour, and then added with 5 N sodium hydroxide aqueous solution to make it alkaline. The mixture was subjected to an extraction with ethyl acetate, and the obtained organic layer was washed with water and brine sequentially, and was dried over magnesium sulfate. The solvent was distilled off under reduced pressure, and then the obtained residue was purified by silica gel column chromatography to obtain 247 mg of the objective compound.

Reference Example 10

2-(2-Methoxy-4-methylphenyl)pyrrolidine

A suspension of 840 mg of 60% sodium hydride in 21 mL of THF was heated to reflux. 1.91 mL of N-vinyl-2-pyrolidone and 7 mL of THF solution of 2.95 g of ethyl 2-methoxy-4-methyl benzoate were added to the reaction mixture dropwise over 10 minutes, and further the mixture was heated to reflux stirring for 2 hours. The reaction mixture was cooled down, and then added with saturated ammonium chloride aqueous solution, and the mixture was subjected to an extraction with ethyl acetate, and the obtained organic layer was dried over magnesium sulfate. The solvent was distilled off under reduced pressure, and 6 N hydrochloric acid aqueous solution was added to the obtained residue and the mixture was stirred at 100° C. for 4 hours. The reaction solution was cooled down, and added with 30% sodium hydroxide aqueous solution to make it alkaline. The mixture was subjected to an extraction with dichloromethane, and the obtained organic layer was dried over magnesium sulfate. The solvent was distilled off under reduced pressure, and then the obtained residue was purified by silica gel column chromatography to obtain 858 mg of the objective compound.

Reference Example 11

2-(3-Methoxy-4-methylphenyl)pyrrolidine

The objective compound was obtained as yellow oil by the same process as in Reference example 10 using ethyl 3-methoxy-4-methylbenzoate instead of ethyl 2-methoxy-4-methylbenzoate.

Reference Example 12

2-(3-Methylphenyl)pyrrolidine

The objective compound was obtained as yellow oil by the same process as in Reference example 10 using ethyl 3-methylbenzoate instead of ethyl 2-methoxy-4-methylbenzoate.

Reference Example 13

6-[(5-Cyano-1,3-thiazol-2-yl)amino]-5-methoxy-2-[(2S)-2-(4-methylphenyl)pyrrolidin-1-yl]pyrimidin-4-yl trifluoromethanesulfonate 20 mL of 1,4-dioxane was added to 1.0 g of 5-methoxy-2-[(2S)-2-(4-methylphenyl)pyrrolidin-1-yl]pyrimidin-4,6-diyl bis(trifluoromethanesulfonate), 221 mg of 2-amino-1,3-thiazole-5-carbonitrile, 77 mg of Xantphos, 751 mg of tripotassium phosphate and 81 mg of $Pd_2(dba)_3$. The mixture was degassed, and then was stirred at 100° C. for 11 hours under an argon atmosphere. The reaction solution was diluted with ethyl acetate, and the obtained organic layer was washed with water, and dried over magnesium sulfate. The solvent was distilled off under reduced pressure, and then the obtained residue was purified by silica gel column chromatography to obtain 513 mg of the objective compound as a pale yellow powder.

MS (ESI) m/z 541 (M+H)$^+$

Reference Example 14

1-(2-{[tert-Butyl(diphenyl)silyl]oxy}ethyl)-4-(4,4,5,5-tetramethyl-1,3,2-dioxaborolan-2-yl)-1H-pyrazole 8.7 g of (2-bromoethoxy) (tert-butyl)diphenylsilane and 12 g of cesium carbonate were added to 3.3 g of 4-(4,4,5,5-tetramethyl-1,3,2-dioxaborolan-2-yl)-1H-pyrazole in 33 mL of acetonitrile, and the mixture was stirred at 80° C. for 6 hours. The reaction solution was diluted with ethyl acetate, and the obtained organic layer was washed with water and brine sequentially, and was dried over magnesium sulfate. The solvent was distilled off under reduced pressure to obtain 5.96 g of the objective compound as a pale yellow oil.

Reference Example 15

1-(2-Methoxyethyl)-4-(4,4,5,5-tetramethyl-1,3,2-dioxaborolan-2-yl)-1H-pyrazole

The objective compound was obtained as a brown oil by the same process as in Reference example 14 using 2-bromoethyl methyl ether instead of (2-bromoethoxy) (tert-butyl)diphenylsilane.

Reference Example 16

6-[(5-Cyano-1,3-thiazol-2-yl)amino]-5-ethyl-2-[(2S)-2-(4-methylphenyl)pyrrolidin-1-yl]pyrimidin-4-yl trifluoromethanesulfonate

Step 1

Production of 5-ethyl-2-[(2S)-2-(4-methylphenyl)pyrrolidin-1-yl]pyrimidine-4,6-diol 427 mg of the objective compound was obtained as a white powder by the same process as in Reference example 2 using 600 mg of (S)-2-(4-methylphenyl)pyrrolidine-1-carboximidamide hydrochloride, 0.61 mL of dimethyl ethylmalonate, 1.0 mL of 5 M sodium methoxide methanol solution and 18 mL of ethanol.

Step 2

Production of 5-ethyl-2-[(2S)-2-(4-methylphenyl)pyrrolidin-1-yl]pyrimidin-4,6-diyl bis(trifluoromethanesulfonate)

The objective compound was obtained as a yellow oil by the same process as in Reference example 8 using 5-ethyl-2-[(2S)-2-(4-methylphenyl)pyrrolidin-1-yl]pyrimidine-4,6-diol instead of 5-methoxy-2-[(2S)-2-(4-methylphenyl)pyrrolidin-1-yl]pyrimidine-4,6-diol.

Step 3

Production of 6-[(5-cyano-1,3-thiazol-2-yl)amino]-5-ethyl-2-[(2S)-2-(4-methylphenyl)pyrrolidin-1-yl]pyrimidin-4-yl trifluoromethanesulfonate The objective compound was obtained as a yellow oil by the same process as in Reference example 13 using 5-ethyl-2-[(2S)-2-(4-methylphenyl)pyrrolidin-1-yl]pyrimidin-4,6-diyl bis(trifluoromethanesulfonate) instead of 5-methoxy-2-[(2S)-2-(4-methylphenyl)pyrrolidin-1-yl]pyrimidin-4,6-diyl bis(trifluoromethanesulfonate).

Reference Example 17

6-[(5-Cyano-1,3-thiazol-2-yl)amino]-5-methyl-2-[(2S)-2-(4-methylphenyl)pyrrolidin-1-yl]pyrimidin-4-yl trifluoromethanesulfonate The objective compound was obtained as yellow oil by the same process as in Reference example 16 using dimethyl methylmalonate instead of dimethyl etyhlmalonate.

Step 3

Production of 6-[(5-Cyano-1,3-thiazol-2-yl)amino]-5-methyl-2-[(2S)-2-(4-methylphenyl)pyrrolidin-1-yl]pyrimidin-4-yl trifluoromethanesulfonate The objective compound was obtained as a yellow oil by the same process as in Reference example 13 using 5-methyl-2-[(2S)-2-(4-methylphenyl)pyrrolidin-1-yl]pyrimidin-4,6-diyl bis(trifluoromethanesulfonate) instead of 5-methoxy-2-[(2S)-2-(4-methylphenyl)pyrrolidin-1-yl]pyrimidin-4,6-diyl bis(trifluoromethanesulfonate).

Reference Example 18

5-Methoxy-2-[(2S)-2-(4-methylphenyl)pyrrolidin-1-yl]-6-(1,2,4-thiadiazol-5-ylamino)pyrimidin-4-yl trifluoromethanesulfonate 20 mL of 1,4-dioxane was added to 2.0 g of 5-methoxy-2-[(2S)-2-(4-methylphenyl)pyrrolidin-1-yl]pyrimidin-4,6-diyl bis(trifluoromethanesulfonate), 358 mg of 5-amino-1,2,4-thiadiazole, 153 mg of Xantphos, 1.5 g of tripotassium phosphate and 162 mg of $Pd_2(dba)_3$. The mixture was degassed, and then was stirred at 100° C. for 3 hours under an argon atmosphere. The reaction mixture was diluted with ethyl acetate, and the organic layer was washed with water, and dried over magnesium sulfate. The solvent was distilled off under reduced pressure, and then the obtained residue was purified by silica gel column chromatography to obtain 696 mg of the objective compound as yellow oil.

Example 1

2-({6-[(2S)-2-(4-Methylphenyl)pyrrolidin-1-yl]pyrazin-2-yl}amino)-1,3-thiazole-5-carbonitrile hydrochloride

Step 1

Production of 2-chloro-6-[(2S)-2-(4-methylphenyl)pyrrolidin-1-yl]pyrazine 100 mg of (2S)-2-(4-methylphenyl)pyrrolidine and 102 mg of 2,6-dichloropyrazine were dissolved in 2 mL of 1-butanol, and then the mixture was added with 130 μL of DIPEA, and stirred at 80° C. for 20 hours. After the reaction mixture was cooled to room temperature, the solvent was distilled off under reduced pressure, and then the obtained residue was purified by silica gel column chromatography to obtain 148 mg of the objective compound as a white amorphous.

Step 2

Production of 2-({6-[(2S)-2-(4-methylphenyl)pyrrolidin-1-yl]pyrazin-2-yl}amino)-1,3-thiazole-5-carbonitrile hydrochloride 122 mg of 2-chloro-6-[(2S)-2-(4-methylphenyl)pyrrolidin-1-yl]pyrazine, 169 mg of 2-amino-1,3-thiazole-5-carbonitrile, 257 mg of XPhos, 287 mg of tripotassium phosphate and 140 mg of $Pd_2(dba)_3 \cdot CHCl_3$ were added sequentially to 4 mL of degassed 1,4-dioxane, and then the mixture was stirred at 85° C. overnight under an argon atmosphere. After the reaction mixture was cooled to room temperature, the solvent was distilled off under reduced pressure, and then the obtained residue was purified by silica gel column chromatography to obtain 96 mg of 2-({6-[(2S)-2-(4-methylphenyl)pyrrolidin-1-yl]pyrazin-2-yl}amino)-1,3-thiazole-5-carbonitrile as a brown amorphous. Furthermore, the obtained compound was dissolved in ethanol, and then the solution was added with a chemical equivalent of 2 N hydrochloric acid, and the solvent was distilled off under reduced pressure, and the objective compound was obtained as a brown powder.

MS (ESI) m/z 363 (M+H)+

Elemental analysis value (as $C_{19}H_{18}N_6S \cdot HCl$)

Calculated value (%) C, 57.21; H, 4.80; N, 21.07.

Found value (%) C, 56.92; H, 4.77; N, 21.43.

Example 2

2-({5-Methyl-2-[2-(4-methylphenyl)pyrrolidin-1-yl]pyrimidin-4-yl}amino)-1,3-thiazole-5-carbonitrile 269 mg of 2,4-dichloro-5-methylpyrimidine, 191 mg of 2-amino-1,3-thiazole-5-carbonitrile, 700 mg of tripotassium phosphate, 95 mg of Xantphos and 76 mg of $Pd_2(dba)_3$ were added sequentially to 7 mL of degassed 1,4-dioxane, and the mixture was stirred at 100° C. for 2 hours under an argon atmosphere. Water was added to the reaction mixture, and the mixture was stirred for 30 minutes, and then the resulting precipitated solid was filtered off. Subsequently, 94 mg of the obtained solid, 0.20 mL of DIPEA and 78 mg of 2-(4-methylphenyl)pyrrolidine were added to 1 mL of NMP, and then the mixture was stirred at 180° C. for 30 minutes while irradiating microwave. After the reaction mixture was cooled to room temperature, the mixture was diluted with ethyl acetate, and was washed with water and brine sequentially, and then the obtained organic layer was dried over magnesium sulfate. The solvent was distilled off under reduced pressure, and then the resulting residue was purified by silica gel column chromatography to obtain 11 mg of the objective compound as a pale yellow powder.

MS (ESI) m/z 377 (M+H)−

Example 3

2-({5-Methoxy-2-[2-(4-methylphenyl)pyrrolidin-1-yl]-4,5'-bipyrimidin-6-yl}amino)-1,3-thiazole-5-carbonitrile Step 1

Production of 6-chloro-5-methoxy-2-[2-(4-methylphenyl)pyrrolidin-1-yl]-4,5'-bipyrimidine 100 mg of 4,6-dichloro-5-methoxy-2-[2-(4-methylphenyl)pyrrolidin-1-yl]pyrimidine (Reference example 3), 37 mg of pyrimidine-5-boronic acid, 122 mg of potassium carbonate and 12 mg of $[PdCl_2(dppf)_2]CH_2Cl_2$ were added sequentially to a degassed mixed solvent of 3 mL of 1,4-dioxane and 1 mL of water, and the mixture was stirred at 70° C. for 2 hours under an argon atmosphere. The mixture was diluted with ethyl acetate, and was washed with water and brine sequentially, and then the obtained organic layer was dried over magnesium sulfate. The solvent was distilled off under reduced pressure, and then the resulting residue was purified by silica gel column chromatography to obtain 41 mg of the objective compound.

Step 2

Production of 2-({5-methoxy-2-[2-(4-methylphenyl)pyrrolidin-1-yl]-4,5'-bipyrimidin-6-yl}amino)-1,3-thiazole-5-carbonitrile 2 mL of 1,4-dioxane was added to 40 mg of 6-chloro-5-methoxy-2-[2-(4-methylphenyl)pyrrolidin-1-yl]-4,5'-bipyrimidine, 13 mg of 2-amino-1,3-thiazole-5-carbonitrile, 18 mg of t-Butyl XPhos, 44 mg of tripotassium phosphate and 14 mg of $Pd_2(dba)_3$. After degassing, the mixture was stirred at 100° C. for one hour under an argon atmosphere. The mixture was diluted with ethyl acetate, and was washed with water, and then the obtained organic layer was dried over magnesium sulfate. The solvent was distilled off under reduced pressure, and then the obtained residue was purified by silica gel column chromatography to obtain 10 mg of the objective compound as a pale yellow powder.

MS (ESI) m/z 471 (M+H)+

Example 4

4-{6-[(5-Cyano-1,3-thiazol-2-yl)amino]-5-methoxy-2-[2-(4-methylphenyl)pyrrolidin-1-yl]pyrimidin-4-yl}benzamide The objective compound was obtained as a pale yellow powder by the same process as in Example 3 using 4-aminocarbonylphenylboronic acid instead of pyrimidine-5-boronic acid.

MS (ESI) m/z 512 (M+H)+

Example 5

2-({5-Methoxy-2-[2-(4-methylphenyl)pyrrolidin-1-yl]-6-(pyridin-3-yl)pyrimidin-4-yl}amino)-1,3-thiazole-5-carbonitrile The objective compound was obtained as a pale yellow powder by the same process as in Example 3 using diethyl (3-pyridyl)borane instead of pyrimidine-5-boronic acid.

MS (ESI) m/z 470 (M+H)+

Example 6

Methyl 6-[(5-cyano-1,3-thiazol-2-yl)amino]-2-[2-(4-methylphenyl) pyrrolidin-1-yl]pyrimidine-4-carboxylate Step 1

Production of methyl 2-chloro-6-[(5-cyano-1,3-thiazol-2-yl)amino]pyrimidine-4-carboxylate 500 mg of methyl 2,4-dichloropyrimidine-6-carboxylate, 302 mg of 2-amino-1,3-thiazole-5-carbonitrile, 1.02 g of tripotassium phosphate, 139 mg of Xantphos and 110 mg of $Pd_2(dba)_3$ were added sequentially to 5 mL of degassed 1,4-dioxane, and the mixture was stirred at 100° C. for 3 hours under an argon atmosphere. The reaction mixture was diluted with water, and 0.27 mL of acetic acid was added, and then the mixture was stirred at room temperature for 10 minutes. A precipitated solid was filtered to obtain 302 mg of the objective compound.

Step 2

Production of methyl 6-[(5-cyano-1,3-thiazol-2-yl)amino]-2-[2-(4-methylphenyl) pyrrolidin-1-yl]pyrimidine-4-carboxylate 300 mg of methyl 2-chloro-6-[(5-cyano-1,3-thiazol-2-yl)amino]pyrimidine-4-carboxylate, 0.54 mL of DIPEA and 179 mg of 2-(4-methylphenyl)pyrrolidine were added to 2 mL of NMP, and then the mixture was stirred at 180° C. for 30 minutes while irradiating microwave. After cooling to room temperature, the mixture was diluted with ethyl acetate, and was washed with water and brine sequentially, and then the obtained organic layer was dried over magnesium sulfate. The solvent was distilled off under reduced pressure, and then the resulting residue was purified by silica gel column chromatography to obtain 215 mg of the objective compound as a pale yellow powder.

MS (ESI) m/z 421 (M+H)$^+$

Example 7

6-[(5-Cyano-1,3-thiazol-2-yl)amino]-2-[2-(4-methylphenyl) pyrrolidin-1-yl]pyrimidine-4-carboxylic acid 213 mg of methyl 6-[(5-cyano-1,3-thiazol-2-yl)amino]-2-[2-(4-methylphenyl) pyrrolidin-1-yl]pyrimidine-4-carboxylate (Example 6) was dissolved in 6 mL of methanol, and 0.61 mL of 10% sodium hydroxide aqueous solution was added to the solution, and then the mixture was stirred at room temperature for three days. The solvent was distilled off under reduced pressure, and then the residue was diluted with water, and was added with 10% hydrochloric acid and the pH was adjusted to 3. The reaction solution was subjected to an extraction with ethyl acetate. The obtained organic layer was washed with water and brine sequentially and then dried over magnesium sulfate. After the solvent was distilled off under reduced pressure, a precipitated solid was filtered to obtain 145 mg of the objective compound.

MS (ESI) m/z 407 (M+H)$^+$

Example 8

2-({5-Methyl-2-[2-(4-methylphenyl)pyrrolidin-1-yl]-6-(1-methyl-1H-pyrazol-4-yl)pyrimidin-4-yl}amino)-1,3-thiazole-5-carbonitrile The objective compound was obtained as an orange powder by the same process as in Example 3 using 4,6-dichloro-5-methyl-2-[2-(4-methylphenyl)pyrrolidin-1-yl]pyrimidine instead of 4,6-dichloro-5-methoxy-2-[2-(4-methylphenyl)pyrrolidin-1-yl]pyrimidine, and using 1-methyl-4-(4,4,5,5-tetramethyl-1,3,2-dioxaborolan-2-yl)-1H-pyrazole instead of pyrimidine-5-boronic acid.

MS (ESI) m/z 457 (M+H)$^+$

Example 9

2-({5-Methoxy-6-methyl-2-[(2S)-2-(4-methylphenyl)pyrrolidin-1-yl]pyrimidin-4-yl}amino)-1,3-thiazole-5-carbonitrile maleate

Step 1

Production of 5-methoxy-6-methyl-2-[(2S)-2-(4-methylphenyl)pyrrolidin-1-yl]pyrimidin-4-yl trifluoromethanesulfonate To a degassed mixed solvent of 21 mL of 1,4-dioxane and 7 mL of water were added sequentially 2.0 g of 5-methoxy-2-[(2S)-2-(4-methylphenyl)pyrrolidin-1-yl]pyrimidine-4,6-diyl bis(trifluoromethanesulfonate) (Reference example 8), 205 mg of methylboronic acid, 977 mg of potassium carbonate and 144 mg of [PdCl$_2$(dppf)$_2$]CH$_2$Cl$_2$, and then the mixture was stirred at 85° C. for 2 hours under an argon atmosphere. The reaction mixture was diluted with ethyl acetate, and washed with water and brine sequentially, and then the obtained organic layer was dried over magnesium sulfate. After the solvent was distilled off under reduced pressure, the obtained residue was purified by silica gel column chromatography to obtain 352 mg of the objective compound.

Step 2

Production of 2-({5-methoxy-6-methyl-2-[(2S)-2-(4-methylphenyl)pyrrolidin-1-yl]pyrimidin-4-yl}amino)-1,3-thiazole-5-carbonitrile maleate 6 mL of 1,4-dioxane was added to 350 mg of 5-methoxy-6-methyl-2-[(2S)-2-(4-methylphenyl)pyrrolidin-1-yl]pyrimidin-4-yl trifluoromethanesulfonate, 101 mg of 2-amino-1,3-thiazole-5-carbonitrile, 138 mg of t-Butyl XPhos, 344 mg of tripotassium phosphate and 111 mg of Pd$_2$(dba)$_3$. After degassing, the mixture was stirred at 100° C. for one hour under an argon atmosphere. The reaction mixture was diluted with ethyl acetate, and was washed with water, and then the organic layer was dried over magnesium sulfate. After the solvent was distilled off under reduced pressure, the obtained residue was purified by silica gel column chromatography to obtain 212 mg of 2-({5-methoxy-6-methyl-2-[(2S)-2-(4-methylphenyl)pyrrolidin-1-yl]pyrimidin-4-yl}amino)-1,3-thiazole-5-carbonitrile as a pale yellow amorphous. Furthermore, the obtained compound was dissolved in ethanol, and then was added with an equivalent amount of maleic acid, and the solvent was distilled off under reduced pressure, and the objective compound was obtained as a pale yellow powder.

MS (ESI) m/z 407 (M+H)+
Elemental analysis value (as C$_{25}$H$_{26}$N$_6$O$_5$S+0.3 Et$_2$O)
Calculated value (%) C, 57.76; H, 5.37; N, 15.43.
Found value (%) C, 57.41; H, 5.30; N, 15.11.

Example 10

2-({5-Methoxy-2-[(2S)-2-(4-methylphenyl)pyrrolidin-1-yl]-6-(1-methyl-1H-pyrazol-4-yl)pyrimidin-4-yl}amino)-1,3-thiazole-5-carbonitrile

Step 1

Production of 5-methoxy-2-[(2S)-2-(4-methylphenyl)pyrrolidin-1-yl]-6-(1-methyl-1H-pyrazol-4-yl)pyrimidin-4-yl trifluoromethanesulfonate 293 mg of 5-methoxy-2-[(2S)-2-(4-methylphenyl)pyrrolidin-1-yl]pyrimidin-4,6-diyl bis(trifluoromethanesulfonate), 108 mg of 1-methyl-4-(4,4,5,5-tetramethyl-1,3,2-dioxaborolan-2-yl)-1H-pyrazole, 143 mg of potassium carbonate and 21 mg of [PdCl$_2$(dppf)$_2$]CH$_2$Cl$_2$ were sequentially added to a degassed mixed solvent of 6 mL of 1,4-dioxane and 2 mL of water, and the mixture was stirred at 70° C. for one hour under an argon atmosphere. The reaction mixture was diluted with ethyl acetate, and was washed with water and brine, and then the organic layer was dried over magnesium sulfate. After the solvent was distilled off under reduced pressure, the obtained residue was purified by silica gel column chromatography to obtain 154 mg of the objective compound.

Step 2

Production of 2-({5-methoxy-2-[(2S)-2-(4-methylphenyl)pyrrolidin-1-yl]-6-(1-methyl-1H-pyrazol-4-yl)pyrimidin-4-yl}amino)-1,3-thiazole-5-carbonitrile 3 mL of 1,4-dioxane was added to 152 mg of 5-methoxy-2-[(2S)-2-(4-methylphenyl)pyrrolidin-1-yl]-6-(1-methyl- 1H-pyrazol-4-yl)pyrimidin-4-yl trifluoromethanesulfonate, 38 mg of 2-amino-1,3-thiazole-5-carbonitrile, 52 mg of t-Butyl XPhos, 130 mg of tripotassium phosphate and 42 mg of $Pd_2(dba)_3$. After degassing, the mixture was stirred at 100° C. for one hour under an argon atmosphere. The reaction mixture was diluted with ethyl acetate, and was washed with water, and then the obtained organic layer was dried over magnesium sulfate. After the solvent was distilled off under reduced pressure, the obtained residue was purified by silica gel column chromatography to obtain the objective compound as a pale yellow powder.
MS (ESI) m/z 473 (M+H)$^+$ Example 11

2-({5-Methoxy-2-[2-(4-methylphenyl)pyrrolidin-1-yl]-6-(1, 3-oxazol-5-yl)pyrimidin-4-yl}amino)-1,3-thiazole-5-carbonitrile The objective compound was obtained as a pale yellow powder by the same process as in Example 3 using 5-(4,4,5,5-tetramethyl-1,3,2-dioxaborolan-2-yl)-2-(tripropan-2-yl-silyl)-1,3-oxazole (synthesized according to the method described in Tetrahedron, 2009, 65, 6348) instead of pyrimidine-5-boronic acid.
MS (ESI) m/z 460 (M+H)$^+$ Example 12

6-[(5-Cyano-1,3-thiazol-2-yl)amino]-N-[(2R)-1-hydroxypropan-2-yl]-2-[2-(4-methylphenyl)pyrrolidin-1-yl]pyrimidine-4-carboxamide 40 mg of 6-[(5-cyano-1,3-thiazol-2-yl)amino]-2-[2-(4-methylphenyl) pyrrolidin-1-yl]pyrimidine-4-carboxylic acid (Example 7) was dissolved in 1 mL of DMF, and then 77 mg of PyBOP (Registered Trademark), 84 mL of DIPEA and 22 mg of D-alaninol were added sequentially to the solution, and the mixture was stirred at room temperature for 3 hours. The reaction mixture was diluted with ethyl acetate, and was washed with water and brine, and then the obtained organic layer was dried over magnesium sulfate. After the solvent was distilled off under reduced pressure, the obtained residue was purified by silica gel column chromatography to obtain 4 mg of the objective compound as a pale yellow powder.
MS (ESI) m/z 464 (M+H)$^+$ Example 13

2-({5-Methoxy-2-[2-(4-methylphenyl)pyrrolidin-1-yl]-6-[4-(methylsulfonyl)phenyl]pyrimidin-4-yl}amino)-1,3-thiazole-5-carbonitrile The objective compound was obtained as a yellow powder by the same process as in Example 3 using 4-methanesulfonylphenylboronic acid instead of pyrimidine-5-boronic acid.
MS (ESI) m/z 547 (M+H)$^+$ Example 14

2-({5-Methoxy-2-[2-(2-methoxy-4-methylphenyl)pyrrolidin-1-yl]pyrimidin-4-yl}amino)-1,3-thiazole-5-carbonitrile The objective compound was obtained as a pale yellow powder by the same process as in Example 2 using 2,4-dichloro-5-methoxypyrimidine instead of 2,4-dichloro-5-methylpyrimidine, and using 2-(2-methoxy-4-methylphenyl)pyrrolidine instead of 2-(4-methylphenyl)pyrrolidine.
MS (ESI) m/z 423 (M+H)$^+$ Example 15

2-({6-(6-Methoxypyridin-3-yl)-5-methyl-2-[2-(4-methylphen yl)pyrrolidin-1-yl]pyrimidin-4-yl}amino)-1,3-thiazole-5-carbonitrile The objective compound was obtained as a pale yellow powder by the same process as in Example 3 using 4,6-dichloro-5-methyl-2-[2-(4-methylphenyl)pyrrolidin-1-yl]pyrimidine (Reference example 5) instead of 4,6-dichloro-5-methoxy-2-[2-(4-methylphenyl)pyrrolidin-1-yl]pyrimidine, and using 2-methoxy-5-pyridineboronic acid instead of pyrimidine-5-boronic acid.
MS (ESI) m/z 484 (M+H)$^+$ Example 16

2-({6-(6-Hydroxypyridin-3-yl)-5-methyl-2-[2-(4-methylphen yl)pyrrolidin-1-yl]pyrimidin-4-yl}amino)-1,3-thiazole-5-carbonitrile 100 mg of 2-({6-(6-methoxypyridin-3-yl)-5-methyl-2-[2-(4-methylphen yl)pyrrolidin-1-yl]pyrimidin-4-yl}amino)-1,3-thiazole-5-carbonitrile was dissolved in 3 mL of acetonitrile, 93 mg of NaI and 79 μL of trimethylsilyl chloride were added to the solution, and the mixture was stirred at 70° C. for one hour under an argon atmosphere. The reaction mixture was diluted with ethyl acetate and water, and saturated sodium bicarbonate aqueous solution was added to the mixture to adjust the pH to 9, and then the mixture was subjected to an extraction. The obtained organic layer was washed with brine, and then was dried over magnesium sulfate. After the solvent was distilled off under reduced pressure, the obtained solid was washed with ethyl acetate to obtain the objective compound as a yellow powder.
MS (ESI) m/z 470 (M+H)$^+$ Example 17

2-({5-Bromo-6-methyl-2-[2-(4-methylphenyl)pyrrolidin-1-yl]pyrimidin-4-yl}amino)-1,3-thiazole-5-carbonitrile Step 1

Production of 2-({6-methyl-2-[2-(4-methylphenyl)pyrrolidin-1-yl]pyrimidin-4-yl}amino)-1,3-thiazole-5-carbonitrile The objective compound was obtained as a white powder by the same process as in Example 2 using 2,4-dichloro-6-methylpyrimidine instead of 2,4-dichloro-5-methylpyrimidine.

Step 2

Production of 2-({5-bromo-6-methyl-2-[2-(4-methylphenyl)pyrrolidin-1-yl]pyrimidin-4-yl}amino)-1,3-thiazole-5-carbonitrile 157 mg of 2-({6-[2-methyl-2-(4-methylphenyl)pyrrolidin-1-yl]pyrimidin-4-yl}amino)-1,3-thiazole-5-carbonitrile was dissolved in 4 mL of chloroform, 89 mg of NBS was added to the solution, and the mixture was stirred at room temperature for 30 minutes. After the solvent was distilled off under reduced pressure, the obtained residue was purified by silica gel column chromatography to obtain 144 mg of the objective compound as a white powder.

MS (ESI) m/z 455 (M+H)$^+$

Example 18

2-({6-Cyclopropyl-5-methoxy-2-[2-(4-methylphenyl)pyrrolidin-1-yl]pyrimidin-4-yl}amino)-1,3-thiazole-5-carbonitrile The objective compound was obtained as a white powder by the same process as in Example 3 using cyclopropylboronic acid instead of pyrimidine-5-boronic acid.

MS (ESI) m/z 433 (M+H)$^+$

Example 19

2-({5-Methoxy-2-[2-(4-methylphenyl)pyrrolidin-1-yl]pyrimidin-4-yl}amino)-1,3-thiazole-5-carbonitrile The objective compound was obtained as a pale yellow powder by the same process as in Example 2 using 2,4-dichloro-5-methoxypyrimidine instead of 2,4-dichloro-5-methylpyrimidine.

MS (ESI) m/z 393 (M+H)$^+$

Example 20

2-({3-Methyl-6-[(2S)-2-(4-methylphenyl)pyrrolidin-1-yl]pyrazin-2-yl}amino)-1,3-thiazole-5-carbonitrile hydrochloride Step 1

Production of 2-chloro-6-[(2S)-2-(4-methylphenyl)pyrrolidin-1-yl]pyrazine 3.0 g of 2,6-dichloropyrazine was dissolved in 12 mL of 1,2-dichloroethane, and 0.95 mL of DIPEA was added to the solution. 800 mg of (2S)-2-(4-methylphenyl)pyrrolidine in 4 mL of 1,2-dichloroethane was added to the mixture under ice-water cooling, and then the mixture was stirred at room temperature for 48 hours. After the solvent was distilled off under reduced pressure, the resulting residue was purified by silica gel column chromatography to obtain 685 mg of the objective compound as a white amorphous.

Step 2

Production of 2-bromo-3-chloro-5-[(2S)-2-(4-methylphenyl)pyrrolidin-1-yl]pyrazine 525 mg of 2-chloro-6-[(2S)-2-(4-methylphenyl)pyrrolidin-1-yl]pyrazine was dissolved in 10 mL of chloroform, and 375 mg of NBS was added to the solution, and then the mixture was stirred for 2 hours under ice water cooling. The reaction mixture was diluted with chloroform, and was washed with water and brine sequentially, and then the obtained organic layer was dried over magnesium sulfate. After the solvent was distilled off under reduced pressure, the resulting residue was purified by silica gel column chromatography to obtain 462 mg of the objective compound as a pale yellow powder.

Step 3

Production of 3-chloro-2-methyl-5-[(2S)-2-(4-methylphenyl)pyrrolidin-1-yl]pyrazine 460 mg of 2-bromo-3-chloro-5-[(2S)-2-(4-methylphenyl)pyrrolidin-1-yl]pyrazine, 190 mg of methylboronic acid, 538 mg of potassium carbonate and 53 mg of [PdCl$_2$(dppf)$_2$]CH$_2$Cl$_2$ were added sequentially to a degassed mixed solvent of 10 mL of 1,4-dioxane and 3 mL of water, and the mixture was stirred at 100° C. for 8 hours under an argon atmosphere. The reaction mixture was diluted with ethyl acetate, and was washed with water and brine sequentially, and then the obtained organic layer was dried over magnesium sulfate. After the solvent was distilled off under reduced pressure, the resulting residue was purified by silica gel column chromatography to obtain 300 mg of the objective compound.

Step 4

Production of 2-({3-methyl-6-[(2S)-2-(4-methylphenyl)pyrrolidin-1-yl]pyrazin-2-yl}amino)-1,3-thiazole-5-carbonitrile hydrochloride 5 mL of 1,4-dioxane was added to 190 mg of 3-chloro-2-methyl-5-[(2S)-2-(4-methylphenyl)pyrrolidin-1-yl]pyrazine, 124 mg of 2-amino-1,3-thiazole-5-carbonitrile, 189 mg of XPhos, 280 mg of tripotassium phosphate and 90 mg of Pd$_2$(dba)$_3$. After degassing, the mixture was stirred at 100° C. for 2 hours under an argon atmosphere. The reaction mixture was diluted with ethyl acetate, and was washed with water, and then the obtained organic layer was dried over magnesium sulfate. After the solvent was distilled off under reduced pressure, the resulting residue was purified by silica gel column chromatography to obtain 157 mg of 2-({3-methyl-6-[(2S)-2-(4-methylphenyl)pyrrolidin-1-yl]pyrazin-2-yl}amino)-1,3-thiazole-5-carbonitrile as a pale yellow amorphous. Furthermore, the obtained compound was dissolved in methanol, and then was added with an equivalent amount of 1 N hydrochloric acid, and the solvent was distilled off under reduced pressure to obtain the objective compound as a yellow powder.

MS (ESI) m/z 377 (M+H)$^+$

Elemental analysis value (as C$_{20}$H$_{20}$N$_6$S.1 HCl+0.2H$_2$O)
Calculated value (%) C, 57.67; H, 5.18; N, 20.18.
Found value (%) C, 57.80; H, 5.02; N, 20.36.

Example 21

2-({6-[2-(4-Fluorophenyl)pyrrolidin-1-yl]-3-(1,3-oxazol-5-yl)pyrazin-2-yl}amino)-1,3-thiazole-5-carbonitrile Step 1

Production of 2-bromo-3-chloro-5-[2-(4-fluorophenyl)pyrrolidin-1-yl]pyrazine

The objective compound was obtained as a pale yellow powder by the same process as in Steps 1 and 2 of Example 20 using 2-(4-fluorophenyl)pyrrolidine instead of (2S)-2-(4-methylphenyl)pyrrolidine.

Step 2

Production of 3-chloro-5-[2-(4-fluorophenyl)pyrrolidin-1-yl]-2-[2-(tripropan-2-ylsilyl)-1,3-oxazol-5-yl]pyrazine 120 mg of 2-bromo-3-chloro-5-[2-(4-fluorophenyl)pyrrolidin-1-yl]pyrazine, 190 mg of 5-(tributylstannyl)-2-(triisopropylsilyl)oxazole (synthesized according to the method described in WO 2007/17096), 43 mg of lithium chloride and 39 mg of Pd(PPh$_3$)$_4$ were added sequentially to 3.5 mL of degassed DMF, and the mixture was stirred at 100° C. for 2.5 hours under an argon atmosphere. After the reaction mixture was filtered with Celite (Registered Trademark), the mother liquid was distilled off under reduced pressure. The obtained residue was purified by silica gel column chromatography to obtain 125 mg of the objective compound as pale orange oil.

Step 3

Production of 2-({6-[2-(4-fluorophenyl)pyrrolidin-1-yl]-3-[2-(tripropan-2-ylsilyl)-1,3-oxazol-5-yl]pyrazin-2-yl}amino)-1,3-thiazole-5-carbonitrile 3 mL of 1,4-dioxane was added to 125 mg of 3-chloro-5-[2-(4-fluorophenyl)pyrrolidin-1-yl]-2-[2-(tripropan-2-ylsilyl)-1,3-oxazol-5-yl]pyrazine, 47 mg of 2-amino-1,3-thiazole-5-carbonitrile, 63 mg of t-Butyl XPhos, 116 mg of tripotassium phosphate and 34 mg of Pd$_2$(dba)$_3$. After degassing, the mixture was stirred at 100° C. for 3.5 hours under an argon atmosphere. After the reaction mixture was filtered with Celite (Registered Trademark), the mother liquid was distilled off under reduced pressure. The obtained residue was purified by silica gel column chromatography to obtain 126 mg of the objective compound as a pale yellow amorphous.

Step 4

Production of 2-({6-[2-(4-fluorophenyl)pyrrolidin-1-yl]-3-(1,3-oxazol-5-yl)pyrazin-2-yl}amino)-1,3-thiazole-5-carbonitrile 126 mg of 2-({6-[2-(4-fluorophenyl)pyrrolidin-1-yl]-3-[2-(tripropan-2-ylsilyl)-1,3-oxazol-5-yl]pyrazin-2-yl}amino)-1,3-thiazole-5-carbonitrile was dissolved in 2 mL of THF, and 0.43 mL of 1 M tetrabutylammonium fluoride/THF solution was added to the solution. The mixture was stirred at room temperature for 15 minutes, and then the reaction mixture was diluted with ethyl acetate. The organic layer was washed with water and brine sequentially, and was dried over magnesium sulfate. After the solvent was distilled off under reduced pressure, the resulting residue was purified by silica gel column chromatography to obtain 59 mg of the objective compound as an orange amorphous
MS (ESI) m/z 434 (M+H)$^+$

Example 22

2-({6-[2-(4-Fluorophenyl)pyrrolidin-1-yl]-3-(pyrimidin-5-yl)pyrazin-2-yl}amino)-1,3-thiazole-5-carbonitrile The objective compound was obtained as a pale yellow powder by the same process as in Example 20 using 2-(4-fluorophenyl)pyrrolidine instead of (2S)-2-(4-methylphenyl)pyrrolidine in Step 1, and using pyrimidine-5-boronic acid instead of methylboronic acid in Step 3.
MS (ESI) m/z 445 (M+H)$^+$

Example 23

2-({3-Cyclopropyl-6-[2-(2-methoxy-4-methylphenyl)pyrrolidin-1-yl]pyrazin-2-yl}amino)-1,3-thiazole-5-carbonitrile The objective compound was obtained as an orange amorphous by the same process as in Example 20 using 2-(2-methoxy-4-methylphenyl)pyrrolidine instead of (2S)-2-(4-methylphenyl)pyrrolidine in Step 1, and using cyclopropylboronic acid instead of methylboronic acid in Step 3.
MS (ESI) m/z 433 (M+H)$^+$

Example 24

2-({3-Cyclopropyl-6-[2-(2-methoxyphenyl)pyrrolidin-1-yl]pyrazin-2-yl}amino)-1,3-thiazole-5-carbonitrile The objective compound was obtained as a red powder by the same process as in Example 20 using 2-(2-methoxyphenyl)pyrrolidine instead of (2S)-2-(4-methylphenyl)pyrrolidine in Step 1, and using cyclopropylboronic acid instead of methylboronic acid in Step 3.
MS (ESI) m/z 419 (M+H)$^+$

Example 25

2-({6-[2-(4-Fluorophenyl)pyrrolidin-1-yl]-3-(furan-3-yl)pyrazin-2-yl}amino)-1,3-thiazole-5-carbonitrile The objective compound was obtained as a pale yellow powder by the same process as in Example 20 using 2-(4-fluorophenyl)pyrrolidine instead of (2S)-2-(4-methylphenyl)pyrrolidine in Step 1, and using furan-3-boronic acid instead of methylboronic acid in Step 3.
MS (ESI) m/z 433 (M+H)$^+$

Example 26

2-({6-[2-(4-Fluorophenyl)pyrrolidin-1-yl]-3-(pyridin-4-yl)pyrazin-2-yl}amino)-1,3-thiazole-5-carbonitrile The objective compound was obtained as a pale yellow powder by the same process as in Example 20 using 2-(4-fluorophenyl)pyrrolidine instead of (2S)-2-(4-methylphenyl)pyrrolidine in Step 1, and using 4-pyridineboronic acid instead of methylboronic acid in Step 3.
MS (ESI) m/z 444 (M+H)$^+$

Example 27

2-({6-[2-(4-Methylphenyl)pyrrolidin-1-yl]-4-(trifluoromethyl)pyridin-2-yl}amino)-1,3-thiazole-5-carbonitrile

Step 1

Production of 2-chloro-6-[2-(4-methylphenyl)pyrrolidin-1-yl]-4-(trifluoromethyl)pyridine 112 mg of 2-(4-methylphenyl)pyrrolidine and 100 mg of 2,6-dichloropyrazine were dissolved in 1 mL of 1-butanol, and 302 μL of DIPEA was added to the solution, and the mixture was stirred at 100° C. for 8 hours. After the reaction mixture was cooled to room temperature, the solvent was distilled off under reduced pressure. The resulting residue was purified by silica gel column chromatography to obtain 139 mg of the objective compound as a white amorphous.

Step 2

Production of 2-({6-[2-(4-methylphenyl)pyrrolidin-1-yl]-4-(trifluoromethyl)pyridin-2-yl}amino)-1,3-thiazole-5-carbonitrile 139 mg of 2-chloro-6-[2-(4-methylphenyl)pyrrolidin-1-yl]-4-(trifluoromethyl)pyridine, 51 mg of 2-amino-1,3-thiazole-5-carbonitrile, 117 mg of XPhos, 122 mg of tripotassium phosphate and 56 mg of $Pd_2(dba)_3$ were added sequentially to 4 mL of degassed 1,4-dioxane, and the mixture was stirred at 100° C. for 3 hours under an argon atmosphere. After the reaction mixture was cooled to room temperature, the solvent was distilled off under reduced pressure. The obtained residue was purified by silica gel column chromatography to obtain 97 mg of the objective compound as a yellow powder.
MS (ESI) m/z 430 $(M+H)^+$ Example 28

2-({6-[2-(4-Fluorophenyl)pyrrolidin-1-yl]-3-(1-methyl-1H-pyrazol-4-yl)pyrazin-2-yl}amino)-1,3-thiazole-5-carbonitrile The objective compound was obtained as a brown powder by the same process as in Example 20 using 2-(4-fluorophenyl)pyrrolidine instead of (2S)-2-(4-methylphenyl)pyrrolidine in Step 1, and using 1-methyl-4-(4,4,5,5-tetramethyl-1,3,2-dioxaborolan-2-yl)-1H-pyrazole instead of methylboronic acid in Step 3.
MS (ESI) m/z 447 $(M+H)^+$ Example 29

3-Methyl-6-[(2S)-2-(4-methylphenyl)pyrrolidin-1-yl]-N-(5-methyl-1,3-thiazol-2-yl)pyrazine-2-amine The objective compound was obtained as an orange powder by the same process as in Example 20 using 2-amino-5-methylthiazole instead of 2-amino-1,3-thiazole-5-carbonitrile in Step 4.
MS (ESI) m/z 366 $(M+H)^+$ Example 30

2-({6-[2-(2-Methoxy-4-methylphenyl)pyrrolidin-1-yl]pyrazin-2-yl}amino)-1,3-thiazole-5-carbonitrile The objective compound was obtained as a pale yellow powder by the same process as in Example 1 using 2-(2-methoxy-4-methylphenyl)pyrrolidine (Reference example 10) instead of (2S)-2-(4-methylphenyl)pyrrolidine in Step 1.
MS (ESI) m/z 393 $(M+H)^+$ Example 31

6-[2-(4-Chlorophenyl)pyrrolidin-1-yl]-3-cyclopropyl-N-(5-methyl-1,3-thiazol-2-yl)pyrazine-2-amine The objective compound was obtained as a pale red powder by the same process as in Example 20 using 2-(4-chlorophenyl)pyrrolidine instead of (2S)-2-(4-methylphenyl)pyrrolidine in Step 1, using cyclopropylboronic acid instead of methylboronic acid in Step 3, and using 2-amino-5-methylthiazole instead of 2-amino-1,3-thiazole-5-carbonitrile in Step 4.
MS (ESI) m/z 412 $(M+H)^+$ Example 32

2-({6-[2-(3,5-Dimethoxyphenyl)pyrrolidin-1-yl]pyrazin-2-yl}amino)-1,3-thiazol-5-carbonitrile The objective compound was obtained as a brown powder by the same process as in Example 1 using 2-(3,5-dimethoxyphenyl)pyrrolidine (synthesized according to the method described in J. Org. Chem., 2001, 66, 6207) instead of (2S)-2-(4-methylphenyl)pyrrolidine in Step 1.
MS (ESI) m/z 409 $(M+H)^+$ Example 33

2-({6-[2-(3-Methoxy-4-methylphenyl)pyrrolidin-1-yl]pyrazin-2-yl}amino)-1,3-thiazole-5-carbonitrile The objective compound was obtained as a brown powder by the same process as in Example 1 using 2-(3-methoxy-4-methylphenyl)pyrrolidine (Reference example 11) instead of (2S)-2-(4-methylphenyl)pyrrolidine in Step 1.
MS (ESI) m/z 393 $(M+H)^+$ Example 34

3-Cyclopropyl-6-[(2S)-2-(4-methylphenyl)pyrrolidin-1-yl]-N-(5-methyl-1,3-thiazol-2-yl)pyrazine-2-amine The objective compound was obtained as a pale yellow powder by the same process as in Example 20 using cyclopropylboronic acid instead of methylboronic acid in Step 3, and using 2-amino-5-methylthiazole instead of 2-amino-1,3-thiazole-5-carbonitrile in Step 4.
MS (ESI) m/z 392 $(M+H)^+$ Example 35

2-({3-Cyclopropyl-6-[(2S)-2-(4-methylphenyl)pyrrolidin-1-yl]pyrazin-2-yl}amino)-1,3-thiazole-5-carbonitrile The objective compound was obtained as a pale yellow amorphous by the same process as in Example 20 using cyclopropylboronic acid instead of methylboronic acid in Step 3.
MS (ESI) m/z 403 $(M+H)^+$ Example 36

2-({6-[(2S)-2-(4-Chlorophenyl)pyrrolidin-1-yl]-3-cyclopropylpyrazin-2-yl}amino)-1,3-thiazole-5-carbonitrile The objective compound was obtained as a red powder by the same process as in Example 20 using (2S)-2-(4-chlorophenyl)pyrrolidine instead of (2S)-2-(4-methylphenyl)pyrrolidine in Step 1, and using cyclopropylboronic acid instead of methylboronic acid in Step 3.
MS (ESI) m/z 423 $(M+H)^+$

Example 37

2-({6-[2-(4-Methoxyphenyl)pyrrolidin-1-yl]pyrazin-2-yl}amino)-1,3-thiazole-5-carbonitrile The objective compound was obtained as a pale yellow powder by the same process as in Example 1 using 2-(4-methoxyphenyl)pyrrolidine instead of (2S)-2-(4-methylphenyl)pyrrolidine in Step 1.
MS (ESI) m/z 379 (M+H)$^+$

Example 38

2-({6-[2-(3-Methoxyphenyl)pyrrolidine-1-yl]pyrazin-2-yl}amino)-1,3-thiazole-5-carbonitrile The objective compound was obtained as a pale yellow powder by the same process as in Example 1 using 2-(3-methoxyphenyl)pyrrolidine (synthesized according to the method described in US 2006/293316) instead of (2S)-2-(4-methylphenyl)pyrrolidine in Step 1.
MS (ESI) m/z 379 (M+H)$^+$

Example 39

2-[(6-{2-[4-(Trifluoromethyl)phenyl]pyrrolidin-1-yl}pyrazin-2-yl)amino]-1,3-thiazole-5-carbonitrile The objective compound was obtained as a pale yellow powder by the same process as in Example 1 using 2-(4-trifluoromethylphenyl)pyrrolidine instead of (2S)-2-(4-methylphenyl)pyrrolidine in Step 1.
MS (ESI) m/z 417 (M+H)$^+$

Example 40

2-({3-Cyclopropyl-6-[2-(4-fluorophenyl)pyrrolidin-1-yl]pyrazin-2-yl}amino)-1,3-thiazole-5-carbonitrile The objective compound was obtained as a yellow powder by the same process as in Example 20 using 2-(4-fluorophenyl)pyrrolidine instead of (2S)-2-(4-methylphenyl)pyrrolidine in Step 1, and using cyclopropylboronic acid instead of methylboronic acid in Step 3.
MS (ESI) m/z 407 (M+H)$^+$

Example 41

2-({6-[2-(4-Fluorophenyl)pyrrolidin-1-yl]-3-methylpyrazin-2-yl}amino)-1,3-thiazole-5-carbonitrile The objective compound was obtained as a pale green powder by the same process as in Example 20 using 2-(4-fluorophenyl)pyrrolidine instead of (2S)-2-(4-methylphenyl)pyrrolidine in Step 1.
MS (ESI) m/z 381 (M+H)$^+$

Example 42

2-({6-[2-(4-Chlorophenyl)pyrrolidin-1-yl]-3-methylpyrazin-2-yl}amino)-1,3-thiazole-5-carbonitrile The objective compound was obtained as a pale yellow powder by the same process as in Example 20 using 2-(4-chlorophenyl)pyrrolidine instead of (2S)-2-(4-methylphenyl)pyrrolidine in Step 1.
MS (ESI) m/z 397 (M+H)$^+$

Example 43

2-({3,5-Dimethyl-6-[2-(4-methylphenyl)pyrrolidin-1-yl]pyrazin-2-yl}amino)-1,3-thiazole-5-carbonitrile

Step 1

Production of 2,6-dibromo-3-chloro-5-[2-(4-methylphenyl)pyrrolidin-1-yl]pyrazine 338 mg of 2-bromo-3-chloro-5-[2-(4-methylphenyl)pyrrolidin-1-yl]pyrazine (synthesized according to the method described in Step 2 of Example 20) was dissolved in 7 mL of chloroform, and 300 mg of NBS was added to the solution, and then the mixture was stirred at room temperature for 2 hours. After the solvent was distilled off under reduced pressure, the resulting residue was purified by silica gel column chromatography to obtain 337 mg of the objective compound as pale yellow oil.

Step 2

Production of 2-chloro-3,5-dimethyl-6-[2-(4-methylphenyl)pyrrolidin-1-yl]pyrazine 375 mg of 2,6-dibromo-3-chloro-5-[2-(4-methylphenyl)pyrrolidin-1-yl]pyrazine, 200 mg of methylboronic acid, 360 mg of potassium carbonate and 70 mg of [PdCl$_2$(dppf)$_2$]CH$_2$Cl$_2$ were added sequentially to a degassed mixed solvent of 6 mL of 1,4-dioxane and 2 mL of water, and the mixture was stirred at 100° C. for 8 hours under an argon atmosphere. The reaction mixture was diluted with ethyl acetate, and was washed with water and brine sequentially, and then the obtained organic layer was dried over magnesium sulfate. After the solvent was distilled off under reduced pressure, the resulting residue was purified by silica gel column chromatography to obtain 198 mg of the objective compound.

Step 3

Production of 2-({3,5-dimethyl-6-[2-(4-methylphenyl)pyrrolidin-1-yl]pyrazin-2-yl}amino)-1,3-thiazole-5-carbonitrile 4 mL of 1,4-dioxane was added to 197 mg of 2-chloro-3,5-dimethyl-6-[2-(4-methylphenyl)pyrrolidin-1-yl]pyrazine, 82 mg of 2-amino-1,3-thiazole-5-carbonitrile, 110 mg of t-Butyl XPhos, 276 mg of tripotassium phosphate and 89 mg of Pd$_2$(dba)$_3$, and the mixture was degassed, and then was stirred at 100° C. for one hour under an argon atmosphere. The reaction mixture was diluted with ethyl acetate, and was washed with water, and then the obtained organic layer was dried over magnesium sulfate. After the solvent was distilled off under reduced pressure, the resulting residue was purified by silica gel column chromatography to obtain 138 mg of the objective compound as a pale yellow powder.
MS (ESI) m/z 391 (M+H)$^+$

Example 44

2-({6-[2-(4-Chlorophenyl)pyrrolidin-1-yl]-3-cyclopropyl-5-methylpyrazin-2-yl}amino)-1,3-thiazole-5-carbonitrile

Step 1

Production of 2-bromo-5-chloro-3-[2-(4-chlorophenyl)pyrrolidin-1-yl]-6-cyclopropylpyrazine 85 mg of 3-chloro-5-[2-(4-chlorophenyl)pyrrolidin-1-yl]-2-cyclopropylpyrazine (Step 3 of Example 31) was dissolved in 3 mL of chloroform, and 68 mg of NBS was added to the solution, and then the mixture was stirred at room temperature overnight. After the solvent was distilled off under reduced pressure, the resulting residue was purified by silica gel column chromatography to obtain 140 mg of the objective compound as pale yellow oil.

Step 2

Production of 2-chloro-6-[2-(4-chlorophenyl)pyrrolidin-1-yl]-3-cyclopropyl-5-methylpyrazine 138 mg of 2-bromo-5-chloro-3-[2-(4-chlorophenyl)pyrrolidin-1-yl]-6-cyclopropylpyrazine, 39 mg of methylboronic acid, 138 mg of potassium carbonate and 27 mg of [PdCl$_2$(dppf)$_2$]CH$_2$Cl$_2$ were added sequentially to a degassed mixed solvent of 3 mL of 1,4-dioxane and 1 mL of water, and the mixture was stirred at 100° C. for 2 hours under an argon atmosphere. The reaction mixture was diluted with ethyl acetate, and was washed with water and brine sequentially, and then the obtained organic layer was dried over magnesium sulfate. After the solvent was distilled off under reduced pressure, the resulting residue was purified by silica gel column chromatography to obtain 95 mg of the objective compound.

Step 3

Production of 2-({6-[2-(4-chlorophenyl)pyrrolidin-1-yl]-3-cyclopropyl-5-methylpyrazin-2-yl}amino)-1,3-thiazole-5-carbonitrile 2 mL of 1,4-dioxane was added to 94 mg of 2-chloro-6-[2-(4-chlorophenyl)pyrrolidin-1-yl]-3-cyclopropyl-5-methylpyrazine, 34 mg of 2-amino-1,3-thiazole-5-carbonitrile, 46 mg of t-Butyl XPhos, 114 mg of tripotassium phosphate and 37 mg of Pd$_2$(dba)$_3$, and the mixture was degassed, and then was stirred at 90° C. for one hour under an argon atmosphere. The reaction mixture was diluted with ethyl acetate, and was washed with water, and then the obtained organic layer was dried over magnesium sulfate. After the solvent was distilled off under reduced pressure, the resulting residue was purified by silica gel column chromatography to obtain 26 mg of the objective compound as a pale yellow powder.

MS (ESI) m/z 437 (M+H)$^+$

Example 45

N-(5-Ethyl-1,3-thiazol-2-yl)-6-[2-(4-methylphenyl)pyrrolidin-1-yl]pyrazine-2-amine The objective compound was obtained as a pale green powder by the same process as in Example 1 using 2-(4-methylphenyl)pyrrolidine instead of (2S)-2-(4-methylphenyl)pyrrolidine in Step 1, and using 2-amino-5-ethylthiazole instead of 2-amino-1,3-thiazole-5-carbonitrile in Step 2.

MS (ESI) m/z 366 (M+H)$^+$

Example 46

2-({6-[2-(3-Methylphenyl)pyrrolidin-1-yl]pyrazin-2-yl}amino)-1,3-thiazole-5-carbonitrile The objective compound was obtained as a pale yellow powder by the same process as in Example 1 using 2-(3-methylphenyl)pyrrolidine (Reference example 12) instead of (2S)-2-(4-methylphenyl)pyrrolidine in Step 1.

MS (ESI) m/z 363 (M+H)$^+$

Example 47

2-({6-[2-(2-Methylphenyl)pyrrolidin-1-yl]pyrazin-2-yl}amino)-1,3-thiazole-5-carbonitrile The objective compound was obtained as a pale green powder by the same process as in Example 1 using 2-(2-methylphenyl)pyrrolidine (synthesized according to the method described in J. Org. Chem., 2001, 66, 6207) instead of (2S)-2-(4-methylphenyl)pyrrolidine in Step 1.

MS (ESI) m/z 363 (M+H)$^+$

Example 48

2-({6-[2-(4-Chlorophenyl)pyrrolidin-1-yl]pyrazin-2-yl}amino)-1,3-thiazole-5-carbonitrile The objective compound was obtained as a pale green powder by the same process as in Example 1 using 2-(4-chlorophenyl)pyrrolidine instead of (2S)-2-(4-methylphenyl)pyrrolidine in Step 1.

MS (ESI) m/z 383 (M+H)$^+$

Example 49

2-({6-(2-Fluoropyridin-3-yl)-5-methoxy-2-[2-(4-methylphen yl)pyrrolidin-1-yl]pyrimidin-4-yl}amino)-1,3-thiazole-5-carbonitrile The objective compound was obtained as a pale yellow powder by the same process as in Example 3 using 2-fluoropyridine-3-boronic acid instead of pyrimidine-5-boronic acid.

MS (ESI) m/z 488 (M+H)$^+$

Example 50

2-({6-(6-Fluoropyridin-3-yl)-5-methoxy-2-[2-(4-methylphenyl)pyrrolidin-1-yl]pyrimidin-4-yl}amino)-1,3-thiazole-5-carbonitrile The objective compound was obtained as a brown powder by the same process as in Example 3 using 2-fluoro-5-(4,4,5,5-tetramethyl-1,3,2-dioxaborolan-2-yl)-pyridine instead of pyrimidine-5-boronic acid.

MS (ESI) m/z 488 (M+H)$^4$

Example 51

Ethyl 2-({6-[2-(4-methylphenyl)pyrrolidin-1-yl]
pyrazin-2-yl}amino)-1,3-thiazole-5-carboxylate

Step 1

Production of 2-chloro-6-[2-(4-methylphenyl)pyrrolidin-1-yl]pyrazine 2.78 g of 2-(4-methylphenyl)pyrrolidine, 2.33 g of 2,6-dichloropyrazine and 4.0 mL of DIPEA were added to 8 mL of 1,4-dioxane, and the mixture was stirred at 120° C. for 45 minutes while irradiating microwave. After the reaction mixture was cooled to room temperature, the solvent was distilled off under reduced pressure. The resulting residue was purified by silica gel column chromatography to obtain 3.7 g of the objective compound as a white amorphous.

Step 2

Production of ethyl 2-({6-[2-(4-methylphenyl)pyrrolidin-1-yl]pyrazin-2-yl}amino)-1,3-thiazole-5-carboxylate 500 mg of 2-chloro-6-[2-(4-methylphenyl)pyrrolidin-1-yl]pyrazine, 632 mg of ethyl 2-amino-1,3-thiazole-5-carboxylate, 467 mg of t-Butyl XPhos, 779 mg of tripotassium phosphate and 251 mg of Pd$_2$(dba)$_3$ were added sequentially to 10 mL of degassed 1,4-dioxane, and the mixture was stirred at 100° C. overnight under an argon atmosphere. After the reaction mixture was cooled to room temperature, the solvent was distilled off under reduced pressure. The resulting residue was purified by silica gel column chromatography to obtain 278 mg of ethyl 2-({6-[2-(4-methylphenyl)pyrrolidin-1-yl]pyrazin-2-yl}amino)-1,3-thiazole-5-carboxylate as a pale yellow powder.

MS (ESI) m/z 410 (M+H)$^+$

Example 52

2-({5,6-Dimethyl-2-[2-(4-methylphenyl)pyrrolidin-1-yl]pyrimidin-4-yl}amino)-1,3-thiazole-5-carbonitrile The objective compound was obtained as a pale yellow powder by the same process as in Example 3 using 4,6-dichloro-5-methyl-2-[2-(4-methylphenyl)pyrrolidin-1-yl]pyrimidine instead of 4,6-dichloro-5-methoxy-2-[2-(4-methylphenyl)pyrrolidin-1-yl]pyrimidine, and using methylboronic acid instead of pyrimidine-5-boronic acid.

MS (ESI) m/z 391 (M+H)$^+$

Example 53

2-({6-[2-(4-Fluorophenyl)pyrrolidin-1-yl]-3-(2-methylpyridin-4-yl)pyrazin-2-yl}amino)-1,3-thiazole-5-carbonitrile The objective compound was obtained as a pale yellow powder by the same process as in Example 20 using 2-(4-fluorophenyl)pyrrolidine instead of (2S)-2-(4-methylphenyl)pyrrolidine in Step 1, and using 2-methylpyridine-4-boronic acid instead of methylboronic acid in Step 3.

MS (ESI) m/z 458 (M+H)$^+$

Example 54

6-[(5-Cyano-1,3-thiazol-2-yl)amino]-5-methyl-2-[(2S)-2-(4-methylphenyl)pyrrolidin-1-yl]-N-(1-methylpiperidin-4-yl)pyrimidine-4-carboxamide

Step 1

Production of ethyl 6-[(5-cyano-1,3-thiazol-2-yl)amino]-5-methyl-2-[(2S)-2-(4-methylphenyl)pyrrolidin-1-yl]pyrimidine-4-carboxylate A mixed solution of 2.0 g of 6-[(5-cyano-1,3-thiazol-2-yl)amino]-5-methyl-2-[(2S)-2-(4-methylphenyl)pyrrolidin-1-yl]pyrimidin-4-yl trifluoromethanesulfonate (Reference example 17), 125 mg of palladium(II) acetate, 615 mg of dppf, 3.2 mL of DIPEA, 40 mL of DMF, and 20 mL of ethanol was set under an argon atmosphere, and was bubbled with carbon monoxide for 5 minutes, and then the mixture was stirred at 80° C. overnight under a carbon monoxide atmosphere. The reaction mixture was diluted with ethyl acetate, and was washed with water and brine sequentially, and then the obtained organic layer was dried over magnesium sulfate. After the solvent was distilled off under reduced pressure, the resulting residue was purified by silica gel column chromatography to obtain 1.49 g of the objective compound as a pale yellow powder.

Step 2

Production of 6-[(5-cyano-1,3-thiazol-2-yl)amino]-5-methyl-2-[(2S)-2-(4-methylphenyl)pyrrolidin-1-yl]pyrimidine-4-carboxylic acid 1.3 g of the objective compound was obtained as a yellow powder by the same process as in Example 7 using 1.49 g of ethyl 6-[(5-cyano-1,3-thiazol-2-yl)amino]-5-methyl-2-[(2S)-2-(4-methylphenyl)pyrrolidin-1-yl]pyrimidine-4-carboxylate, 2.6 mL of 10% sodium hydroxide aqueous solution and 5 mL of THF.

Step 3

Production of 6-[(5-cyano-1,3-thiazol-2-yl)amino]-5-methyl-2-[(2S)-2-(4-methylphenyl)pyrrolidin-1-yl]-N-(1-methylpiperidin-4-yl)pyrimidine-4-carboxamide 19 mg of the objective compound was obtained as a white powder by the same process as in Example 12 using 25 mg of 6-[(5-cyano-1,3-thiazol-2-yl)amino]-5-methyl-2-[(2S)-2-(4-methylphenyl)pyrrolidin-1-yl]pyrimidine-4-carboxylic acid, 20 mg of 4-amino-1-methylpiperidine, 46 mg of PyBOP (Registered Trademark), 30 mg of DIPEA and 1 mL of DMF.

MS (ESI) m/z 517 (M+H)$^+$

Example 55

2-[(5-Cyano-1,3-thiazol-2-yl)amino]-N,3-dimethyl-6-[(2S)-2-(4-methylphenyl)pyrrolidin-1-yl]pyridine-4-carboxamide

Step 1

Production of tert-butyl 2-chloro-6-[(2S)-2-(4-methylphenyl)pyrrolidin-1-yl]pyridine-4-carboxylate 1.5 g of tert-butyl 2,6-dichloroisonicotinate and 1.02 g of (S)-2-(4-methylphenyl)pyrrolidine were dissolved in 1-butanol, and 2.0 mL of DIPEA was added to the solution, and then the mixture was stirred at 100° C. overnight. After the solvent was distilled off under reduced pressure, the resulting residue was purified by silica gel column chromatography to obtain 1.1 g of the objective compound as a yellow oil.

Step 2

Production of tert-butyl 3-bromo-2-chloro-6-[(2S)-2-(4-methylphenyl)pyrrolidin-1-yl]pyridine-4-carboxylate 1.1 g of tert-butyl 2-chloro-6-[(2S)-2-(4-methylphenyl) pyrrolidin-1-yl]pyridine-4-carboxylate was dissolved in 10 mL of chloroform, and 604 mg of NBS was added to the solution under ice-water cooling, and then the mixture was stirred overnight. After the solvent was distilled off under reduced pressure, the resulting residue was purified by silica gel column chromatography to obtain 797 mg of the objective compound as a yellow solid.

Step 3

Production of tert-butyl 2-chloro-3-methyl-6-[(2S)-2-(4-methylphenyl)pyrrolidin-1-yl]pyridine-4-carboxylate 637 mg of the objective compound was obtained as a pale yellow powder by the same process as in Step 1 of Example 3 using 797 mg of tert-butyl 3-bromo-2-chloro-6-[(2S)-2-(4-methylphenyl)pyrrolidin-1-yl]pyridine-4-carboxylate, 112 mg of methylboronic acid, 730 mg of potassium carbonate, 144 mg of [PdCl$_2$(dppf)$_2$]CH$_2$Cl$_2$, 18 mL of 1,4-dioxane and 6 mL of water.

Step 4

Production of tert-butyl 2-[(5-cyano-1,3-thiazol-2-yl)amino]-3-methyl-6-[(2S)-2-(4-methylphenyl)pyrrolidin-1-yl]pyridine-4-carboxylate 720 mg of the objective compound was obtained as a pale yellow powder by the same process as in Step 2 of Example 3 using 623 mg of tert-butyl 2-chloro-3-methyl-6-[(2S)-2-(4-methylphenyl)pyrrolidin-1-yl]pyridine-4-carboxylate, 302 mg of 2-amino-1,3-thiazole-5-carbonitrile, 273 mg of t-Butyl XPhos, 752 mg of tripotassium phosphate, 222 mg of Pd$_2$(dba)$_3$ and 10 mL of 1,4-dioxane.

Step 5

Production of 2-[(5-cyano-1,3-thiazol-2-yl)amino]-3-methyl-6-[(2S)-2-(4-methylphenyl)pyrrolidin-1-yl] pyridine-4-carboxylic acid 720 mg of tert-butyl 2-[(5-cyano-1,3-thiazol-2-yl)amino]-3-methyl-6-[(2S)-2-(4-methylphenyl)pyrrolidin-1-yl]pyridine-4-carboxylate was dissolved in 25 mL of acetonitrile, and 2.1 g of montmorillonite K-10 was added to the solution, and the mixture was stirred for 24 hours while being heated to reflux. The mixture was diluted with THF, and was filtered off with Celite (Registered Trademark), and then the mother liquid was distilled off under reduced pressure to obtain 493 mg of the objective compound as a yellow solid.

Step 6

Production of 2-[(5-cyano-1,3-thiazol-2-yl)amino]-N,3-dimethyl-6-[(2S)-2-(4-methylphenyl)pyrrolidin-1-yl]pyridine-4-carboxamide 11 mg of the objective compound was obtained as a white powder by the same process as in Example 12 using 25 mg of 2-[(5-cyano-1,3-thiazol-2-yl)amino]-3-methyl-6-[(2S)-2-(4-methylphenyl)pyrrolidin-1-yl]pyridine-4-carboxylic acid, 12 mg of methylamine hydrochloride, 47 mg of PyBOP (Registered Trademark), 30 mg of DIPEA and 1 mL of DMF.
MS (ESI) m/z 433 (M+H)$^+$ Example 56

N-(5-Fluoro-1,3-thiazol-2-yl)-5-methoxy-6-methyl-2-[(2S)-2-(4-methylphenyl)pyrrolidin-1-yl]pyrimidine-4-amine The objective compound was obtained as a black powder by the same process as in Example 9 using 2-amino-5-fluorothiazole instead of 2-amino-1,3-thiazole-5-carbonitrile.
MS (ESI) m/z 400 (M+H)$^+$ Example 57

2-({5-Ethyl-6-(methoxymethyl)-2-[(2S)-2-(4-methylphenyl)pyrrolidin-1-yl]pyrimidin-4-yl}amino)-1,3-thiazole-5-carbo nitrile Step 1

Production of methyl 2-ethyl-4-methoxy-3-oxobutanoate 371 mg of 60% sodium hydride was suspended in 20 mL of THF under an argon atmosphere, and 1.0 mL of methyl 4-methoxy-3-oxobutanoate was added dropwise to the suspension under ice-water cooling. The mixture was stirred at room temperature for 30 minutes, and was added with 0.34 mL of ethyl iodide, and then was stirred at 70° C. for 3 hours. Water was added to the reaction mixture, and the mixture was subjected to an extraction with ethyl acetate. The organic layer was washed with brine and the obtained organic layer was dried over magnesium sulfate. The solvent was distilled off under reduced pressure, and then the resulting residue was purified by silica gel column chromatography to obtain 192 mg of the objective compound as a colorless oil.

Step 2

Production of 5-ethyl-6-(methoxymethyl)-2-[(2S)-2-(4-methylphenyl)pyrrolidin-1-yl]pyrimidine-4-ol 218 mg of (2S)-2-(4-methylphenyl)pyrrolidine-1-carboximidamide hydrochloride and 190 mg of methyl 2-ethyl-4-methoxy-3-oxobutanoate were dissolved in 5 mL of ethanol, 0.36 mL of 5 M sodium methoxide/methanol solution was added to the solution, and the mixture was stirred at 90° C. for 5 hours under an argon atmosphere.
After the reaction mixture was cooled, the solvent was distilled off under reduced pressure. The resulting residue was added with 18 mL of water and was acidified by 10% hydrochloric acid. The mixture was stirred for 30 minutes and was neutralized by saturated sodium bicarbonate aqueous solution and was subjected to an extraction with ethyl acetate. The obtained organic layer was washed with brine, and then was dried over magnesium sulfate. The solvent was distilled off under reduced pressure to obtain 262 mg of the objective compound as a pale yellow oil.

Step 3

Production of 5-ethyl-6-(methoxymethyl)-2-[(2S)-2-(4-methylphenyl)pyrrolidin-1-yl]pyrimidin-4-yl trifluoromethanesulfonate 127 mg of the objective compound was obtained as a colorless oil by the same process as in Example 8 using 105 mg of 5-ethyl-6-(methoxymethyl)-2-[(2S)-2-(4-methylphenyl)pyrrolidin-1-yl]pyrimidine-4-ol, 70 µL of trifluoromethanesulfonic anhydride, 89 µL of triethylamine and 8 mL of dichloromethane.

Step 4

Production of 2-({5-ethyl-6-(methoxymethyl)-2-[(2S)-2-(4-methylphenyl)pyrrolidin-1-yl]pyrimidin-4-yl}amino)-1,3-thiazole-5-carbonitrile 22 mg of the objective compound was obtained as an orange powder by the same process as in Step 2 of Example 3 using 125 mg of 5-ethyl-6-(methoxymethyl)-2-[(2S)-2-(4-methylphenyl)pyrrolidin-1-yl]pyrimidin-4-yl trifluoromethanesulfonate, 34 mg of 2-amino-1,3-thiazole-5-carbonitrile, 34 mg of t-Butyl XPhos, 114 mg of tripotassium phosphate, 28 mg of $Pd_2(dba)_3$ and 3 mL of 1,4-dioxane.
MS (ESI) m/z 435 (M+H)$^+$ Example 58

2-({5-Methoxy-6-[1-(2-methoxyethyl)-1H-pyrazol-4-yl]-2-[(2S)-2-(4-methylphenyl)pyrrolidin-1-yl]pyrimidin-4-yl}amino)-1,3-thiazole-5-carbonitrile Step 1

Production of 5-methoxy-6-[1-(2-methoxyethyl)-1H-pyrazol-4-yl]-2-[(2S)-2-(4-methylphenyl)pyrrolidin-1-yl]pyrimidin-4-yl trifluoromethanesulfonate 1.2 g of 5-methoxy-2-[(2S)-2-(4-methylphenyl)pyrrolidin-1-yl]pyrimidin-4,6-diyl bis(trifluoromethanesulfonate) (Reference example 8), 640 mg of 1-(2-methoxyethyl)-4-(4,4,5,5-tetramethyl-1,3,2-dioxaborolan-2-yl)-1H-pyrazol (Reference example 15), 590 mg of potassium carbonate and 87 mg of $[PdCl_2(dppf)_2]CH_2Cl_2$ were added sequentially to a degassed mixed solvent of 10 mL of 1,4-dioxane and 1 mL of water, and the mixture was stirred at 95° C. for 3 hours under an argon atmosphere. The reaction solution was diluted with ethyl acetate, and the obtained organic layer was washed with water and brine sequentially, and then was dried over magnesium sulfate. The solvent was distilled off under reduced pressure, and then the obtained residue was purified by silica gel column chromatography to obtain 794 mg of the objective compound as a yellow oil.

Step 2

Production of 2-({5-methoxy-6-[1-(2-methoxyethyl)-1H-pyrazol-4-yl]-2-[(2S)-2-(4-methylphenyl)pyrrolidin-1-yl]pyrimidin-4-yl}amino)-1,3-thiazole-5-carbonitrile 5 mL of 1,4-dioxane was added to 790 mg of 5-methoxy-6-[1-(2-methoxyethyl)-1H-pyrazol-4-yl]-2-[(2S)-2-(4-methylphenyl)pyrrolidin-1-yl]pyrimidin-4-yl trifluoromethanesulfonate, 452 mg of 2-amino-1,3-thiazole-5-carbonitrile, 510 mg of t-Butyl XPhos, 957 mg of tripotassium phosphate and 550 mg of $Pd_2(dba)_3$. The mixture was degassed, and then was stirred at 100° C. for 4 hours under an argon atmosphere. The reaction solution was diluted with ethyl acetate, and the obtained organic layer was washed with water, and then was dried over magnesium sulfate. The solvent was distilled off under reduced pressure, and then the resulting residue was purified by silica gel column chromatography to obtain 441 mg of the objective compound as a pale yellow powder.
MS (ESI) m/z 517 (M+H)$^+$ Example 59

2-({6-[1-(2-Hydroxyethyl)-1H-pyrazol-4-yl]-5-methoxy-2-[(2S)-2-(4-methylphenyl)pyrrolidin-1-yl]pyrimidin-4-yl}amino)-1,3-thiazole-5-carbonitrile Step 1

Production of 2-({6-[1-(2-{[tert-butyl(diphenyl)silyl]oxy}ethyl)-1H-pyrazol-4-yl]-5-methoxy-2-[(2S)-2-(4-methylphenyl)pyrrolidin-1-yl]pyrimidin-4-yl}amino)-1,3-thiazole-5-carbonitrile 170 mg of 6-[(5-cyano-1,3-thiazol-2-yl)amino]-5-methoxy-2-[(2S)-2-(4-methylphenyl)pyrrolidin-1-yl]pyrimidin-4-yl trifluoromethanesulfonate (Reference examples 13), 225 mg of 1-(2-{[tert-butyl(diphenyl)silyl]oxy}ethyl)-4-(4,4,5,5-tetramethyl-1,3,2-dioxaborolan-2-yl)-1H-pyrazole, 87 mg of potassium carbonate and 51 mg of $[PdCl_2(dppf)_2]CH_2Cl_2$ were added sequentially to a degassed mixed solvent of 2 mL of 1,4-dioxane and 0.4 mL of water, and the mixture was stirred at 100° C. for 5 hours under an argon atmosphere. The reaction solution was diluted with ethyl acetate, and the obtained organic layer was washed with water and brine sequentially, and then was dried over magnesium sulfate. The solvent was distilled off under reduced pressure, and then the resulting residue was purified by silica gel column chromatography to obtain 166 mg of the objective compound.

Step 2

Production of 2-({6-[1-(2-hydroxyethyl)-1H-pyrazol-4-yl]-5-methoxy-2-[(2S)-2-(4-methylphenyl)pyrrolidin-1-yl]pyrimidin-4-yl}amino)-1,3-thiazole-5-carbonitrile 166 mg of 2-({6-[1-(2-{[tert-butyl(diphenyl)silyl]oxy}ethyl)-1H-pyrazol-4-yl]-5-methoxy-2-[(2S)-2-(4-methylphenyl)pyrrolidin-1-yl]pyrimidin-4-yl}amino)-1,3-thiazole-5-carbonitrile was dissolved in 2 mL of acetonitrile, and 0.2 mL of methanol and 0.29 mL of methanesulfonic acid were added to the solution, and the mixture was stirred at room temperature overnight. 15 mL of saturated sodium

Example 60

2-({5-Methoxy-2'-methyl-2-[(2S)-2-(4-methylphenyl)pyrrolidin-1-yl]-4,5'-bipyrimidin-6-yl}amino)-1,3-thiazole-5-carbonitrile 250 mg of 6-[(5-cyano-1,3-thiazol-2-yl)amino]-5-methoxy-2-[(2S)-2-(4-methylphenyl)pyrrolidin-1-yl]pyrimidin-4-yl trifluoromethanesulfonate, 200 mg of 2-methyl-5-(4,4,5,5-tetramethyl-1,3,2-dioxaborolan-2-yl)pyrimidine, 130 mg of potassium carbonate and 38 mg of [PdCl$_2$(dppf)$_2$]CH$_2$Cl$_2$ were added sequentially to a degassed mixed solvent of 4 mL of 1,4-dioxane and 1 mL of water, and the mixture was stirred at 100° C. for 40 minutes under an argon atmosphere. The reaction solution was diluted with ethyl acetate, and the obtained organic layer was washed with water and brine sequentially, and then was dried over magnesium sulfate. The solvent was distilled off under reduced pressure, and then the resulting residue was purified by silica gel column chromatography to obtain 220 mg of the objective compound as a yellow powder.

MS (ESI) m/z 485 (M+H)$^+$

Example 61

2-(4-{5-Methoxy-2-[(2S)-2-(4-methylphenyl)pyrrolidin-1-yl]-6-(1,2,4-thiadiazol-5-ylamino)pyrimidin-4-yl}-1H-pyrazol-1-yl)ethanol The objective compound was obtained as a yellow powder by the same process as in Example 59 using 5-methoxy-2-[(2S)-2-(4-methylphenyl)pyrrolidin-1-yl]-6-(1,2,4-thiadiazol-5-ylamino)pyrimidin-4-yl trifluoromethanesulfonate instead of 6-[(5-cyano-1,3-thiazol-2-yl)amino]-5-methoxy-2-[(2S)-2-(4-methylphenyl)pyrrolidin-1-yl]pyrimidin-4-yl trifluoromethanesulfonate.

MS (ESI) m/z 479 (M+H)$^+$

Example 62

6-[(5-Cyano-1,3-thiazol-2-yl)amino]-N-(trans-4-hydroxycyclohexyl)-5-methoxy-2-[(2S)-2-(4-methylphenyl)pyrrolidin-1-yl]pyrimidine-4-carboxamide Step 1

Production of 6-[(5-cyano-1,3-thiazol-2-yl)amino]-5-methoxy-2-[(2S)-2-(4-methylphenyl)pyrrolidin-1-yl]pyrimidine-4-carboxylic acid The objective compound was obtained as a pale yellow powder by the same process as in Steps 1 and 2 of Example 54 using 6-[(5-cyano-1,3-thiazol-2-yl)amino]-5-methoxy-2-[(2S)-2-(4-methylphenyl)pyrrolidin-1-yl]pyrimidin-4-yl trifluoromethanesulfonate (Reference example 13) instead of 6-[(5-cyano-1,3-thiazol-2-yl)amino]-5-methyl-2-[(2S)-2-(4-methylphenyl)pyrrolidin-1-yl]pyrimidin-4-yl trifluoromethanesulfonate.

MS (ESI) m/z 503 (M+H)$^+$

Step 2

Production of 6-[(5-cyano-1,3-thiazole-2-yl)amino]-N-(trans-4-hydroxycyclohexyl)-5-methoxy-2-[(2S)-2-(4-methylphenyl)pyrrolidin-1-yl]pyrimidine-4-carboxamide 41 mg of the objective compound was obtained as a white powder by the same process as in Example 12 using 50 mg of 6-[(5-cyano-1,3-thiazol-2-yl)amino]-5-methoxy-2-[(2S)-2-(4-methylphenyl)pyrrolidin-1-yl]pyrimidine-4-carboxylic acid, 26 mg of trans-4-aminocyclohexanol, 65 mg of HBTU, 44 mg of DIPEA, and 1 mL of DMF.

MS (ESI) m/z 534 (M+H)$^+$

Example 63

Trans-4-[({6-[(5-cyano-1,3-thiazol-2-yl)amino]-5-methoxy-2-[(2S)-2-(4-methylphenyl)pyrrolidin-1-yl]pyrimidin-4-yl}carbonyl)amino]cyclohexanecarboxylic acid Step 1

Production of methyl trans-4-[({6-[(5-cyano-1,3-thiazol-2-yl)amino]-5-methoxy-2-[(2S)-2-(4-methylphenyl)pyrrolidin-1-yl]pyrimidin-4-yl}carbonyl)amino]cyclohexanecarboxylate 113 mg of the objective compound was obtained as a pale yellow powder by the same process as in Example 12 using 100 mg of 6-[(5-cyano-1,3-thiazol-2-yl)amino]-5-methoxy-2-[(2S)-2-(4-methylphenyl)pyrrolidin-1-yl]pyrimidine-4-carboxylic acid, 66 mg of methyl trans-4-aminocyclohexane carboxylate, 130 mg of HBTU, 88 mg of DIPEA, and 2 mL of DMF.

Step 2

Production of trans-4-[({6-[(5-cyano-1,3-thiazol-2-yl)amino]-5-methoxy-2-[(2S)-2-(4-methylphenyl)pyrrolidin-1-yl]pyrimidin-4-yl}carbonyl)amino]cyclohexanecarboxylic acid 69 mg of the objective compound was obtained as a pale yellow powder by the same process as in Example 7 using 111 mg of methyl trans-4-[{6-[(5-cyano-1,3-thiazol-2-yl)amino]-5-methoxy-2-[(2S)-2-(4-methylphenyl)pyrrolidin-1-yl]pyrimidin-4-yl}carbonyl)amino]cyclohexanecarboxylate, 0.4 mL of 10% sodium hydroxide aqueous solution, 2 mL of THF and 2 mL of methanol.

MS (ESI) m/z 562 (M+H)$^+$

Example 64

6-[(5-Cyano-1,3-thiazol-2-yl)amino]-5-methoxy-N-(2-methoxyethyl)-2-[(2S)-2-(4-methylphenyl)pyrrolidin-1-yl]pyrimidine-4-carboxamide 43 mg of the objective compound was obtained as a pale yellow powder by the same process as in Example 12 using 30 mg of 6-[(5-cyano-1,3-thiazol-2-yl)amino]-5-methoxy-2-[(2S)-2-(4-methylphenyl)pyrrolidin-1-yl]pyrimidine-4-carboxylic acid, 15 mg of 2-methoxyethylamine, 54 mg of PyBOP (Registered Trademark), 44 mg of DIPEA, and 1 mL of DMF.

MS (ESI) m/z 494 (M+H)$^+$

Example 65

2-({6-(6-Hydroxypyridin-3-yl)-5-methoxy-2-[(2S)-2-(4-methylphenyl)pyrrolidin-1-yl]pyrimidin-4-yl}amino)-1,3-thiazole-5-carbonitrile

Step 1

Production of 2-({6-(6-methoxypyridin-3-yl)-5-methoxy-2-[(2S)-2-(4-meth ylphenyl)pyrrolidin-1-yl]pyrimidin-4-yl}amino)-1,3-thiazole-5-carbonitrile The objective compound was obtained as a yellow powder by the same process as in Example 9 using 2-methoxy-5-pyridineboronic acid instead of methylboronic acid.

Step 2

Production of 2-({6-(6-hydroxypyridin-3-yl)-5-methoxy-2-[(2S)-2-(4-methylphenyl)pyrrolidin-1-yl] pyrimidin-4-yl}amino)-1,3-thiazole-5-carbonitrile 60 mg of the objective compound was obtained as a brown powder by the same process as in Example 16 using 75 mg of 2-({6-(6-methoxypyridin-3-yl)-5-methoxy-2-[(2S)-2-(4-meth ylphenyl)pyrrolidin-1-yl]pyrimidin-4-yl}amino)-1,3-thiazole-5-carbonitrile, 67 mg of NaI, 49 mg of trimethylsilyl chloride, and 2 mL of acetonitrile.
MS (ESI) m/z 486 (M+H)$^+$

Example 66

2-[(5-Cyano-1,3-thiazol-2-yl)amino]-3-cyclopropyl-6-[(2S)-2-(4-methylphenyl)pyrrolidin-1-yl]pyridine-4-carboxamide The objective compound was obtained as a pale yellow powder by the same process as in Example 55 using cyclopropylboronic acid instead of methylboronic acid in Step 3, and using ammonium chloride instead of methylamine hydrochloride in Step 6.
MS (ESI) m/z 445 (M+H)$^+$

Example 67

6-[(5-Cyano-1,3-thiazol-2-yl)amino]-5-ethyl-2-[(2S)-2-(4-methylphenyl)pyrrolidin-1-yl]-N-(methylsulfonyl)pyrimidine-4-carboxamide

Step 1

Production of 6-[(5-cyano-1,3-thiazol-2-yl)amino]-5-ethyl-2-[(2S)-2-(4-methylphenyl)pyrrolidin-1-yl] pyrimidine-4-carboxylic acid The objective compound was obtained as a pale yellow powder by the same process as in Steps 1 and 2 of Example 54 using 6-[(5-cyano-1,3-thiazol-2-yl)amino]-5-ethyl-2-[(2S)-2-(4-methylphenyl)pyrrolidin-1-yl]pyrimidin-4-yl trifluoromethanesulfonate (Reference example 16) instead of 6-[(5-cyano-1,3-thiazol-2-yl)amino]-5-methyl-2-[(2S)-2-(4-methylphenyl)pyrrolidin-1-yl]pyrimidin-4-yl trifluoromethanesulfonate.

Step 2

Production of 6-[(5-cyano-1,3-thiazol-2-yl)amino]-5-ethyl-2-[(2S)-2-(4-methylphenyl)pyrrolidin-1-yl]-N-(methylsulfonyl)pyrimidine-4-carboxamide 68 mg of 6-[(5-cyano-1,3-thiazol-2-yl)amino]-5-ethyl-2-[(2S)-2-(4-methylphenyl)pyrrolidin-1-yl]pyrimidine-4-carboxylic acid was dissolved in 2 mL of THF, and 127 mg of 1,1'-carbonyldiimidazole and 79 mg of triethylamine were added to the solution and the mixture was stirred at room temperature for one hour. Subsequently, 143 mg of 1,8-diazabicyclo[5.4.0]-7-undecene and 89 mg of methanesulfonamide were added to the mixture and the mixture was stirred at 140° C. for 90 minutes while irradiating microwave. Acetic acid was added to the reaction mixture to neutralize, and then the mixture was diluted with ethyl acetate, and the organic layer was washed with water and brine sequentially, and was dried over magnesium sulfate. The solvent was distilled off under reduced pressure, and then the resulting residue was purified by silica gel column chromatography to obtain 53 mg of the objective compound as a yellow powder.
MS (ESI) m/z 512 (M+H)$^+$

Example 68

2-[(5-Cyano-1,3-thiazol-2-yl)amino]-N-(4-hydroxycyclohexyl)-3-methyl-6-[(2S)-2-(4-methylphenyl)pyrrolidin-1-yl]pyridine-4-carboxamide The objective compound was obtained as a pale yellow powder by the same process as in Example 55 using trans-4-aminocyclohexanol instead of methylamine hydrochloride in Step 6.
MS (ESI) m/z 517 (M+H)$^+$

Example 69

6-[(2S)-2-(4-Methylphenyl)pyrrolidin-1-yl]-4-(1-methyl-1H-pyrazol-4-yl)-N-(1,2,4-thiadiazol-5-yl) pyridine-2-amine

Step 1

Production of 2,6-dichloro-4-(1-methyl-1H-pyrazol-4-yl)pyridine 500 mg of 2,6-dichloro-4-iodopyridine, 379 mg of 1-methyl-4-(4,4,5,5-tetramethyl-1,3,2-dioxaborolan-2-yl)-1H-pyrazole, 753 mg of potassium carbonate and 74 mg of 1,1'-bis(diphenylphosphino)ferrocene-palladium(II)dichloride-dichloromethane complex were added sequentially to a degassed mixed solution of 7.5 mL of dioxane and 2.5 mL of water, and the mixture was stirred at 90° C. for 2 hours under an argon atmosphere. The reaction mixture was diluted with ethyl acetate, and the organic layer was washed with water and brine sequentially, and was dried over magnesium sulfate. The solvent was distilled off under reduced pressure, and then the resulting residue was purified by silica gel column chromatography to obtain 257 mg of the objective compound.

Step 2

Production of 2-chloro-6-[(2S)-2-(4-methylphenyl)pyrrolidin-1-yl]-4-(1-methyl-1H-pyrazol-4-yl)pyridine 2 mL of toluene was added to 161 mg of 2,6-dichloro-4-(1-methyl-1H-pyrazol-4-yl)pyridine, 137 mg of (2S)-2-(4-methylphenyl)pyrrolidine, 57 mg of DPEphos, 102 mg of sodium tert-butoxide and 16 mg of palladium(II)acetate, and the mixture was degassed, and then was stirred at 100° C. for 9 hours under an argon atmosphere. The reaction mixture was diluted with ethyl acetate, and the organic layer was washed with water, and was dried over magnesium sulfate. The solvent was distilled off under reduced pressure, and then the resulting residue was purified by silica gel column chromatography to obtain 104 mg of the objective compound as a colorless oil.

Step 3

Production of 6-[(2S)-2-(4-methylphenyl)pyrrolidin-1-yl]-4-(1-methyl-1H-pyrazol-4-yl)-N-(1,2,4-thiadiazol-5-yl)pyridine-2-amine 21 mg of the objective compound was obtained as a yellow powder by the same process as in Step 2 of Example 3 using 104 mg of 2-chloro-6-[(2S)-2-(4-methylphenyl)pyrrolidin-1-yl]-4-(1-methyl-1H-pyrazol-4-yl)pyridine, 33 mg of 5-amino-1,2,4-thiadiazole, 50 mg of t-Butyl XPhos, 125 mg of tripotassium phosphate, 40 mg of $Pd_2(dba)_3$ and 2 mL of 1,4-dioxane.

MS (ESI) m/z 418 $(M+H)^+$

Example 70

2-({5-Ethyl-6-methyl-2-[(2S)-2-(4-methylphenyl)pyrrolidin-1-yl]pyrimidin-4-yl}amino)-1,3-thiazole-5-carbonitrile maleate The objective compound was obtained as a pale yellow powder by the same process as in Example 9 using 5-ethyl-6-methyl-2-[(2S)-2-(4-methylphenyl)pyrrolidin-1-yl]pyrimidin-4-yl trifluoromethanesulfonate (Step 2 of Reference example 16) instead of 5-methoxy-6-methyl-2-[(2S)-2-(4-methylphenyl)pyrrolidin-1-yl]pyrimidin-4-yl trifluoromethanesulfonate in Step 1.

MS (ESI) m/z 405 $(M+H)^+$
Elemental analysis value (as $C_{26}H_{28}N_6O_4S$)
Calculated value (%) C, 59.98; H, 5.42; N, 16.14.
Found value (%) C, 59.88; H, 5.43; N, 15.90.

Example 71

2-({6-Acetyl-2-[(2S)-2-(4-methylphenyl)pyrrolidin-1-yl]-5,6,7,8-tetrahydropyrido[4,3-d]pyrimidin-4-yl}amino)-1,3-thiazole-5-carbonitrile Step 1

Production of tert-butyl 4-hydroxy-2-[(2S)-2-(4-methylphenyl)pyrrolidin-1-yl]-7,8-dihydropyrido[4,3-d]pyrimidine-6(5H)-carboxylate 902 mg of the objective compound was obtained as a pale yellow powder by the same process as in Reference example 2 using 500 mg of (S)-2-(4-methylphenyl)pyrrolidine-1-carboximidamide hydrochloride, 678 mg of 1-tert-butyl 3-ethyl-4-oxopiperidine-1,3-dicarboxylate, 0.84 mL of 5 M sodium methoxide/methanol solution and 10 mL of ethanol.

Step 2

Production of tert-butyl 2-[(2S)-2-(4-methylphenyl)pyrrolidin-1-yl]-4-{[(trifluoromethyl)sulfonyl]oxy}-7,8-dihydropyrido[4,3-d]pyrimidine-6(5H)-carboxylate 1.02 g of the objective compound was obtained as a colorless oil by the same process as in Example 8 using 900 mg of tert-butyl 4-hydroxy-2-[(2S)-2-(4-methylphenyl)pyrrolidin-1-yl]-7,8-dihydropyrido[4,3-d]pyrimidine-6(5H)-carboxylate, 0.48 mL of trifluoromethanesulfonic anhydride, 0.61 mL of triethylamine and 15 mL of dichloromethane.

Step 3

Production of tert-butyl 4-[(5-cyano-1,3-thiazol-2-yl)amino]-2-[(2S)-2-(4-methylphenyl)pyrrolidin-1-yl]-7,8-dihydropyrido[4,3-d]pyrimidine-6(5H)-carboxylate 372 mg of the objective compound was obtained as a pale yellow powder by the same process as in Step 2 of Example 10 using 1.02 g of tert-butyl 2-[(2S)-2-(4-methylphenyl)pyrrolidin-1-yl]-4-{[(trifluoromethyl)sulfonyl]oxy}-7,8-dihydropyrido[4,3-d]pyrimidine-6(5H)-carboxylate, 235 mg of 2-amino-1,3-thiazole-5-carbonitrile, 319 mg of t-Butyl XPhos, 797 mg of tripotassium phosphate, 292 mg of $Pd_2(dba)_3 \cdot CHCl_3$, and 10 mL of 1,4-dioxane.

Step 4

Production of 2-({2-[(2S)-2-(4-methylphenyl)pyrrolidin-1-yl]-5,6,7,8-tetrahydropyrido[4,3-d]pyrimidin-4-yl}amino)-1,3-thiazole-5-carbonitrile 2 mL of trifluoroacetic acid was added to 370 mg of tert-butyl 4-[(5-cyano-1,3-thiazol-2-yl)amino]-2-[(2S)-2-(4-methylphenyl)pyrrolidin-1-yl]-7,8-dihydropyrido[4,3-d]pyrimidine-6(5H)-carboxylate, and the mixture was stirred at room temperature for one hour. Saturated sodium bicarbonate aqueous solution was added to the mixture to make the mixture alkaline, and then the reaction solution was subjected to an extraction with ethyl acetate. The obtained organic layer was washed with water and brine sequentially and then dried over magnesium sulfate. The solvent was distilled off under reduced pressure, and then the resulting residue was purified by silica gel column chromatography to obtain 200 mg of the objective compound as a pale yellow powder.

Step 5

Production of 2-({6-acetyl-2-[(2S)-2-(4-methylphenyl)pyrrolidin-1-yl]-5,6,7,8-tetrahydropyrido[4,3-d]pyrimidin-4-yl}amino)-1,3-thiazole-5-carbonitrile 100 mg of 2-({2-[(2S)-2-(4-methylphenyl)pyrrolidin-1-yl]-5,6,7,8-tetrahydropyrido[4,3-d]pyrimidin-4-yl}amino)-1,3-thiazole-5-carbonitrile was dissolved in a mixed solvent of 1.5 mL of methylene chloride and 1.5 mL of THF, 83 μL of triethylamine and 29 μL of acetic anhydride were added to the solution, and the mixture was stirred at room temperature for 4 hours. Water was added to the mixture, and then the mixture was subjected to an extraction with methylene chloride, and the obtained organic layer was dried over magnesium sulfate. The solvent was distilled off under reduced pressure, and then the obtained solid was filtered to obtain 80 mg of the objective compound as a pale yellow powder.

MS (ESI) m/z 460 (M+H)⁺

Example 72

2-({2-[2-(4-Methylphenyl)pyrrolidin-1-yl]-6-(methylsulfonyl)-5,6,7,8-tetrahydropyrido[4,3-d]pyrimidin-4-yl}amino)-1,3-thiazole-5-carbonitrile

Step 1

Production of 2-({2-[2-(4-methylphenyl)pyrrolidin-1-yl]-5,6,7,8-tetrahydropyrido[4,3-d]pyrimidin-4-yl}amino)-1,3-thiazole-5-carbonitrile The objective compound was obtained as a pale yellow powder by the same process as in Steps 1 to 4 of Example 71 using 2-(4-methylphenyl)pyrrolidine-1-carboximidamide hydrochloride instead of (S)-2-(4-methylphenyl)pyrrolidine-1-carboximidamide hydrochloride.

Step 2

Production of 2-({2-[2-(4-methylphenyl)pyrrolidin-1-yl]-6-(methylsulfonyl)-5,6,7,8-tetrahydropyrido[4,3-d]pyrimidin-4-yl}amino)-1,3-thiazole-5-carbonitrile 50 mg of 2-({2-[2-(4-methylphenyl)pyrrolidin-1-yl]-5,6,7,8-tetrahydropyrido[4,3-d]pyrimidin-4-yl}amino)-1,3-thiazole-5-carbonitrile was dissolved in 2 mL of methylene chloride, and 42 μL of DIPEA and 11 μL of methanesulfonyl chloride were added to the solution, and the mixture was stirred at room temperature for one hour. Water was added to the mixture, and the mixture was subjected to an extraction with methylene chloride, and the obtained organic layer was dried over magnesium sulfate. The solvent was distilled off under reduced pressure, and then the obtained solid was filtered to obtain 35 mg of the objective compound as a white powder.

MS (ESI) m/z 496 (M+H)⁺

The structural formulas of Example 1-Example 72 are shown in Table 1 to Table 5.

TABLE 1

| Example No. | Structural formula |
|---|---|
| 1 | (structure: 5-methyl-thiazol-2-yl-amino pyrazine with 2-(4-methylphenyl)pyrrolidinyl substituent, HCl salt) |

TABLE 1-continued

| Example No. | Structural formula |
|---|---|
| 2 | (structure: 5-cyano-thiazol-2-yl-amino 5-methyl-pyrimidine with 2-(4-methylphenyl)pyrrolidinyl substituent) |
| 3 | (structure: 5-cyano-thiazol-2-yl-amino 5-methoxy-pyrimidine with pyrimidin-5-yl and 2-(4-methylphenyl)pyrrolidinyl substituents) |
| 4 | (structure: 5-cyano-thiazol-2-yl-amino 5-methoxy-pyrimidine with 4-carbamoylphenyl and 2-(4-methylphenyl)pyrrolidinyl substituents) |
| 5 | (structure: 5-cyano-thiazol-2-yl-amino 5-methoxy-pyrimidine with pyridin-3-yl and 2-(4-methylphenyl)pyrrolidinyl substituents) |

TABLE 1-continued

| Example No. | Structural formula |
|---|---|
| 6 | (structure) |
| 7 | (structure) |
| 8 | (structure) |
| 9 | (structure) |
| 10 | (structure) |
| 11 | (structure) |
| 12 | (structure) |
| 13 | (structure) |

TABLE 1-continued
| Example No. | Structural formula |
|---|---|
| 14 | 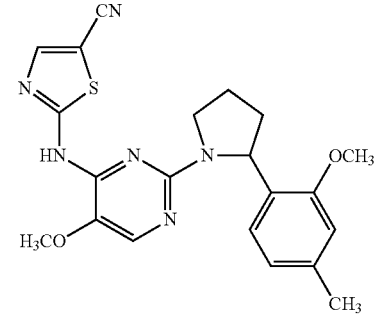 [SMILES: COc1cc(C)ccc1C1CCCN1c1ncc(OC)c(Nc2ncc(C#N)s2)n1] |
| 15 | |
TABLE 2
| Example No. | Structural formula |
|---|---|
| 16 | |
| 17 | 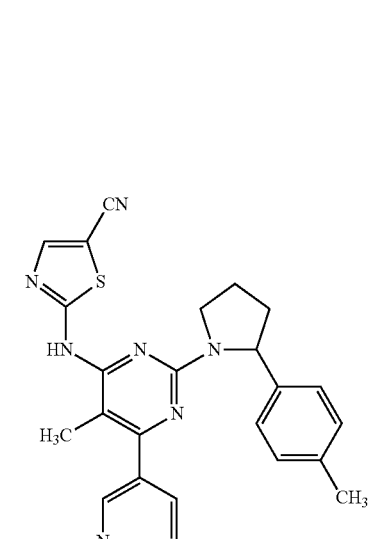 |
| 18 | |
| 19 | |
| 20 | |

TABLE 2-continued

| Example No. | Structural formula |
|---|---|
| 21 | |
| 22 | |
| 23 | |
| 24 | |
| 25 | |
| 26 | |
| 27 | |
| 28 | |
| 29 | |

TABLE 2-continued

| Example No. | Structural formula |
|---|---|
| 30 | (structure) |
| 31 | (structure) |
| 32 | (structure) |
| 33 | (structure) |

TABLE 3

| Example No. | Structural formula |
|---|---|
| 34 | (structure) |
| 35 | (structure) |
| 36 | (structure) |
| 37 | (structure) |
| 38 | (structure) |

TABLE 3-continued

| Example No. | Structural formula |
|---|---|
| 39 | |
| 40 | |
| 41 | |
| 42 | |
| 43 | |
| 44 | |
| 45 | |
| 46 | |
| 47 | |

TABLE 3-continued

| Example No. | Structural formula |
|---|---|
| 48 | (structure) |
| 49 | (structure) |
| 50 | (structure) |
| 51 | (structure) |

TABLE 4

| Example No. | Structural formula |
|---|---|
| 52 | (structure) |
| 53 | (structure) |
| 54 | (structure) |
| 55 | (structure) |

TABLE 4-continued

| Example No. | Structural formula |
|---|---|
| 56 | (5-fluorothiazol-2-yl)-HN / pyrimidine with OCH3, CH3, and (R)-2-(p-tolyl)pyrrolidin-1-yl |
| 57 | (5-cyanothiazol-2-yl)-HN / pyrimidine with ethyl, CH2OCH3, and (R)-2-(p-tolyl)pyrrolidin-1-yl |
| 58 | (5-cyanothiazol-2-yl)-HN / pyrimidine with OCH3, 1-(2-methoxyethyl)pyrazol-4-yl, and (R)-2-(p-tolyl)pyrrolidin-1-yl |
| 59 | (5-cyanothiazol-2-yl)-HN / pyrimidine with OCH3, 1-(2-hydroxyethyl)pyrazol-4-yl, and (R)-2-(p-tolyl)pyrrolidin-1-yl |
| 60 | (5-cyanothiazol-2-yl)-HN / pyrimidine with OCH3, 2-methylpyrimidin-5-yl, and (R)-2-(p-tolyl)pyrrolidin-1-yl |
| 61 | (1,2,4-thiadiazol-5-yl)-HN / pyrimidine with OCH3, 1-(2-hydroxyethyl)pyrazol-4-yl, and (R)-2-(p-tolyl)pyrrolidin-1-yl |
| 62 | (5-cyanothiazol-2-yl)-HN / pyrimidine with OCH3, trans-4-hydroxycyclohexylcarboxamide, and (R)-2-(p-tolyl)pyrrolidin-1-yl |
| 63 | (5-cyanothiazol-2-yl)-HN / pyrimidine with OCH3, trans-4-carboxycyclohexylcarboxamide, and (R)-2-(p-tolyl)pyrrolidin-1-yl |

TABLE 4-continued
| Example No. | Structural formula |
|---|---|
| 64 | 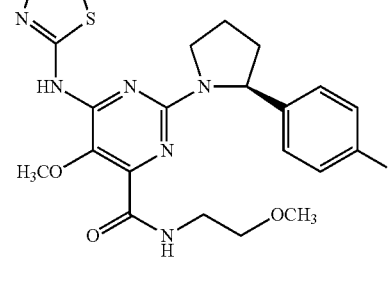 |
| 65 | |
| 66 | |
| 67 | |
TABLE 4-continued
| Example No. | Structural formula |
|---|---|
| 68 | 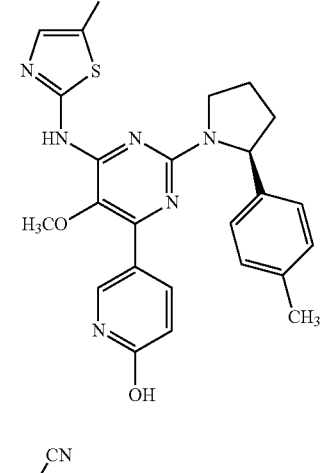 |
| 69 | |
TABLE 5
| Example No. | Structural formula |
|---|---|
| 70 | 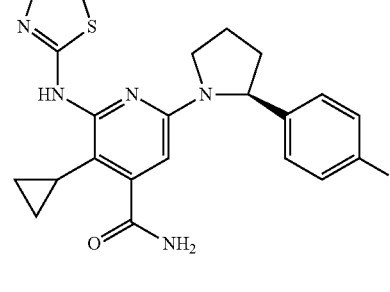 |
| 71 | 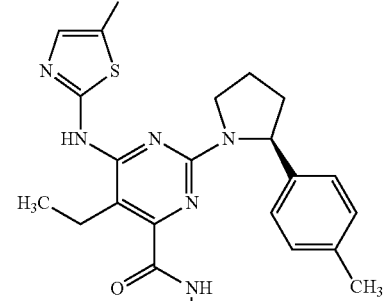 |

TABLE 5-continued

| Example No. | Structural formula |
|---|---|
| 72 | (structure: thiazole-CN linked via HN to pyrido-pyrimidine with methylsulfonyl and 2-(p-tolyl)pyrrolidinyl substituents) |

Test Example 1

ROS Tyrosine Kinase and JAK2 Tyrosine Kinase Inhibitory Activity Test

1. Preparation of Test Substance:

A test substance was dissolved in dimethyl sulfoxide (DMSO) to 10 mM and further diluted with DMSO to concentrations of 100-fold of the concentrations to be measured (100, 10, 1, 0.1, and 0.01 μM). Furthermore, the resultant was diluted with an assay buffer to 20-fold, thereby preparing a solution as a test substance solution. A solution prepared by diluting DMSO with an assay buffer to 20-fold was used as a negative control. A buffer containing 15 mM Tris-Cl (pH 7.5), 0.01 (v/v) % Tween-20, and 1 mM dithiothreitol was used as the assay buffer.

2. Measurement of ROS Tyrosine Kinase Activity and JAK2 Tyrosine Kinase Activity:

The activity was measured by adopting the ELISA method. Each of the test substance solutions was added to a streptavidine-coated 96-well plate (DELFIA Strip Plate 8×12 wells, PerkinElmer Co., Ltd,) at 10 μL per well (n=2), and a substrate solution (625 nM biotinylated peptide substrate, 25 μM ATP, 25 mM $MgCl_2$, 15 mM Tris-Cl (pH 7.5), 0.01 (v/v) % Tween-20, and 1 mM dithiothreitol) was added to the plate at 20 μL per well, and the resulting mixture was stirred. Finally, an ROS kinase or a JAK2 kinase (derived from humans, Carna Biosciences, Inc.) (diluted with the assay buffer to 0.25 nM) was added to the plate at 20 μL per well, and the resulting mixture was stirred. A reaction was performed at 30° C. for one hour. After the plate was washed 4 times with a washing buffer (50 mM Tris-Cl (pH 7.5), 150 mM NaCl, and 0.02 (v/v) % Tween-20), a blocking buffer (0.1% bovine serum albumin, 50 mM Tris-Cl (pH 7.5), 150 mM NaCl, and 0.02 (v/v) % Tween-20) was added to the plate at 150 μL per well, and incubated at 30° C. for 30 minutes. The blocking buffer was then removed, and a horse radish peroxidase-labeled anti-phosphorylated tyrosine antibody (BD Biosciences, Inc.) (diluted with the blocking buffer to 10,000-fold) was added to the plate at 100 μL per well, and the plate was incubated at 30° C. for 30 minutes. After the plate was washed 4 times with the washing buffer, a 3,3',5,5'-tetramethylbenzidine solution (Sigma-Aldrich Co., Ltd.) was added to the plate at 100 μL per well to develop the color for 10 minutes. The reaction was stopped by adding 0.1 M sulfuric acid at 100 μL per well. An absorbance at 450 nm was measured with a microplate reader (Model 3550, manufactured by BIO-RAD, Benchmark, manufactured by BIO-RAD, or iMARK, manufactured by BIO-RAD).

3. Analysis of Measurement Results:

A non-linear regression analysis was performed for the measured absorbance with an SAS system (SAS Institute Inc.), and a concentration of each of the test substances of inhibiting the ROS tyrosine kinase activity or JAK2 tyrosine kinase activity at 50% ($IC_{50}$) was calculated. The inhibitory activity ($IC_{50}$, nM) of each of the test substances against the ROS tyrosine kinase or JAK2 tyrosine kinase is shown in Tables 6 to 8.

TABLE 6

| Test Substance | Inhibitory activity to ROS tyrosine kinase ($IC_{50}$, nM) | Inhibitory activity to JAK2 tyrosine kinase ($IC_{50}$, nM) |
|---|---|---|
| Example 1 | 1.6 | 76 |
| Example 2 | 3.2 | 270 |
| Example 3 | 8.6 | >1000 |
| Example 4 | 35 | >1000 |
| Example 5 | 8.1 | >1000 |
| Example 6 | 7.1 | 92 |
| Example 7 | 0.6 | 37 |
| Example 8 | 3.9 | >1000 |
| Example 9 | 0.60 | 500 |
| Example 10 | 1.1 | 260 |
| Example 11 | 2.7 | >1000 |
| Example 12 | 21 | 540 |
| Example 13 | 44 | 1000 |
| Example 14 | 2.5 | 350 |
| Example 15 | 16 | >1000 |
| Example 16 | 1.5 | 36 |
| Example 17 | 39 | >1000 |
| Example 18 | 120 | >1000 |
| Example 19 | 2.6 | 220 |
| Example 20 | 1.1 | 250 |
| Example 21 | 13 | >1000 |
| Example 22 | 47 | >1000 |
| Example 23 | 8.8 | >1000 |
| Example 24 | 6.6 | 210 |
| Example 25 | 26 | >1000 |

TABLE 7

| Test Substance | Inhibitory activity to ROS tyrosine kinase ($IC_{50}$, nM) | Inhibitory activity to JAK2 tyrosine kinase ($IC_{50}$, nM) |
|---|---|---|
| Example 26 | 12 | >1000 |
| Example 27 | 65 | >1000 |
| Example 28 | 51 | >1000 |
| Example 29 | 1.3 | 140 |
| Example 30 | 0.5 | 69 |
| Example 31 | 5.3 | 390 |
| Example 32 | 4.4 | >1000 |
| Example 33 | 2.2 | 190 |
| Example 34 | 4.1 | >1000 |
| Example 35 | 2.9 | >1000 |
| Example 36 | 1.0 | 240 |
| Example 37 | 13 | 560 |
| Example 38 | 18 | 620 |
| Example 39 | 12 | >1000 |
| Example 40 | 2.1 | 230 |
| Example 41 | 0.71 | 21 |
| Example 42 | 1.6 | 100 |
| Example 43 | 4.2 | >1000 |
| Example 44 | 13 | 1000 |
| Example 45 | 7.3 | 210 |
| Example 46 | 6.4 | 280 |
| Example 47 | 17 | 280 |
| Example 48 | 0.6 | 31 |

TABLE 7-continued

| Test Substance | Inhibitory activity to ROS tyrosine kinase ($IC_{50}$, nM) | Inhibitory activity to JAK2 tyrosine kinase ($IC_{50}$, nM) |
|---|---|---|
| Example 49 | 52 | >1000 |
| Example 50 | 12 | 1000 |

TABLE 8

| Test Substance | Inhibitory activity to ROS tyrosine kinase ($IC_{50}$, nM) | Inhibitory activity to JAK2 tyrosine kinase ($IC_{50}$, nM) |
|---|---|---|
| Example 51 | 88 | 930 |
| Example 52 | 1.8 | 170 |
| Example 53 | 67 | >1000 |
| Example 54 | 3.9 | 190 |
| Example 55 | 0.6 | 24 |
| Example 56 | 6.7 | >1000 |
| Example 57 | 2.7 | >1000 |
| Example 58 | 2.2 | 240 |
| Example 59 | 1.5 | 190 |
| Example 60 | 2.3 | 740 |
| Example 61 | 2.5 | 490 |
| Example 62 | 2.1 | >1000 |
| Example 63 | 0.3 | 120 |
| Example 64 | 2.6 | >1000 |
| Example 65 | 1.3 | 260 |
| Example 66 | 0.84 | 910 |
| Example 67 | 1.5 | 370 |
| Example 68 | 0.76 | 22 |
| Example 69 | 11 | 17 |
| Example 70 | 2.9 | >1000 |
| Example 71 | 1.2 | 150 |
| Example 72 | 97 | >1000 |

Test Example 2

Proliferation Inhibitory Activity Test Against FIG-ROS/BaF3 Cell

1. Cell Seeding:

A BaF3 cell which had been transformed by introducing the FIG-ROS fusion gene (derived from U118MG human glioma cell) (FIG-ROS/BaF3 Cell) was prepared on a culture medium, seeded on a 96-well plate in the number of $1\times10^3/100$ μL per well, and then allowed to stand in a $CO_2$ incubator (at 37° C. and 5% $CO_2$). As the culture medium, 10% FBS (fetal bovine serum)-incorporated RPMI-1640 was used.

2. Proliferation Inhibitory Activity Test:

A test substance was dissolved in dimethyl sulfoxide (DMSO) to 10 mM and further diluted with DMSO to 100-fold to prepare a 100 μM solution. This was diluted with a 1% DMSO-incorporated medium to concentrations of 10-fold of the concentration to be measured (10,000, 1,000, 100, 10, and 1 nM). Each of the medicine solutions was added at 11 μL per well and mixed. To a control having no medicine added thereto, a 1% DMSO-incorporated medium was added, and incubated in a $CO_2$ incubator (at 37° C. and 5% $CO_2$) for 3 days. After completion of the incubation, the number of live cells was counted using a cell counting kit. First of all, each cell counting kit solution was added at 5 μL per well and mixed, and incubated in a $CO_2$ incubator (at 37° C. and 5% $CO_2$) for 4 hours. An absorbance at 450 nm was measured with a microplate reader (Model 3550, manufactured by BIO-RAD, Benchmark, manufactured by BIO-RAD, or iMARK, manufactured by BIO-RAD) with a reference wavelength of 650 nm.

3. Analysis of Measurement Results:

A non-linear regression analysis was performed for the measured absorbance with an SAS system (SAS Institute Inc.), and a concentration of each of the test substances of inhibiting the cell proliferation at 50% ($IC_{50}$) was calculated. The proliferation inhibitory activity ($IC_{50}$, nM) of each of the test substances against the FIG-ROS/BaF3 cell is shown in Table 9.

TABLE 9

| Test Substance | Proliferation inhibitory activity against FIG-ROS/BaF3 cell (IC50, nM) |
|---|---|
| Example 1 | 2.2 |
| Example 4 | 2.6 |
| Example 6 | 23 |
| Example 7 | 83 |
| Example 9 | 2.1 |
| Example 11 | 2.2 |
| Example 12 | 24 |
| Example 13 | 3.5 |
| Example 15 | 20 |
| Example 19 | 2.9 |
| Example 26 | 10 |
| Example 27 | 27 |
| Example 29 | 4.3 |
| Example 32 | 33 |
| Example 34 | 12 |
| Example 39 | 4.5 |
| Example 43 | 2.1 |
| Example 45 | 7.6 |
| Example 48 | 1.9 |
| Example 48 | 1.9 |
| Example 50 | 9.4 |
| Example 51 | 160 |
| Example 54 | 0.4 |
| Example 55 | 0.3 |
| Example 56 | 8.2 |
| Example 57 | 1.8 |
| Example 59 | 1.3 |
| Example 60 | 2.9 |
| Example 61 | 1.0 |
| Example 62 | 2.6 |
| Example 63 | 3.5 |
| Example 64 | 1.5 |
| Example 65 | 1.9 |
| Example 67 | 2.1 |
| Example 68 | 0.71 |
| Example 69 | 6.9 |
| Example 70 | 1.7 |
| Example 71 | 2.0 |

Formulation Example 1

Tablets (for Oral Administration)

Formulation: Each Tablet (80 mg) Contains the Following.

| | |
|---|---|
| Compound of Example 1 | 5.0 mg |
| Corn starch | 46.6 mg |
| Crystalline cellulose | 24.0 mg |
| Methyl cellulose | 4.0 mg |
| Magnesium stearate | 0.4 mg |

Tablets are prepared by tableting of the mixed powder in the above ratio according to a conventional method.

INDUSTRIAL APPLICABILITY

As described above, the compound of the present invention or its pharmaceutically acceptable salt has high ROS tyrosine kinase inhibitory activity and can be used as a preventing agent or a treating agent for especially glioma, non-small cell lung cancer, angiosarcoma, inflammatory myofibroblastic tumor, ovarian cancer, gastric cancer, ovarian cancer, epithelioid hemangioendothelioma, colorectal cancer, liposarcoma, or Spitzoid neoplasms.

The invention claimed is:

1. A compound represented by the following formula [1], a pharmaceutically acceptable salt thereof, an optical isomer thereof, or a pharmaceutically acceptable salt of an optical isomer thereof:

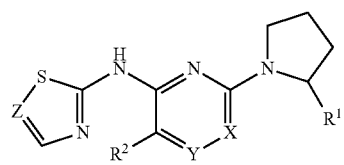

[1]

wherein
R$^1$ represents phenyl which may be substituted with one or two groups selected from the group consisting of halogen, alkyl optionally substituted by halogen, and alkoxy;
R$^2$ represents hydrogen, alkyl optionally substituted by halogen, cycloalkyl, alkoxy, or heteroaryl optionally substituted by alkyl;
X represents CR$^3$, and Y represents N or CR$^4$, or X represents N, and Y represents CR$^4$;
R$^3$ represents hydrogen or alkyl; and
R$^4$ represents
1) hydrogen,
2) alkyl which may be substituted with 1 to 3 groups selected from the group consisting of alkoxy and halogen,
3) cycloalkyl,
4) phenyl which may be substituted with one group selected from the group consisting of carbamoyl and alkylsulfonyl,
5) heteroaryl which may be substituted with one group selected from alkyl optionally substituted by hydroxy or alkoxy, halogen, hydroxy, and alkoxy,
6) carboxy,
7) alkyloxycarbonyl, or
8) carbamoyl which may be substituted with one or two groups selected from the group consisting of alkyl optionally substituted by hydroxy or alkoxy, alkylsulfonyl, saturated heterocyclic group optionally substituted by alkyl, and cycloalkyl optionally substituted by hydroxy or carboxy; and in the case where X represents N, and Y represents CR$^4$, R$^2$ and R$^4$ may be taken jointly to form a group represented by the following formula, together with the carbon atom to which R$^2$ bonds as well as the carbon atom to which R$^4$ bonds:

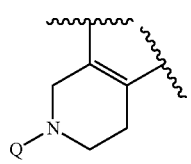

wherein
Q represents alkylcarbonyl or alkylsulfonyl;
Z represents CR$^5$ or N; and
R$^5$ represents alkyl, alkoxycarbonyl, halogen, or cyano.

2. The compound, pharmaceutically acceptable salt thereof, optical isomer thereof, or pharmaceutically acceptable salt of optical isomer thereof according to claim 1, wherein Z represents CR$^5$, and R$^5$ represents cyano.

3. The compound, pharmaceutically acceptable salt thereof, optical isomer thereof, or pharmaceutically acceptable salt of optical isomer thereof according to claim 2, wherein Y represents CR$^4$.

4. The compound, pharmaceutically acceptable salt thereof, optical isomer thereof, or pharmaceutically acceptable salt of optical isomer thereof according to claim 3, wherein X represents N.

5. The compound, pharmaceutically acceptable salt thereof, optical isomer thereof, or pharmaceutically acceptable salt of optical isomer thereof according to claim 4, wherein R$^2$ represents an alkyl or an alkoxy, or R$^2$ and R$^4$ are taken jointly to form a group represented by the following formula, together with the carbon atom to which R$^2$ bonds as well as the carbon atom to which R$^4$ bonds:

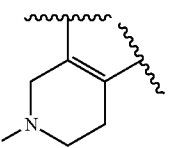

wherein Q represents alkylcarbonyl or alkylsulfonyl.

6. The compound, pharmaceutically acceptable salt thereof, optical isomer thereof, or pharmaceutically acceptable salt of optical isomer thereof according to claim 2, wherein the carbon atom to which R$^1$ bonds is of an S-configuration.

7. The compound, pharmaceutically acceptable salt thereof, optical isomer thereof, or pharmaceutically acceptable salt of optical isomer thereof according to claim 1, wherein R$^1$ represents alkyl-substituted phenyl.

8. The compound, pharmaceutically acceptable salt thereof, optical isomer thereof, or pharmaceutically acceptable salt of optical isomer thereof according to claim 7, wherein Y represents CR$^4$.

9. The compound, pharmaceutically acceptable salt thereof, optical isomer thereof, or pharmaceutically acceptable salt of optical isomer thereof according to claim 8, wherein X represents N.

10. The compound, pharmaceutically acceptable salt thereof, optical isomer thereof, or pharmaceutically acceptable salt of optical isomer thereof according to claim 9, wherein R$^2$ represents an alkyl or an alkoxy, or R$^2$ and R$^4$ are taken jointly to form a group represented by the following formula, together with the carbon atom to which R$^2$ bonds as well as the carbon atom to which R$^4$ bonds:

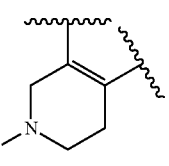

wherein Q represents alkylcarbonyl or alkylsulfonyl.

11. The compound, pharmaceutically acceptable salt thereof, optical isomer thereof, or pharmaceutically acceptable salt of optical isomer thereof according to claim 1, wherein Y represents $CR^4$.

12. The compound, pharmaceutically acceptable salt thereof, optical isomer thereof, or pharmaceutically acceptable salt of optical isomer thereof according to claim 11, wherein X represents N.

13. The compound, pharmaceutically acceptable salt thereof, optical isomer thereof, or pharmaceutically acceptable salt of optical isomer thereof according to claim 12, wherein $R^2$ represents an alkyl or an alkoxy, or $R^2$ and $R^4$ are taken jointly to form a group represented by the following formula, together with the carbon atom to which $R^2$ bonds as well as the carbon atom to which $R^4$ bonds:

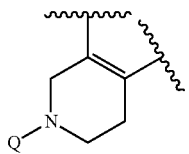

wherein Q represents alkylcarbonyl or alkylsulfonyl.

14. The compound, pharmaceutically acceptable salt thereof, optical isomer thereof, or pharmaceutically acceptable salt of optical isomer thereof according to claim 1, wherein the carbon atom to which $R^1$ bonds is of an S-configuration.

15. The compound, pharmaceutically acceptable salt thereof, optical isomer thereof, or pharmaceutically acceptable salt of optical isomer thereof according to claim 1, wherein the compound is selected from the group consisting of the following (1) to (71):

(1) 2-({6-[2-(4-methylphenyl)pyrrolidin-1-yl]pyrazin-2-yl}amino)-1,3-thiazole-5-carbonitrile,
(2) 2-({5-methyl-2-[2-(4-methylphenyl)pyrrolidin-1-yl]pyrimidin-4-yl}amino)-1,3-thiazole-5-carbonitrile,
(3) 2-({5-methoxy-2-[2-(4-methylphenyl)pyrrolidin-1-yl]-4,5'-bipyrimidin-6-yl}amino)-1,3-thiazole-5-carbonitrile,
(4) 4-{6-[(5-cyano-1,3-thiazol-2-yl)amino]-5-methoxy-2-[2-(4-methylphenyl)pyrrolidin-1-yl]pyrimidin-4-yl}benzamide,
(5) 2-({5-methoxy-2-[2-(4-methylphenyl)pyrrolidin-1-yl]-6-(pyridin-3-yl)pyrimidin-4-yl}amino)-1,3-thiazole-5-carbonitrile,
(6) methyl 6-[(5-cyano-1,3-thiazol-2-yl)amino]-2-[2-(4-methylphenyl)pyrrolidin-1-yl]pyrimidine-4-carboxylate,
(7) 6-[(5-cyano-1,3-thiazol-2-yl)amino]-2-[2-(4-methylphenyl)pyrrolidin-1-yl]pyrimidine-4-carboxylic acid,
(8) 2-({5-methyl-2-[2-(4-methylphenyl)pyrrolidin-1-yl]-6-(1-methyl-1H-pyrazol-4-yl)pyrimidin-4-yl}amino)-1,3-thiazole-5-carbonitrile,
(9) 2-({5-methoxy-6-methyl-2-[2-(4-methylphenyl)pyrrolidin-1-yl]pyrimidin-4-yl}amino)-1,3-thiazole-5-carbonitrile,
(10) 2-({5-methoxy-2-[2-(4-methylphenyl)pyrrolidin-1-yl]-6-(1-methyl-1H-pyrazol-4-yl)pyrimidin-4-yl}amino)-1,3-thiazole-5-carbonitrile,
(11) 2-({5-methoxy-2-[2-(4-methylphenyl)pyrrolidin-1-yl]-6-(1,3-oxazol-5-yl)pyrimidin-4-yl}amino)-1,3-thiazole-5-carbonitrile,
(12) 6-[(5-cyano-1,3-thiazol-2-yl)amino]-N-[(2R)-1-hydroxypropan-2-yl]-2-[2-(4-methylphenyl)pyrrolidin-1-yl]pyrimidine-4-carboxamide,
(13) 2-({5-methoxy-2-[2-(4-methylphenyl)pyrrolidin-1-yl]-6-[4-(methylsulfonyl)phenyl]pyrimidin-4-yl}amino)-1,3-thiazole-5-carbonitrile,
(14) 2-({5-methoxy-2-[2-(2-methoxy-4-methylphenyl)pyrrolidin-1-yl]pyrimidin-4-yl}amino)-1,3-thiazole-5-carbonitrile,
(15) 2-({6-(6-methoxypyridin-3-yl)-5-methyl-2-[2-(4-methylphenyl)pyrrolidin-1-yl]pyrimidin-4-yl}amino)-1,3-thiazole-5-carbonitrile,
(16) 2-({6-(6-hydroxypyridin-3-yl)-5-methyl-2-[2-(4-methylphenyl)pyrrolidin-1-yl]pyrimidin-4-yl}amino)-1,3-thiazole-5-carbonitrile,
(17) 2-({6-cyclopropyl-5-methoxy-2-[2-(4-methylphenyl)pyrrolidin-1-yl]pyrimidin-4-yl}amino)-1,3-thiazole-5-carbonitrile,
(18) 2-({5-methoxy-2-[2-(4-methylphenyl)pyrrolidin-1-yl]pyrimidin-4-yl}amino)-1,3-thiazole-5-carbonitrile,
(19) 2-({3-methyl-6-[2-(4-methylphenyl)pyrrolidin-1-yl]pyrazin-2-yl}amino)-1,3-thiazole-5-carbonitrile,
(20) 2-({6-[2-(4-fluorophenyl)pyrrolidin-1-yl]-3-(1,3-oxazol-5-yl)pyrazin-2-yl}amino)-1,3-thiazole-5-carbonitrile,
(21) 2-({6-[2-(4-fluorophenyl)pyrrolidin-1-yl]-3-(pyrimidin-5-yl)pyrazin-2-yl}amino)-1,3-thiazole-5-carbonitrile,
(22) 2-({3-cyclopropyl-6-[2-(2-methoxy-4-methylphenyl)pyrrolidin-1-yl]pyrazin-2-yl}amino)-1,3-thiazole-5-carbonitrile,
(23) 2-({3-cyclopropyl-6-[2-(2-methoxyphenyl)pyrrolidin-1-yl]pyrazin-2-yl}amino)-1,3-thiazole-5-carbonitrile,
(24) 2-({6-[2-(4-fluorophenyl)pyrrolidin-1-yl]-3-(furan-3-yl)pyrazin-2-yl}amino)-1,3-thiazole-5-carbonitrile,
(25) 2-({6-[2-(4-fluorophenyl)pyrrolidin-1-yl]-3-(pyridin-4-yl)pyrazin-2-yl}amino)-1,3-thiazole-5-carbonitrile,
(26) 2-({6-[2-(4-methylphenyl)pyrrolidin-1-yl]-4-(trifluoromethyl)pyridine-2-yl}amino)-1,3-thiazole-5-carbonitrile,
(27) 2-({6-[2-(4-fluorophenyl)pyrrolidin-1-yl]-3-(1-methyl-1H-pyrazol-4-yl)pyrazin-2-yl}amino)-1,3-thiazole-5-carbonitrile,
(28) 3-methyl-6-[2-(4-methylphenyl)pyrrolidin-1-yl]-N-(5-methyl-1,3-thiazol-2-yl)pyrazine-2-amine,
(29) 2-({6-[2-(2-methoxy-4-methylphenyl)pyrrolidin-1-yl]pyrazin-2-yl}amino)-1,3-thiazole-5-carbonitrile,
(30) 6-[2-(4-chlorophenyl)pyrrolidin-1-yl]-3-cyclopropyl-N-(5-methyl-1,3-thiazol-2-yl)pyrazine-2-amine,
(31) 2-({6-[2-(3,5-dimethoxyphenyl)pyrrolidin-1-yl]pyrazin-2-yl}amino)-1,3-thiazole-5-carbonitrile,
(32) 2-({6-[2-(3-methoxy-4-methylphenyl)pyrrolidin-1-yl]pyrazin-2-yl}amino)-1,3-thiazole-5-carbonitrile,
(33) 3-cyclopropyl-6-[2-(4-methylphenyl)pyrrolidin-1-yl]-N-(5-methyl-1,3-thiazol-2-yl)pyrazine-2-amine,
(34) 2-({3-cyclopropyl-6-[2-(4-methylphenyl)pyrrolidin-1-yl]pyrazin-2-yl}amino)-1,3-thiazole-5-carbonitrile,
(35) 2-({6-[2-(4-chlorophenyl)pyrrolidin-1-yl]-3-cyclopropylpyrazin-2-yl}amino)-1,3-thiazole-5-carbonitrile,
(36) 2-({6-[2-(4-methoxyphenyl)pyrrolidin-1-yl]pyrazin-2-yl}amino)-1,3-thiazole-5-carbonitrile,
(37) 2-({6-[2-(3-methoxyphenyl)pyrrolidin-1-yl]pyrazin-2-yl}amino)-1,3-thiazole-5-carbonitrile,
(38) 2-[(6-(2-[4-(trifluoromethyl)phenyl]pyrrolidin-1-yl)pyrazin-2-yl)amino]-1,3-thiazole-5-carbonitrile,

(39) 2-({3-cyclopropyl-6-[2-(4-fluorophenyl)pyrrolidin-1-yl]pyrazin-2-yl}amino)-1,3-thiazole-5-carbonitrile,
(40) 2-({6-[2-(4-fluorophenyl)pyrrolidin-1-yl]-3-methylpyrazin-2-yl}amino)-1,3-thiazole-5-carbonitrile,
(41) 2-({6-[2-(4-chlorophenyl)pyrrolidin-1-yl]-3-methylpyrazin-2-yl}amino)-1,3-thiazole-5-carbonitrile,
(42) 2-({3,5-dimethyl-6-[2-(4-methylphenyl)pyrrolidin-1-yl]pyrazin-2-yl}amino)-1,3-thiazole-5-carbonitrile,
(43) 2-({6-[2-(4-chlorophenyl)pyrrolidin-1-yl]-3-cyclopropyl-5-methylpyrazin-2-yl}amino)-1,3-thiazole-5-carbonitrile,
(44) N-(5-ethyl-1,3-thiazol-2-yl)-6-[2-(4-methylphenyl)pyrrolidin-1-yl]pyrazine-2-amine,
(45) 2-({6-[2-(3-methylphenyl)pyrrolidin-1-yl]pyrazin-2-yl}amino)-1,3-thiazole-5-carbonitrile,
(46) 2-({6-[2-(2-methylphenyl)pyrrolidin-1-yl]pyrazin-2-yl}amino)-1,3-thiazole-5-carbonitrile,
(47) 2-({6-[2-(4-chlorophenyl)pyrrolidin-1-yl]pyrazin-2-yl}amino)-1,3-thiazole-5-carbonitrile,
(48) 2-({6-(2-fluoropyridin-3-yl)-5-methoxy-2-[2-(4-methylphenyl)pyrrolidin-1-yl]pyrimidin-4-yl}amino)-1,3-thiazole-5-carbonitrile,
(49) 2-({6-(6-fluoropyridin-3-yl)-5-methoxy-2-[2-(4-methylphenyl)pyrrolidin-1-yl]pyrimidin-4-yl}amino)-1,3-thiazole-5-carbonitrile,
(50) ethyl 2-({6-[2-(4-methylphenyl)pyrrolidin-1-yl]pyrazin-2-yl}amino)-1,3-thiazole-5-carboxylate,
(51) 2-({5,6-dimethyl-2-[2-(4-methylphenyl)pyrrolidin-1-yl]pyrimidin-4-yl}amino)-1,3-thiazole-5-carbonitrile,
(52) 2-({6-[2-(4-fluorophenyl)pyrrolidin-1-yl]-3-(2-methylpyridin-4-yl)pyrazin-2-yl}amino)-1,3-thiazole-5-carbonitrile,
(53) 6-[(5-cyano-1,3-thiazol-2-yl)amino]-5-methyl-2-[2-(4-methylphenyl)pyrrolidin-1-yl]-N-(1-methylpiperidin-4-yl)pyrimidine-4-carboxamide,
(54) 2-[(5-cyano-1,3-thiazol-2-yl)amino]-N,3-dimethyl-6-[2-(4-methylphenyl)pyrrolidin-1-yl]pyridine-4-carboxamide,
(55) N-(5-fluoro-1,3-thiazol-2-yl)-5-methoxy-6-methyl-2-[2-(4-methylphenyl)pyrrolidin-1-yl]pyrimidine-4-amine,
(56) 2-({5-ethyl-6-(methoxymethyl)-2-[2-(4-methylphenyl)pyrrolidin-1-yl]pyrimidin-4-yl}amino)-1,3-thiazole-5-carbonitrile,
(57) 2-({5-methoxy-6-[1-(2-methoxyethyl)-1H-pyrazol-4-yl]-2-[2-(4-methylphenyl)pyrrolidin-1-yl]pyrimidin-4-yl}amino)-1,3-thiazole-5-carbonitrile,
(58) 2-({6-[1-(2-hydroxyethyl)-1H-pyrazol-4-yl]-5-methoxy-2-[2-(4-methylphenyl)pyrrolidin-1-yl]pyrimidin-4-yl}amino)-1,3-thiazole-5-carbonitrile,
(59) 2-({5-methoxy-2'-methyl-2-[2-(4-methylphenyl)pyrrolidin-1-yl]-4,5'-bipyrimidin-6-yl}amino)-1,3-thiazole-5-carbonitrile,
(60) 2-(4-(5-methoxy-2-[2-(4-methylphenyl)pyrrolidin-1-yl]-6-(1,2,4-thiadiazol-5-ylamino)pyrimidin-4-yl)-1H-pyrazol-1-yl)ethanol,
(61) 6-[(5-cyano-1,3-thiazol-2-yl)amino]-N-(trans-4-hydroxycyclohexyl)-5-methoxy-2-[2-(4-methylphenyl)pyrrolidin-1-yl]pyrimidine-4-carboxamide,
(62) trans-4-[({6-[(5-cyano-1,3-thiazol-2-yl)amino]-5-methoxy-2-[2-(4-methylphenyl)pyrrolidin-1-yl]pyrimidin-4-yl}carbonyl)amino]cyclohexanecarboxylic acid,
(63) 6-[(5-cyano-1,3-thiazol-2-yl)amino]-5-methoxy-N-(2-methoxyethyl)-2-[2-(4-methylphenyl)pyrrolidin-1-yl]pyrimidine-4-carboxamide,
(64) 2-({5-methoxy-2-[2-(4-methylphenyl)pyrrolidin-1-yl]-6-(6-oxo-1,6-dihydropyridin-3-yl)pyrimidin-4-yl}amino)-1,3-thiazole-5-carbonitrile,
(65) 2-[(5-cyano-1,3-thiazol-2-yl)amino]-3-cyclopropyl-6-[2-(4-methylphenyl)pyrrolidin-1-yl]pyridine-4-carboxamide,
(66) 6-[(5-cyano-1,3-thiazol-2-yl)amino]-5-ethyl-2-[2-(4-methylphenyl)pyrrolidin-1-yl]-N-(methylsulfonyl)pyrimidine-4-carboxamide,
(67) 2-[(5-cyano-1,3-thiazol-2-yl)amino]-N-(4-hydroxycyclohexyl)-3-methyl-6-[2-(4-methylphenyl)pyrrolidin-1-yl]pyridine-4-carboxamide,
(68) 6-[2-(4-methylphenyl)pyrrolidin-1-yl]-4-(1-methyl-1H-pyrazol-4-yl)-N-(1,2,4-thiadiazol-5-yl)pyridine-2-amine,
(69) 2-({5-ethyl-6-methyl-2-[2-(4-methylphenyl)pyrrolidin-1-yl]pyrimidin-4-yl}amino)-1,3-thiazole-5-carbonitrile,
(70) 2-({6-acetyl-2-[2-(4-methylphenyl)pyrrolidin-1-yl]-5,6,7,8-tetrahydropyrido[4,3-d]pyrimidin-4-yl}amino)-1,3-thiazole-5-carbonitrile, and
(71) 2-({2-[2-(4-methylphenyl)pyrrolidin-1-yl]-6-(methylsulfonyl)-5,6,7,8-tetrahydropyrido[4,3-d]pyrimidin-4-yl}amino)-1,3-thiazole-5-carbonitrile.

16. A pharmaceutical composition comprising:
the compound, pharmaceutically acceptable salt thereof, optical isomer thereof, or pharmaceutically acceptable salt of optical isomer thereof according to claim 1 as an active ingredient; and
a pharmaceutically acceptable, nontoxic and inactive carrier.

17. A pharmaceutical composition comprising:
the compound, pharmaceutically acceptable salt thereof, optical isomer thereof, or pharmaceutically acceptable salt of optical isomer thereof according to claim 6 as an active ingredient; and
a pharmaceutically acceptable, nontoxic and inactive carrier.

18. A pharmaceutical composition comprising:
the compound, pharmaceutically acceptable salt thereof, optical isomer thereof, or pharmaceutically acceptable salt of optical isomer thereof according to claim 14 as an active ingredient; and
a pharmaceutically acceptable, nontoxic and inactive carrier.

19. A pharmaceutical composition comprising:
the compound, pharmaceutically acceptable salt thereof, optical isomer thereof, or pharmaceutically acceptable salt of optical isomer thereof according to claim 15, as an active ingredient; and
a pharmaceutically acceptable, nontoxic and inactive carrier.

20. A method for inhibiting a ROS tyrosine kinase in a human, comprising the step of administering to the human the compound, pharmaceutically acceptable salt thereof, optical isomer thereof, or pharmaceutically acceptable salt of optical isomer thereof according to claim 1.

21. The method according to claim 20, wherein the human suffers from a disease or disorder selected from the group consisting of glioblastoma, non-small cell lung cancer, angiosarcoma, an inflammatory myofibroblastic tumor, cholangiocarcinoma, gastric cancer, ovarian cancer, epithelioid hemangioendothelioma, colorectal cancer, liposarcoma, and a Spitzoid neoplasm.

22. A method for inhibiting a ROS tyrosine kinase in a human, comprising the step of administering to the human the compound, pharmaceutically acceptable salt thereof, optical isomer thereof, or pharmaceutically acceptable salt of optical isomer thereof according to claim 15.

23. The method according to claim 22, wherein the human suffers from a disease or disorder selected from the group consisting of glioblastoma, non-small cell lung cancer, angiosarcoma, an inflammatory myofibroblastic tumor, cholangiocarcinoma, gastric cancer, ovarian cancer, epithelioid hemangioendothelioma, colorectal cancer, liposarcoma, and a Spitzoid neoplasm.

* * * * *